(12) United States Patent
Nobles et al.

(10) Patent No.: US 10,687,801 B2
(45) Date of Patent: Jun. 23, 2020

(54) SUTURE SPOOLS FOR TISSUE SUTURING DEVICE

(71) Applicant: Nobles Medical Technologies II, Inc., Fountain Valley, CA (US)

(72) Inventors: Anthony A. Nobles, Fountain Valley, CA (US); Daniel W. Haines, Bellaire, TX (US); Benjamin G. Brosch, Mission Viejo, CA (US); Tuan Ly, Fountain Valley, CA (US); Liem Pham, Fountain Valley, CA (US)

(73) Assignee: Nobles Medical Technologies II, Inc., Fountain Valley, CA (US)

( * ) Notice: Subject to any disclaimer, the term of this patent is extended or adjusted under 35 U.S.C. 154(b) by 0 days.

(21) Appl. No.: 15/578,134

(22) PCT Filed: Apr. 11, 2016

(86) PCT No.: PCT/US2016/026965
§ 371 (c)(1),
(2) Date: Nov. 29, 2017

(87) PCT Pub. No.: WO2017/180092
PCT Pub. Date: Oct. 19, 2017

(65) Prior Publication Data
US 2019/0029672 A1 Jan. 31, 2019

(51) Int. Cl.
*A61B 17/04* (2006.01)
*A61B 17/00* (2006.01)
(Continued)

(52) U.S. Cl.
CPC ...... *A61B 17/0491* (2013.01); *A61B 17/0057* (2013.01); *A61B 17/0401* (2013.01);
(Continued)

(58) Field of Classification Search
CPC . A61B 17/04; A61B 17/0491; A61B 17/0493; A61B 17/0469; A61B 17/0401;
(Continued)

(56) References Cited

U.S. PATENT DOCUMENTS

| 118,683 A | 9/1871 | Bruce |
|---|---|---|
| 1,064,307 A | 6/1913 | Fleming |

(Continued)

FOREIGN PATENT DOCUMENTS

| CN | 195341 | 2/2005 |
|---|---|---|
| CN | 101495049 | 12/2010 |

(Continued)

OTHER PUBLICATIONS

Extended Search Report from corresponding European Patent Application No. 16898790.7, dated Sep. 6, 2019, in 5 pages.

(Continued)

*Primary Examiner* — Katherine M Rodjom
(74) *Attorney, Agent, or Firm* — Knobbe, Martens, Olson & Bear, LLP

(57) ABSTRACT

Disclosed herein are embodiments of devices, systems and methods for suturing biological tissue incorporating one or more suture spools. The suture spools can be located external to a handle or elongate body of a suturing device, and can contain the sutures within an inner circumference of the suture spools. The suture spools can be configured to reduce entanglement of sutures during use in an operation.

22 Claims, 45 Drawing Sheets

(51) Int. Cl.
*A61B 17/06* (2006.01)
*A61B 17/22* (2006.01)
*A61B 17/32* (2006.01)

(52) U.S. Cl.
CPC ...... *A61B 17/0469* (2013.01); *A61B 17/0483* (2013.01); *A61B 17/0493* (2013.01); *A61B 17/06123* (2013.01); *A61B 2017/00477* (2013.01); *A61B 2017/00575* (2013.01); *A61B 2017/00663* (2013.01); *A61B 2017/0406* (2013.01); *A61B 2017/047* (2013.01); *A61B 2017/0409* (2013.01); *A61B 2017/0472* (2013.01); *A61B 2017/22038* (2013.01); *A61B 2017/320044* (2013.01)

(58) Field of Classification Search
CPC ............ A61B 17/06; A61B 2017/0472; A61B 2017/0409; A61B 2017/00663
See application file for complete search history.

(56) References Cited

U.S. PATENT DOCUMENTS

| | | | |
|---|---|---|---|
| 1,822,330 A | 9/1931 | Ainslie |
| 1,989,919 A | 2/1935 | Everitt |
| 2,348,218 A | 5/1944 | Karle |
| 2,473,742 A | 6/1949 | Auzin |
| 2,548,602 A | 4/1951 | Greenburg |
| 2,637,290 A | 5/1953 | Sigoda |
| 2,738,790 A | 3/1956 | Todt, Sr. et al. |
| 2,849,002 A | 8/1958 | Oddo |
| 2,945,460 A | 7/1960 | Kagiyama |
| 3,241,554 A | 3/1966 | Coanda |
| 3,292,627 A | 12/1966 | Harautuneian |
| 3,394,705 A | 7/1968 | Abramson |
| 3,664,345 A | 5/1972 | Dabbs et al. |
| 3,665,926 A | 5/1972 | Flores |
| 3,774,596 A | 11/1973 | Cook |
| 3,828,790 A | 8/1974 | Curtiss et al. |
| 3,831,587 A | 8/1974 | Boyd |
| 3,842,840 A | 10/1974 | Schweizer |
| 3,877,434 A | 4/1975 | Ferguson et al. |
| 3,882,852 A | 5/1975 | Sinnreich |
| 3,882,855 A | 5/1975 | Schulte et al. |
| 3,888,117 A | 6/1975 | Lewis |
| 3,903,893 A | 9/1975 | Scheer |
| 3,946,740 A | 3/1976 | Bassett |
| 3,946,741 A | 3/1976 | Adair |
| 3,952,742 A | 4/1976 | Taylor |
| 3,976,079 A | 8/1976 | Samuels |
| 4,052,980 A | 10/1977 | Grams et al. |
| RE29,703 E | 7/1978 | Fatt |
| 4,107,953 A | 8/1978 | Casillo |
| 4,119,100 A | 10/1978 | Rickett |
| 4,164,225 A | 8/1979 | Johnson et al. |
| 4,230,119 A | 10/1980 | Blum |
| 4,291,698 A | 9/1981 | Fuchs et al. |
| 4,299,237 A | 11/1981 | Foti |
| 4,307,722 A | 12/1981 | Evans |
| 4,345,601 A | 8/1982 | Fukuda |
| 4,351,342 A | 9/1982 | Wiita et al. |
| 4,417,532 A | 11/1983 | Yasukata |
| 4,423,725 A | 1/1984 | Baran et al. |
| 4,447,227 A | 5/1984 | Kotsanis |
| 4,457,300 A | 7/1984 | Budde |
| 4,484,580 A | 11/1984 | Nomoto et al. |
| 4,512,338 A | 4/1985 | Balko et al. |
| 4,546,759 A | 10/1985 | Solar |
| 4,553,543 A | 11/1985 | Amarasinghe |
| 4,573,966 A | 3/1986 | Weikl et al. |
| 4,589,868 A | 5/1986 | Dretler |
| 4,610,662 A | 9/1986 | Weikl et al. |
| 4,617,738 A | 10/1986 | Kopacz |
| 4,662,068 A | 5/1987 | Polonsky |
| 4,664,114 A | 5/1987 | Ghodsian |
| 4,734,094 A | 3/1988 | Jacob et al. |
| 4,744,364 A | 5/1988 | Kensey |
| 4,750,492 A | 6/1988 | Jacobs |
| 4,771,776 A | 9/1988 | Powell et al. |
| 4,774,091 A | 9/1988 | Yamahira et al. |
| 4,794,928 A | 1/1989 | Kletschka |
| 4,795,427 A | 1/1989 | Helzel |
| 4,796,629 A | 1/1989 | Grayzel |
| 4,824,436 A | 4/1989 | Wolinsky |
| 4,827,931 A | 5/1989 | Longmore |
| 4,841,888 A | 6/1989 | Mills et al. |
| 4,861,330 A | 8/1989 | Voss |
| 4,898,168 A | 2/1990 | Yule |
| 4,923,461 A | 5/1990 | Caspari et al. |
| 4,926,860 A | 5/1990 | Stice et al. |
| 4,932,956 A | 6/1990 | Reddy et al. |
| 4,935,027 A | 6/1990 | Yoon |
| 4,954,126 A | 9/1990 | Wallsten |
| 4,957,498 A | 9/1990 | Caspari et al. |
| 4,972,845 A | 11/1990 | Iversen et al. |
| 4,981,149 A | 1/1991 | Yoon et al. |
| 4,983,116 A | 1/1991 | Koga |
| 4,984,564 A | 1/1991 | Yuen |
| 4,994,070 A | 2/1991 | Waters |
| 5,002,531 A | 3/1991 | Bonzel |
| 5,021,059 A | 6/1991 | Kensey et al. |
| 5,037,433 A | 8/1991 | Wilk et al. |
| 5,057,114 A | 10/1991 | Wittich et al. |
| 5,059,201 A | 10/1991 | Asnis |
| 5,065,772 A | 11/1991 | Cox, Jr. |
| 5,074,871 A | 12/1991 | Groshong |
| 5,078,743 A | 1/1992 | Mikalov et al. |
| 5,090,958 A | 2/1992 | Sahota |
| 5,100,418 A | 3/1992 | Yoon et al. |
| 5,104,394 A | 4/1992 | Knoepfler |
| 5,106,363 A | 4/1992 | Nobuyoshi |
| 5,108,416 A | 4/1992 | Ryan et al. |
| 5,108,419 A | 4/1992 | Reger et al. |
| 5,116,305 A | 5/1992 | Milder et al. |
| 5,122,122 A | 6/1992 | Allgood |
| 5,129,883 A | 7/1992 | Black |
| 5,133,724 A | 7/1992 | Wilson et al. |
| 5,135,484 A | 8/1992 | Wright |
| 5,160,339 A | 11/1992 | Chen et al. |
| 5,163,906 A | 11/1992 | Ahmadi |
| 5,167,223 A | 12/1992 | Koros et al. |
| 5,171,251 A | 12/1992 | Bregen et al. |
| 5,176,691 A | 1/1993 | Pierce |
| 5,192,301 A | 3/1993 | Kamiya et al. |
| 5,222,508 A | 6/1993 | Contarini |
| 5,222,941 A | 6/1993 | Don Michael |
| 5,222,974 A | 6/1993 | Kensey et al. |
| 5,224,948 A | 7/1993 | Abe et al. |
| 5,236,443 A | 8/1993 | Sontag |
| 5,242,459 A | 9/1993 | Buelna |
| 5,281,234 A | 1/1994 | Wilk et al. |
| 5,281,237 A | 1/1994 | Gimpelson |
| 5,282,827 A | 2/1994 | Kensey et al. |
| 5,286,259 A | 2/1994 | Ganguly et al. |
| 5,290,249 A | 3/1994 | Foster et al. |
| 5,291,639 A | 3/1994 | Baum et al. |
| 5,300,106 A * | 4/1994 | Dahl ..................... A61N 1/05 604/164.05 |
| 5,304,184 A | 4/1994 | Hathaway et al. |
| 5,308,323 A | 5/1994 | Sogawa et al. |
| 5,312,344 A | 5/1994 | Grinfeld |
| 5,314,409 A | 5/1994 | Sarosiek et al. |
| 5,320,604 A | 6/1994 | Walker et al. |
| 5,320,632 A | 6/1994 | Heidmueller |
| 5,330,446 A | 7/1994 | Weldon et al. |
| 5,330,497 A | 7/1994 | Freitas et al. |
| 5,331,975 A | 7/1994 | Bonutti |
| 5,336,229 A | 8/1994 | Noda |
| 5,336,231 A | 8/1994 | Adair |
| 5,337,736 A | 8/1994 | Reddy |
| 5,339,801 A | 8/1994 | Poloyko |
| 5,342,306 A | 8/1994 | Don Michael |
| 5,342,385 A | 8/1994 | Norelli et al. |
| 5,342,393 A | 8/1994 | Stack |

(56) References Cited

U.S. PATENT DOCUMENTS

| | | |
|---|---|---|
| 5,350,399 A | 9/1994 | Erlebacher et al. |
| 5,356,382 A | 10/1994 | Picha et al. |
| 5,364,407 A | 11/1994 | Poll |
| 5,364,408 A | 11/1994 | Gordon |
| 5,368,601 A | 11/1994 | Sauer et al. |
| 5,370,618 A | 12/1994 | Leonhardt |
| 5,370,685 A | 12/1994 | Stevens |
| 5,374,275 A | 12/1994 | Bradley et al. |
| 5,380,284 A | 1/1995 | Don Michael |
| 5,382,261 A | 1/1995 | Palmaz |
| 5,383,854 A | 1/1995 | Safar et al. |
| 5,383,896 A | 1/1995 | Gershony et al. |
| 5,383,897 A | 1/1995 | Wholey |
| 5,383,905 A | 1/1995 | Golds et al. |
| 5,389,103 A | 2/1995 | Melzer et al. |
| 5,391,147 A | 2/1995 | Imran et al. |
| 5,391,174 A | 2/1995 | Weston |
| 5,395,383 A | 3/1995 | Adams et al. |
| 5,397,325 A | 3/1995 | Badia et al. |
| 5,403,329 A | 4/1995 | Hinchcliffe |
| 5,403,331 A | 4/1995 | Chesterfield et al. |
| 5,403,341 A | 4/1995 | Solar |
| 5,405,322 A | 4/1995 | Lennox et al. |
| 5,405,354 A | 4/1995 | Sarrett |
| 5,417,699 A | 5/1995 | Klein et al. |
| 5,417,700 A | 5/1995 | Egan |
| 5,423,777 A | 6/1995 | Tajiri et al. |
| 5,423,837 A | 6/1995 | Mericle et al. |
| 5,425,708 A | 6/1995 | Nasu |
| 5,425,737 A | 6/1995 | Burbank et al. |
| 5,425,744 A | 6/1995 | Fagan et al. |
| 5,429,118 A | 7/1995 | Cole et al. |
| 5,431,666 A | 7/1995 | Sauer et al. |
| 5,439,470 A | 8/1995 | Li |
| 5,445,167 A | 8/1995 | Yoon et al. |
| 5,447,515 A | 9/1995 | Robicsek |
| 5,452,513 A | 9/1995 | Zinnbauer et al. |
| 5,454,823 A | 10/1995 | Richardson et al. |
| 5,458,574 A | 10/1995 | Machold et al. |
| 5,458,609 A | 10/1995 | Gordon et al. |
| 5,462,560 A | 10/1995 | Stevens |
| 5,462,561 A | 10/1995 | Voda |
| 5,470,338 A | 11/1995 | Whitefield et al. |
| 5,474,572 A | 12/1995 | Hayburst |
| 5,476,469 A | 12/1995 | Hathaway et al. |
| 5,476,470 A | 12/1995 | Fitzgibbons, Jr. |
| 5,496,332 A | 3/1996 | Sierra et al. |
| 5,499,991 A | 3/1996 | Garman et al. |
| 5,501,691 A | 3/1996 | Goldrath |
| 5,507,754 A | 4/1996 | Green et al. |
| 5,507,755 A | 4/1996 | Gresl et al. |
| 5,514,159 A | 5/1996 | Matula et al. |
| 5,520,609 A | 5/1996 | Moll et al. |
| 5,520,702 A | 5/1996 | Sauer et al. |
| 5,522,961 A | 6/1996 | Leonhardt |
| 5,527,321 A | 6/1996 | Hinchliffe |
| 5,527,322 A | 6/1996 | Klein et al. |
| 5,527,338 A | 6/1996 | Purdy |
| 5,540,658 A | 7/1996 | Evans et al. |
| 5,540,704 A | 7/1996 | Gordon et al. |
| 5,545,170 A | 8/1996 | Hart |
| 5,549,633 A | 8/1996 | Evans et al. |
| 5,558,642 A | 9/1996 | Schweich et al. |
| 5,558,644 A | 9/1996 | Boyd et al. |
| RE35,352 E | 10/1996 | Peters |
| 5,562,686 A | 10/1996 | Sauer et al. |
| 5,562,688 A | 10/1996 | Riza |
| 5,565,122 A | 10/1996 | Zinnbauer et al. |
| 5,571,090 A | 11/1996 | Sherts |
| 5,573,540 A | 11/1996 | Yoon |
| 5,584,835 A | 12/1996 | Greenfield |
| 5,584,861 A | 12/1996 | Swain et al. |
| 5,591,195 A | 1/1997 | Taheri et al. |
| 5,593,422 A | 1/1997 | Muijs Van de Moer et al. |
| 5,599,307 A | 2/1997 | Bacher et al. |
| 5,603,718 A | 2/1997 | Xu |
| 5,613,974 A | 3/1997 | Andreas et al. |
| 5,613,975 A | 3/1997 | Christy |
| 5,626,590 A | 5/1997 | Wilk |
| 5,630,833 A | 5/1997 | Katsaros et al. |
| 5,632,751 A | 5/1997 | Piraka |
| 5,632,752 A | 5/1997 | Buelna |
| 5,634,936 A | 6/1997 | Linden et al. |
| 5,637,097 A | 6/1997 | Yoon |
| 5,643,289 A | 7/1997 | Sauer et al. |
| 5,645,553 A | 7/1997 | Kolesa et al. |
| 5,662,663 A | 9/1997 | Shallman |
| 5,669,917 A | 9/1997 | Sauer et al. |
| 5,669,971 A | 9/1997 | Bok et al. |
| 5,674,198 A | 10/1997 | Leone |
| 5,681,296 A | 10/1997 | Ishida |
| 5,681,351 A | 10/1997 | Jamiolkowski et al. |
| 5,688,245 A | 11/1997 | Runge |
| 5,690,674 A | 11/1997 | Diaz |
| 5,695,468 A | 12/1997 | Lafontaine et al. |
| 5,695,504 A | 12/1997 | Gifford, III et al. |
| 5,697,905 A | 12/1997 | D'Ambrosio |
| 5,700,273 A | 12/1997 | Buelna et al. |
| 5,700,277 A | 12/1997 | Nash et al. |
| 5,707,379 A | 1/1998 | Fleenor et al. |
| 5,709,693 A | 1/1998 | Taylor |
| 5,716,329 A | 2/1998 | Dieter |
| 5,720,757 A | 2/1998 | Hathaway et al. |
| 5,722,983 A | 3/1998 | Van Der Weegen |
| 5,728,109 A | 3/1998 | Schulze et al. |
| 5,738,629 A | 4/1998 | Moll et al. |
| 5,743,852 A | 4/1998 | Johnson |
| 5,746,753 A | 5/1998 | Sullivan et al. |
| 5,749,883 A | 5/1998 | Halpern |
| 5,759,188 A | 6/1998 | Yoon |
| 5,766,183 A | 6/1998 | Sauer |
| 5,766,220 A | 6/1998 | Moenning |
| 5,769,870 A | 6/1998 | Salahieh et al. |
| 5,779,719 A | 7/1998 | Klein et al. |
| 5,792,152 A | 8/1998 | Klein et al. |
| 5,792,153 A | 8/1998 | Swain et al. |
| 5,795,289 A | 8/1998 | Wyttenbach |
| 5,795,325 A | 8/1998 | Valley et al. |
| 5,797,948 A | 8/1998 | Dunham |
| 5,797,960 A | 8/1998 | Stevens et al. |
| 5,810,757 A | 9/1998 | Sweezer et al. |
| 5,810,849 A | 9/1998 | Kontos |
| 5,810,850 A | 9/1998 | Hathaway et al. |
| 5,817,108 A | 10/1998 | Poncet |
| 5,817,110 A | 10/1998 | Kronner |
| 5,820,631 A | 10/1998 | Nobles |
| 5,836,955 A | 11/1998 | Buelna et al. |
| 5,843,100 A | 12/1998 | Meade |
| 5,846,251 A | 12/1998 | Hart |
| 5,846,253 A | 12/1998 | Buelna et al. |
| 5,853,399 A | 12/1998 | Sasaki |
| 5,853,422 A | 12/1998 | Huebsch et al. |
| 5,855,585 A | 1/1999 | Kontos |
| 5,860,990 A | 1/1999 | Nobles et al. |
| 5,860,991 A | 1/1999 | Klein et al. |
| 5,860,992 A | 1/1999 | Daniel et al. |
| 5,860,997 A | 1/1999 | Bonutti |
| 5,861,003 A | 1/1999 | Latson et al. |
| 5,865,729 A | 2/1999 | Meehan et al. |
| 5,868,708 A | 2/1999 | Hart et al. |
| 5,868,762 A | 2/1999 | Cragg et al. |
| 5,871,320 A | 2/1999 | Kovac |
| 5,871,537 A | 2/1999 | Holman et al. |
| 5,876,411 A | 3/1999 | Kontos |
| 5,899,921 A | 5/1999 | Caspari et al. |
| 5,902,311 A | 5/1999 | Andreas et al. |
| 5,902,321 A | 5/1999 | Caspari et al. |
| 5,906,577 A | 5/1999 | Beane et al. |
| 5,908,428 A | 6/1999 | Scirica et al. |
| 5,919,200 A | 7/1999 | Stambaugh et al. |
| 5,919,208 A | 7/1999 | Valenti |
| 5,928,192 A | 7/1999 | Maahs |
| 5,931,844 A | 8/1999 | Thompson et al. |
| 5,935,098 A | 8/1999 | Blaisdell et al. |

(56) References Cited

U.S. PATENT DOCUMENTS

| | | |
|---|---|---|
| 5,935,149 A | 8/1999 | Ek |
| 5,944,730 A | 8/1999 | Nobles et al. |
| 5,951,588 A | 9/1999 | Moenning |
| 5,951,590 A | 9/1999 | Goldfarb |
| 5,954,732 A | 9/1999 | Hart et al. |
| 5,967,970 A | 10/1999 | Cowan et al. |
| 5,971,983 A | 10/1999 | Lesh |
| 5,972,005 A | 10/1999 | Stalker et al. |
| 5,980,539 A | 11/1999 | Kontos |
| 5,993,466 A | 11/1999 | Yoon |
| 5,997,555 A | 12/1999 | Kontos |
| 6,001,109 A | 12/1999 | Kontos |
| 6,004,337 A | 12/1999 | Kieturakis et al. |
| 6,010,530 A | 1/2000 | Goicoechea |
| 6,015,428 A | 1/2000 | Pagedas |
| 6,024,747 A | 2/2000 | Kontos |
| 6,033,430 A | 3/2000 | Bonutti |
| 6,036,699 A | 3/2000 | Andreas et al. |
| 6,059,800 A | 5/2000 | Hart et al. |
| 6,066,160 A | 5/2000 | Colvin et al. |
| 6,068,648 A | 5/2000 | Cole et al. |
| 6,071,271 A | 6/2000 | Baker et al. |
| 6,077,277 A | 6/2000 | Mollenauer et al. |
| 6,086,608 A | 7/2000 | Ek et al. |
| 6,099,553 A | 8/2000 | Hart et al. |
| 6,110,185 A | 8/2000 | Barra et al. |
| 6,113,580 A | 9/2000 | Dolisi |
| 6,117,144 A | 9/2000 | Nobles et al. |
| 6,126,677 A | 10/2000 | Ganaja et al. |
| 6,136,010 A | 10/2000 | Modesitt et al. |
| 6,143,015 A | 11/2000 | Nobles |
| 6,159,234 A | 12/2000 | Bonutti et al. |
| 6,171,319 B1 | 1/2001 | Nobles et al. |
| 6,174,324 B1 | 1/2001 | Egan et al. |
| 6,187,026 B1 | 2/2001 | Devlin et al. |
| 6,190,396 B1 | 2/2001 | Whitin et al. |
| 6,200,329 B1 | 3/2001 | Fung et al. |
| 6,203,565 B1 | 3/2001 | Bonutti et al. |
| 6,210,429 B1 | 4/2001 | Vardi et al. |
| 6,217,591 B1 | 4/2001 | Egan et al. |
| 6,241,699 B1 | 6/2001 | Suresh et al. |
| 6,245,079 B1 | 6/2001 | Nobles et al. |
| 6,245,080 B1 | 6/2001 | Levinson |
| 6,248,121 B1 | 6/2001 | Nobles |
| 6,280,460 B1 | 8/2001 | Bolduc et al. |
| 6,290,674 B1 | 9/2001 | Roue et al. |
| 6,332,889 B1 | 12/2001 | Sancoff et al. |
| 6,348,059 B1 | 2/2002 | Hathaway et al. |
| 6,352,543 B1 | 3/2002 | Cole et al. |
| 6,383,208 B1 | 5/2002 | Sancoff et al. |
| 6,395,015 B1 | 5/2002 | Borst et al. |
| 6,409,739 B1 | 6/2002 | Nobles et al. |
| 6,432,115 B1 | 8/2002 | Mollenauer et al. |
| 6,468,293 B2 | 10/2002 | Bonutti et al. |
| 6,508,777 B1 | 1/2003 | Macoviak et al. |
| 6,527,785 B2 | 3/2003 | Sancoff et al. |
| 6,533,795 B1 | 3/2003 | Tran et al. |
| 6,537,299 B1 | 3/2003 | Hogendijk et al. |
| 6,547,725 B1 | 4/2003 | Paolitto et al. |
| 6,547,760 B1 | 4/2003 | Samson et al. |
| 6,551,331 B2 | 4/2003 | Nobles et al. |
| 6,562,052 B2 | 5/2003 | Nobles et al. |
| 6,585,689 B1 | 7/2003 | Macoviak et al. |
| 6,663,643 B2 | 12/2003 | Field et al. |
| 6,679,895 B1 | 1/2004 | Sancoff et al. |
| 6,682,540 B1 | 1/2004 | Sancoff et al. |
| 6,716,243 B1 | 4/2004 | Colvin et al. |
| 6,726,651 B1 | 4/2004 | Robinson et al. |
| 6,733,509 B2 | 5/2004 | Nobles et al. |
| 6,767,352 B2 | 7/2004 | Field et al. |
| 6,770,076 B2 | 8/2004 | Foerster |
| 6,770,084 B1 | 8/2004 | Bain et al. |
| 6,786,913 B1 | 9/2004 | Sancoff |
| 6,978,176 B2 | 1/2005 | Lattouf |
| 6,855,157 B2 | 2/2005 | Foerster et al. |
| 6,893,448 B2 | 5/2005 | O'Quinn et al. |
| 6,911,034 B2 | 6/2005 | Nobles et al. |
| 6,913,600 B2 | 7/2005 | Valley et al. |
| 6,936,057 B1 | 8/2005 | Nobles |
| 7,004,952 B2 | 2/2006 | Nobles et al. |
| 7,083,630 B2 | 8/2006 | DeVries et al. |
| 7,083,638 B2 | 8/2006 | Foerster |
| 7,090,686 B2 | 8/2006 | Nobles et al. |
| 7,090,690 B2 | 8/2006 | Foerster et al. |
| 7,118,583 B2 | 10/2006 | O'Quinn et al. |
| 7,160,309 B2 | 1/2007 | Voss |
| 7,172,595 B1 | 2/2007 | Goble |
| 7,220,266 B2 | 5/2007 | Gambale |
| 7,232,446 B1 | 6/2007 | Farris |
| 7,235,086 B2 | 6/2007 | Sauer et al. |
| 7,326,221 B2 | 2/2008 | Sakamoto et al. |
| 7,329,272 B2 | 2/2008 | Burkhart et al. |
| 7,338,502 B2 | 3/2008 | Rosenblatt |
| 7,381,210 B2 | 6/2008 | Zarbatany et al. |
| 7,399,304 B2 | 7/2008 | Gambale et al. |
| 7,435,251 B2 | 10/2008 | Green |
| 7,449,024 B2 | 11/2008 | Stafford |
| 7,491,217 B1 | 2/2009 | Hendren |
| 7,601,161 B1 | 10/2009 | Nobles et al. |
| 7,628,797 B2 | 12/2009 | Tieu et al. |
| 7,635,386 B1 | 12/2009 | Gammie |
| 7,637,926 B2 | 12/2009 | Foerster et al. |
| 7,722,629 B2 | 5/2010 | Chambers |
| 7,803,167 B2 | 9/2010 | Nobles et al. |
| 7,842,051 B2 | 11/2010 | Dana et al. |
| 7,846,181 B2 | 12/2010 | Schwartz et al. |
| 7,879,072 B2 | 2/2011 | Bonutti et al. |
| 7,905,892 B2 | 3/2011 | Nobles et al. |
| 7,918,867 B2 | 4/2011 | Dana et al. |
| 7,931,641 B2 | 4/2011 | Chang et al. |
| 7,993,368 B2 | 8/2011 | Gambale et al. |
| 8,075,573 B2 | 12/2011 | Gambale et al. |
| 8,083,754 B2 | 12/2011 | Pantages et al. |
| 8,105,355 B2 | 1/2012 | Page et al. |
| 8,197,497 B2 | 6/2012 | Nobles et al. |
| 8,202,281 B2 | 6/2012 | Voss |
| 8,246,636 B2 | 8/2012 | Nobles et al. |
| 8,252,005 B2 | 8/2012 | Findlay, III et al. |
| 8,282,659 B2 | 10/2012 | Oren et al. |
| 8,287,556 B2 | 10/2012 | Gilkey et al. |
| 8,298,291 B2 | 10/2012 | Ewers et al. |
| 8,303,622 B2 | 11/2012 | Alkhatib |
| 8,348,962 B2 | 1/2013 | Nobles et al. |
| 8,372,089 B2 | 2/2013 | Nobles et al. |
| 8,398,676 B2 | 3/2013 | Roorda et al. |
| 8,430,893 B2 | 4/2013 | Ma |
| 8,469,975 B2 | 6/2013 | Nobles et al. |
| 8,496,676 B2 | 7/2013 | Nobles et al. |
| 8,500,776 B2 | 8/2013 | Ebner |
| 8,540,736 B2 * | 9/2013 | Gaynor ............... A61B 17/0469 606/146 |
| 8,568,427 B2 | 10/2013 | Nobles et al. |
| 8,623,036 B2 | 1/2014 | Harrison et al. |
| 8,728,105 B2 | 5/2014 | Aguirre |
| 8,758,370 B2 | 6/2014 | Shikhman et al. |
| 8,771,296 B2 | 7/2014 | Nobles et al. |
| 9,131,938 B2 * | 9/2015 | Nobles ............... A61B 17/0057 |
| 9,326,764 B2 | 5/2016 | Nobles et al. |
| 9,332,976 B2 | 5/2016 | Yribarren |
| 9,364,238 B2 | 6/2016 | Bakos et al. |
| 9,398,907 B2 | 7/2016 | Nobles et al. |
| 9,402,605 B2 | 8/2016 | Viola |
| 9,649,106 B2 | 5/2017 | Nobles et al. |
| 9,706,988 B2 | 7/2017 | Nobles et al. |
| 10,285,687 B2 | 5/2019 | Nobles et al. |
| 10,420,545 B2 | 9/2019 | Nobles et al. |
| 10,512,458 B2 | 12/2019 | Nobles |
| 2001/0031973 A1 | 10/2001 | Nobles et al. |
| 2002/0013601 A1 | 1/2002 | Nobles et al. |
| 2002/0045908 A1 | 4/2002 | Nobles et al. |
| 2002/0049453 A1 | 4/2002 | Nobles et al. |
| 2002/0096183 A1 | 7/2002 | Stevens et al. |
| 2002/0128598 A1 | 9/2002 | Nobles |
| 2002/0169475 A1 | 11/2002 | Gainor et al. |

(56) References Cited

U.S. PATENT DOCUMENTS

| | | |
|---|---|---|
| 2002/0183787 A1 | 12/2002 | Wahr et al. |
| 2003/0078601 A1 | 4/2003 | Skikhman et al. |
| 2003/0114863 A1 | 6/2003 | Field et al. |
| 2003/0144673 A1 | 7/2003 | Onuki et al. |
| 2003/0204205 A1 | 10/2003 | Sauer et al. |
| 2003/0208209 A1 | 11/2003 | Gambale et al. |
| 2003/0220667 A1 | 11/2003 | van der Burg et al. |
| 2004/0015177 A1 | 1/2004 | Chu |
| 2004/0044365 A1 | 3/2004 | Bachman |
| 2004/0059351 A1 | 3/2004 | Eigler et al. |
| 2004/0102797 A1 | 5/2004 | Golden et al. |
| 2004/0153116 A1 | 8/2004 | Nobles |
| 2004/0236356 A1 | 11/2004 | Rioux et al. |
| 2004/0260298 A1 | 12/2004 | Kaiseer et al. |
| 2005/0033361 A1 | 2/2005 | Galdonik et al. |
| 2005/0070923 A1 | 3/2005 | McIntosh |
| 2005/0149066 A1 | 7/2005 | Stafford |
| 2005/0187575 A1 | 8/2005 | Hallbeck et al. |
| 2005/0203564 A1 | 9/2005 | Nobles |
| 2005/0228407 A1 | 10/2005 | Nobles et al. |
| 2005/0261708 A1 | 11/2005 | Pasricha et al. |
| 2005/0261710 A1 | 11/2005 | Sakamoto et al. |
| 2005/0277986 A1 | 12/2005 | Foerster et al. |
| 2006/0052813 A1 | 3/2006 | Nobles |
| 2006/0064113 A1 | 3/2006 | Nakao |
| 2006/0064115 A1 | 3/2006 | Allen et al. |
| 2006/0069397 A1 | 3/2006 | Nobles et al. |
| 2006/0074484 A1 | 4/2006 | Huber |
| 2006/0095052 A1 | 5/2006 | Chambers |
| 2006/0195120 A1 | 8/2006 | Nobles et al. |
| 2006/0248691 A1 | 11/2006 | Rosemann |
| 2006/0265010 A1 | 11/2006 | Paraschac et al. |
| 2006/0282088 A1 | 12/2006 | Ryan |
| 2006/0282094 A1 | 12/2006 | Stokes et al. |
| 2006/0282102 A1 | 12/2006 | Nobles et al. |
| 2006/0287657 A1 | 12/2006 | Bachman |
| 2007/0005079 A1 | 1/2007 | Zarbatany et al. |
| 2007/0010829 A1 | 1/2007 | Nobles et al. |
| 2007/0043385 A1 | 2/2007 | Nobles et al. |
| 2007/0060930 A1 | 3/2007 | Hamilton et al. |
| 2007/0106310 A1 | 5/2007 | Goldin et al. |
| 2007/0118151 A1 | 5/2007 | Davidson |
| 2007/0142846 A1 | 6/2007 | Catanese, III et al. |
| 2007/0213757 A1 | 9/2007 | Boraiah |
| 2007/0219630 A1 | 9/2007 | Chu |
| 2007/0276413 A1 | 11/2007 | Nobles |
| 2007/0276414 A1 | 11/2007 | Nobles |
| 2008/0033459 A1 | 2/2008 | Shafi et al. |
| 2008/0065145 A1 | 3/2008 | Carpenter |
| 2008/0077162 A1 | 3/2008 | Domingo |
| 2008/0114384 A1 | 5/2008 | Chang et al. |
| 2008/0188873 A1 | 8/2008 | Speziali |
| 2008/0228201 A1 | 9/2008 | Zarbatany |
| 2008/0269786 A1 | 10/2008 | Nobles et al. |
| 2008/0269788 A1 | 10/2008 | Phillips |
| 2009/0036906 A1 | 2/2009 | Stafford |
| 2009/0048615 A1 | 2/2009 | McIntosh |
| 2009/0099410 A1 | 4/2009 | De Marchena |
| 2009/0105729 A1 | 4/2009 | Zentgraf |
| 2009/0105751 A1 | 4/2009 | Zentgraf |
| 2009/0118726 A1 | 5/2009 | Auth et al. |
| 2009/0125042 A1 | 5/2009 | Mouw |
| 2009/0287183 A1 | 11/2009 | Bishop et al. |
| 2009/0299409 A1 | 12/2009 | Coe et al. |
| 2009/0312772 A1 | 12/2009 | Chu |
| 2009/0312783 A1 | 12/2009 | Whayne et al. |
| 2009/0312789 A1 | 12/2009 | Kassab et al. |
| 2010/0016870 A1 | 1/2010 | Campbell |
| 2010/0030242 A1 | 2/2010 | Nobles et al. |
| 2010/0042147 A1 | 2/2010 | Janovsky et al. |
| 2010/0063586 A1 | 3/2010 | Hasenkam et al. |
| 2010/0087838 A1 | 4/2010 | Nobles et al. |
| 2010/0094314 A1 | 4/2010 | Hernlund et al. |
| 2010/0100167 A1 | 4/2010 | Bortlein et al. |
| 2010/0179585 A1 | 7/2010 | Carpenter et al. |
| 2010/0210899 A1 | 8/2010 | Schankereli |
| 2011/0190793 A1 | 8/2011 | Nobles et al. |
| 2011/0202077 A1 | 8/2011 | Chin et al. |
| 2011/0224720 A1 | 9/2011 | Kassab et al. |
| 2011/0251627 A1 | 10/2011 | Hamilton et al. |
| 2012/0016384 A1 | 1/2012 | Wilke et al. |
| 2012/0035628 A1 | 2/2012 | Aguirre et al. |
| 2012/0059398 A1 | 3/2012 | Pate et al. |
| 2012/0143222 A1 | 6/2012 | Dravis et al. |
| 2012/0165838 A1 | 6/2012 | Kobylewski et al. |
| 2012/0296373 A1 | 11/2012 | Roorda et al. |
| 2013/0103056 A1 | 4/2013 | Chu |
| 2013/0261645 A1 | 10/2013 | Nobles et al. |
| 2013/0324800 A1 | 12/2013 | Cahill |
| 2014/0309670 A1 | 10/2014 | Bakos et al. |
| 2014/0379006 A1 | 12/2014 | Sutherland et al. |
| 2015/0374351 A1 | 9/2015 | Nobles et al. |
| 2015/0359531 A1 | 12/2015 | Sauer |
| 2016/0007998 A1 | 1/2016 | Nobles et al. |
| 2016/0151064 A1 | 6/2016 | Nobles |
| 2016/0302787 A1 | 10/2016 | Nobles |
| 2017/0035425 A1 | 2/2017 | Fegelman et al. |
| 2017/0042534 A1 | 2/2017 | Nobles |
| 2017/0049451 A1 | 2/2017 | Hausen |
| 2017/0296168 A1 | 4/2017 | Nobles et al. |
| 2017/0128059 A1 | 5/2017 | Coe et al. |
| 2017/0245853 A1 | 8/2017 | Nobles |
| 2017/0303915 A1 | 10/2017 | Nobles |
| 2019/0239880 A1 | 8/2019 | Nobles |

FOREIGN PATENT DOCUMENTS

| | | |
|---|---|---|
| CN | 101257852 | 8/2011 |
| DE | 29 01 701 | 7/1980 |
| EP | 0 241 038 | 10/1987 |
| EP | 0 544 485 | 6/1993 |
| EP | 0839 550 | 5/1998 |
| EP | 0 894 475 | 2/1999 |
| EP | 0 983 027 | 12/2005 |
| EP | 1 852 071 | 11/2007 |
| EP | 1 987 779 | 11/2008 |
| EP | 2 572 649 | 3/2013 |
| FR | 2 701 401 | 8/1994 |
| JP | A 9507398 | 7/1997 |
| JP | 09-266910 A | 10/1997 |
| JP | H10-43192 | 2/1998 |
| JP | 2001-524864 | 12/2001 |
| JP | 2003-139113 A2 | 5/2003 |
| JP | 2003-225241 A | 8/2003 |
| JP | 2007-503870 | 3/2007 |
| JP | 2008-514305 | 5/2008 |
| JP | 2008-541857 | 11/2008 |
| JP | 2008-546454 | 12/2008 |
| JP | 2010-522625 | 7/2010 |
| JP | 2011-067251 | 4/2011 |
| RU | 2010 125954 | 1/2012 |
| SU | 1560129 A1 | 4/1990 |
| WO | WO 92/05828 | 4/1992 |
| WO | WO 93/01750 | 2/1993 |
| WO | WO 93/07800 | 4/1993 |
| WO | WO 95/12429 | 5/1995 |
| WO | WO 95/17127 | 6/1995 |
| WO | WO 95/25468 | 9/1995 |
| WO | WO 95/25470 | 9/1995 |
| WO | WO 96/03083 | 2/1996 |
| WO | WO 96/29012 | 9/1996 |
| WO | WO 96/40347 | 12/1996 |
| WO | WO 97/03613 | 2/1997 |
| WO | WO 97/47261 | 2/1997 |
| WO | WO 97/07745 | 3/1997 |
| WO | WO 97/12540 | 4/1997 |
| WO | WO 97/20505 | 6/1997 |
| WO | WO 97/24975 | 7/1997 |
| WO | WO 97/27807 | 8/1997 |
| WO | WO 97/40738 | 11/1997 |
| WO | WO 98/12970 | 4/1998 |
| WO | WO 98/52476 | 11/1998 |
| WO | WO 99/40851 | 8/1999 |
| WO | WO 99/42160 | 8/1999 |

(56) References Cited

FOREIGN PATENT DOCUMENTS

| WO | WO 99/45848 | 9/1999 |
|---|---|---|
| WO | WO 00/002489 | 1/2000 |
| WO | WO 01/001868 | 1/2001 |
| WO | WO 01/95809 | 12/2001 |
| WO | WO 02/024078 | 3/2002 |
| WO | WO 04/012789 | 2/2004 |
| WO | WO 04/096013 | 11/2004 |
| WO | WO 06/127636 | 11/2006 |
| WO | WO 07/001936 | 1/2007 |
| WO | WO 07/016261 | 2/2007 |
| WO | WO 09/081396 | 7/2009 |
| WO | WO 11/137224 | 11/2011 |
| WO | WO 2011/156782 | 12/2011 |
| WO | WO 2012/012336 | 1/2012 |
| WO | WO 13/027209 | 2/2013 |
| WO | WO 2013/142487 | 9/2013 |
| WO | WO 17/180092 | 10/2017 |
| WO | WO 2019/035095 | 2/2019 |
| WO | WO 2019/051379 | 3/2019 |
| WO | WO 2019/055433 | 3/2019 |

OTHER PUBLICATIONS

Advances in Vascular Surgery, by John S. Najarian, M.D. and John P. Delaney, M.D., copyright 1983 by Year Book Publishers, Inc. at pp. 94,95,96, and 224.

Cardio Medical Solutions, Inc. brochure titled: "Baladi Inverter for Clamp less Surgery"—Undated.

Clinical Evaluation of Arteriovenous Fistulas as an Adjunct to Lower Extremity Arterial Reconstructions, by Herbert Dardick, M.D., in Current Critical Problems in Vascular Surgery, copyright 1989 by Quality Medical Publishing Inc., at p. 383.

Current Therapy in Vascular Surgery, 2nd edition, by Calvin B. Ernst, M.D. and James C. Stanley, M.D., copyright 1991 by B.C. Decker, Inc., at pp. A and 140.

Eskuri, A., The Design of a Minimally Invasive Vascular Suturing Device, Thesis submitted to Rose-Hulman Institute of Technology, Nov. 1999.

Manual of Vascular Surgery, vol. 2, Edwin J. Wylie, Ronald J. Stoney, William K. Ehrenfeld and David J. Effeney (Richard H. Egdahl ed.), copyright 1986 by Springer-Verlag New York Inc., at p. 41.

Nursing the Open-Heart Surgery Patient, By Mary Jo Aspinall, R.N., M.N., copyright 1973 by McGraw Hill, Inc., at pp. 216 and 231.

Operative Arterial Surgery, by P.R. Bell, M.D., and W Barrie, M.D., copyright 1981 by Bell, Barrie, and Leicester Royal Infirmary, printed byJohn Wright &Sons, pp. 16, 17, 104, 105, 112, and 113.

Sinus Venous Type of Atrial Septal Defect with Partial Anomalous Pulmonary Venous Return, by Francis Robicsek, MD., et ai, in Journal of Thoracic and Cardiovascular Surgery, Oct. 1979, vol. 78, No. 4, at pp. 559-562.

*Sutura, Inc.* v. *Abbott Laboratories, et al.* Civil Action No. 2:06CV-536 (TJW), Sworn Declaration of Dr. John R. Crew, M.D., Dated Sep. 4, 2001.

Techniques in Vascular Surgery, by Denton A. Cooley, MD. and Don C. Wukasch, MD., copyright 1979 by WB. Saunders Co., at pp. 38,57,86,134,156, and 184.

The problem: Closing wounds in deep areas during laparoscopic operations The solution: REMA Medizintechnik GmbH (no date).

Vascular Access, Principles and Practice, 3rd edition, by Samuel Eric Wilson, MD., copyright 1996, 1988, 1980 by Mosby-Year Book, Inc., pp. 89 and 159.

Vascular and Endovascular Surgery, by Jonathan D. Beard and Peter Gainers, copyright 1998 by W.B. Saunders Co., Ltd, p. 414.

Vascular Surgery, 3rd edition, vol. 1, by Robert B. Rutherford, MD., copyright 1989, 1984, 1976 by W.B.SaundersCo., at pp. 347, 348, 354, 594, 607, 622, 675, 677, 680, 698, 700, 721, 727, 735, and 829.

Vascular Surgery, 4th edition by Robert B. Rutherford, MD., copyright 1995, 1989, 1976, by W.B. Saunders Co., vol. 1, at pp. 400-404, 661, and A.

Vascular Surgery, 4th edition, by Robert B. Rutherford, M.D., copyright 1995, 1989, 1984, 1976 by W.B. Saunders Co., vol. 2, at pp. 1318, 1363, 1426, 1564, and 1580.

Vascular Surgery, by Robert B. Rutherford, M.D. copyright1977 by WB. Saunders Co., at pp. 334 and 817.

International Preliminary Report on Patentability, dated Oct. 16, 2018 for International Application No. PCT/US2016/026965, in 9 pages.

International Search Report and Written Opinion in corresponding International Patent Application No. PCT/US2016/026965, dated Jul. 7, 2016, in 11 pages.

U.S. Appl. No. 16/576,253, filed Sep. 19, 2019, Nobles et al.

European Extended Search Report for European Applicaton No. 16898790.7, dated Sep. 6, 2019.

* cited by examiner

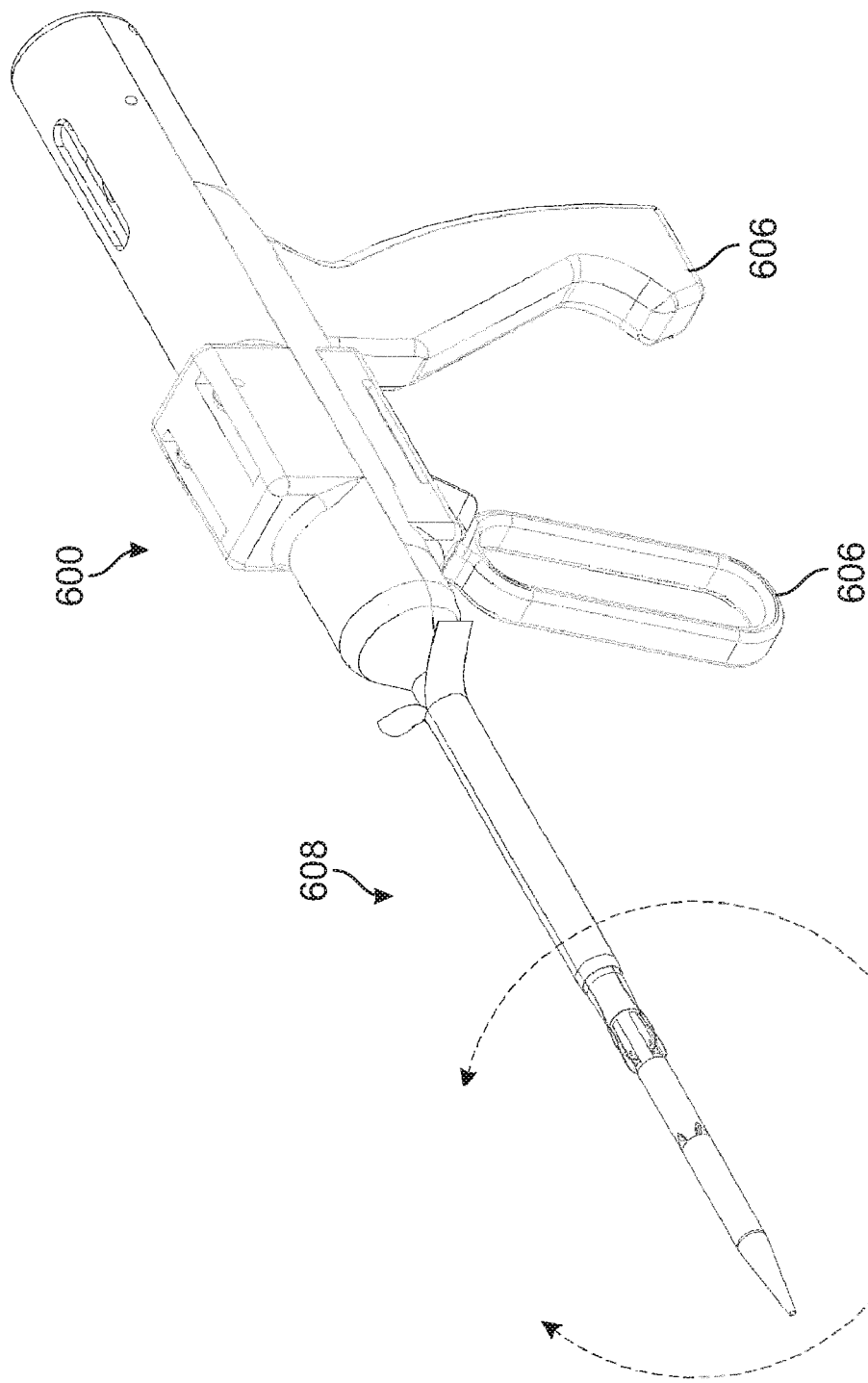

SUTURE SPOOLS FOR TISSUE SUTURING DEVICE

BACKGROUND

Field

Embodiments of the disclosure relate generally to suturing devices and methods of use for suturing biological tissue such as at openings in the heart, blood vessels and other locations.

Description of the Related Art

Health practitioners frequently use sutures to close various openings such as cuts, punctures, and incisions in various places in the human body. Generally, sutures are convenient to use and function properly to hold openings in biological tissue closed thereby aiding in blood clotting, healing, and prevention of scaring. Sutures are also advantageous to use and function properly to hold openings in biological tissue closed thereby aiding in blood clotting, healing, and prevention of scaring.

For example, sutures may be used to close openings made into blood vessels where the openings are utilized to provide access to another location in the body during a transcatheter procedure. Sutures may also be utilized to close openings within the human body, such as natural, abnormal or man-made openings in the heart. Examples of such openings include septal defects, a patent foramen ovale (PFO), heart valves (e.g., the mitral valve, aortic valve, tricuspid valve and pulmonary valve), and openings made in the apex of the heart (transapical openings) used to gain access to the left ventricular of the heart. Examples of devices and methods to perform such procedures can be found in U.S. Pat. No. 9,131,938, filed Feb. 7, 2013, U.S. Pat. No. 8,246,636, filed Mar. 27, 2008, U.S. Pat. No. 8,771,296, filed May 8, 2009, U.S. Pat. No. 6,117,144, filed Jan. 14, 1999, Int'l. Pub. App. No. WO 2012/142338, filed Apr. 12, 2012, Int'l. Pub. App. No. WO 2013/170081, filed May 9, 2013, Int'l. Pub. App. No. WO 2011/094619, filed Jan. 28, 2011, and U.S. Pat. Pub. No. 2014/0303657, filed Jan. 23, 2015, each of which is hereby incorporated by reference in its entirety.

With regards to anatomical valves, including but not limited to the heart valves mentioned above, some heart valves may be weakened or stretched, or may have other structural defects, such as congenital defects, that cause them to close improperly, which can lead to blood flow contrary to the normal flow direction. This condition, referred to as regurgitation, incompetence, or insufficiency, can reduce blood flow in the normal direction. Regurgitation causes the heart to work harder to compensate for backflow of blood through these valves, which can lead to enlargement of the heart that reduces cardiac performance. While the tricuspid valve and the pulmonary valve may present these conditions, the mitral valve and aortic valve more frequently demonstrate these conditions.

With regards to closures of a heart, during development of a fetus in utero, blood is generally oxygenated by the mother's placenta, not the fetus' developing lungs. Most of the fetus' circulation is shunted away from the lungs through specialized vessels or foramens, such as the foramen ovale. The foramen ovale is a flaplike opening between the atrial septa primum and secundum which serves as a physiologic conduit for right to left shunting between the atria. Typically, once the pulmonary circulation is established after birth, left atrial pressure increases, resulting in the fusing of the septum primum and septum secundum and thus the closure of the foramen ovale. Occasionally, however, these foramen fail to close and create hemodynamic problems, which may ultimately prove fatal unless treated. A foramen ovale which does not seal is defined a patent foramen ovale, or PFO.

When sutures are used to close any of the body openings described above or when closing other biological tissue, it can become difficult when the sutures extend outside of a suturing device, for example alongside a handle. It becomes very difficult to keep the sutures organized and to track the particular suture when multiple sutures are used. Further, the sutures can easily be tangled outside of the device.

SUMMARY

Certain embodiments of the present disclosure are directed to devices for suturing biological tissue and/or closing openings in the body. Further embodiments are directed to methods of suturing tissue, such as through the use of one or more such devices.

Disclosed herein are embodiments of a device for suturing biological tissue, the device comprising an elongate body having a proximal end and a distal end, at least one arm extendible from the elongate body, the at least one arm configured to move between a retracted position wherein the at least one arm is within the elongate body and a deployed position wherein the at least one arm extends away from the elongate body, the at least one arm configured to hold a first portion of a suture, at least one needle moveable relative to the elongate body between a retracted position and a deployed position, wherein the at least one needle when moving from its retracted position to its deployed position is configured to pass through tissue and capture the suture first portion held by the at least one arm, and is further configured to move from the deployed position to the retracted position to bring the suture first portion through the tissue, a handle located at the proximal end of the elongate body, the handle having one or more actuators configured to cause movement of the at least one arm and the at least one needle, and at least one suture spool mountable in fixed relationship to and located external to the elongate body and the handle, the at least one suture spool configured to retain a second portion of the suture, wherein, when the suture first portion is captured by the at least one needle and the at least one needle brings the suture first portion through the tissue, the at least one suture spool is configured such that the at least one suture unwinds from the at least one suture spool.

In some embodiments, the at least one suture spool can comprise an aperture, wherein the suture unwinds through the aperture. In some embodiments, the at least one suture spool can comprise an inner circumference around which the suture winds.

In some embodiments, the at least one spool can comprise a cylindrical portion having an open proximal end, an aperture located on a distal end, and a conical portion between the cylindrical portion and the aperture. In some embodiments, the at least one suture spool can be mountable between the handle and the at least one arm. In some embodiments, the at least one spool can be mountable around the elongate body such that the at least one spool is offset to one side of a longitudinal axis of the elongate body. In some embodiments, the at least one spool can be attachable to a Y-connector positioned around the elongate body.

In some embodiments, the device can comprise at least two spools mounted around the elongate body, the at least two spools corresponding to two arms extendible from the elongate body and two needles configured to capture sutures held by the two arms. In some embodiments, the device can comprise four spools mounted around the elongate body, the four spools corresponding to four arms extendible from the elongate body and four needles configured to capture sutures held by the four arms.

In some embodiments, the at least one suture spool can be mounted in fixed relationship to and located external to the elongate body and the handle, and the at least one suture spool contains a suture wound thereon that extends to the at least one arm.

In some embodiments, the at least one needle can move distally to proximally when moving from the retracted position to the deployed position. In some embodiments, the at least one needle can move proximally to distally when moving from the retracted position to the deployed position.

In some embodiments, the at least one arm can be located at or near the distal end of the elongate body. In some embodiments, the device can further comprise an outer sheath located over the elongate body, wherein the at least one suture is configured to extend from the at least one suture spool between the outer sheath and the elongate body to the at least one arm. In some embodiments, the outer sheath can comprise a peelable outer sheath.

Also disclosed herein are embodiments of a device for suturing a body opening such as a patent foramen ovale (PFO), the device comprising an elongate body having a proximal end and a distal end, at least one arm extendible from the elongate body, the at least one arm configured to move between a retracted position wherein the at least one arm is within the elongate body and a deployed position wherein the at least one arm extends away from the elongate body, the at least one arm configured to hold a first portion of a suture, at least one needle moveable relative to the elongate body between a retracted position and a deployed position, wherein the at least one needle when moving from its retracted position to its deployed position is configured to pass through tissue and capture the suture first portion held by the at least one arm, and is further configured to move from the deployed position to the retracted position to bring the suture first portion through the tissue, a handle located at the proximal end of the elongate body, the handle having a first actuator configured to cause movement of the at least one arm and a second actuator configured to cause movement of the at least one needle, and at least one suture spool mounted around the elongate body between the handle and the at least one arm, the at least one suture spool configured to retain a second portion of the suture, wherein, when the suture first portion is captured by the at least one needle and the at least one needle brings the suture first portion through the tissue, the at least one suture spool is configured such that the at least one suture unwinds from the at least one suture spool.

In some embodiments, the at least one suture spool can be mounted around the elongate body with a Y-connector mounted on the elongate body. In some embodiments, the device can further comprise a suture wound on the at least one suture spool, the suture extending from the suture spool through an interior of the elongate body to the at least one arm. In some embodiments, the device can comprise a single arm and a single needle. In some embodiments, the arm can be proximal to the needle. In some embodiments, the arm can be distal to the needle.

Also disclosed herein are embodiments of a suturing device for suturing a body opening such as a transapical opening in the heart, the device comprising an elongate body having a proximal end and a distal end, four arms extendible from the elongate body, the four arms configured to move between a retracted position wherein each of the four arms is within the elongate body and a deployed position wherein the each of the four arms extends away from the elongate body, each of the four arms configured to hold a first portion of each of four sutures, four needles moveable relative to the elongate body between a retracted position and a deployed position, wherein each of the four needles when moving from its retracted position to its deployed position is configured to pass through tissue and capture the suture first portion held by each of the four arms, and is further configured to move from the deployed position to the retracted position to bring each of the suture first portions through the tissue, a handle located at the proximal end of the elongate body, the handle having at least a first actuator configured to cause movement of each of the four arms and at least a second actuator configured to cause movement of each of the four needles, and four suture spools mounted around the elongate body between the handle and the four arms, each of the four suture spools configured to retain a second portion of each of the four sutures, and a peel-away sheath at least partially surrounding the elongate body, each of the four sutures configured to extend from the four suture spools through the peel-away sheath to the four arms, wherein, when each of the first portions of the four sutures is captured by each of the four needles and each of the four needles brings each of the suture first portions through the tissue, the four suture spools are configured such that each of the four sutures unwinds from each of the four suture spools.

In some embodiments, the device can further comprise a guide piece located distal to the four suture spools and proximal to the peel-away sheath, the guide piece having four apertures, wherein each of the four sutures extends through one of the four apertures.

Further disclosed herein are embodiments of a method of suturing biological tissue, comprising using a suturing device as described herein to close a body opening. In some embodiments, the suturing device can be used to close a patent foramen ovale. In some embodiments, the method can comprise using two separate suturing devices close the patent foramen ovale. In some embodiments, the suturing device can be used to close an opening in the heart.

BRIEF DESCRIPTION OF THE DRAWINGS

FIGS. 6A-B illustrate an embodiment of a multi-armed suturing device.

DETAILED DESCRIPTION

Embodiments of suturing devices and methods for suturing biological tissue are disclosed herein. The suturing devices and their methods of use can be useful in a variety of procedures, such as treating (e.g., closing) wounds and naturally or surgically created apertures or passageways. Specifically, embodiments of the disclosed the suturing devices can be used to close or reduce a variety of other tissue openings, lumens, hollow organs or natural or surgically created passageways in the body. In some embodiments, the suturing devices can be used to suture prosthetics, synthetic materials, or implantable devices in the body. For example, the devices can be used to suture a pledget within the body.

In some embodiments, the disclosed devices can be used to place sutures to close an opening into a heart, although they are not limited to applications within a heart. In some embodiments, the opening is a puncture made at or near the apex of the heart. The puncture can also be made at other areas of the heart. The heart can be accessed through a sternotomy or limited thoracotomy, or alternatively the device can pass through a trocar or other element into the thoracic cavity and then be led toward the puncture in the heart, typically by following a guide wire.

While not limited to particular example embodiments of suturing devices are disclosed herein, embodiments of the disclosure can be incorporated into any number of suturing devices. For example, embodiments of the disclosure can be incorporated into the devices disclosed in U.S. Pat. No. 9,131,938, filed Feb. 7, 2013, U.S. Pat. No. 8,246,636, filed Mar. 27, 2008, U.S. Pat. No. 8,771,296, filed May 8, 2009, U.S. Pat. No. 6,117,144, filed Jan. 14, 1999, Int'l. Pub. No. WO 2012/142338, filed Apr. 12, 2012, Int'l. Pub. No. WO 2013/170081, filed May 9, 2013, Int'l. Pub. No. WO 2011/094619, filed Jan. 28, 2011, and U.S. Pat. Pub. No. 2014/0303657, filed Jan. 23, 2015, each of which is hereby incorporated by reference in its entirety. Features and procedures described in the aforementioned publications can be incorporated into the embodiments described herein.

Dual Device System

Figure 1:
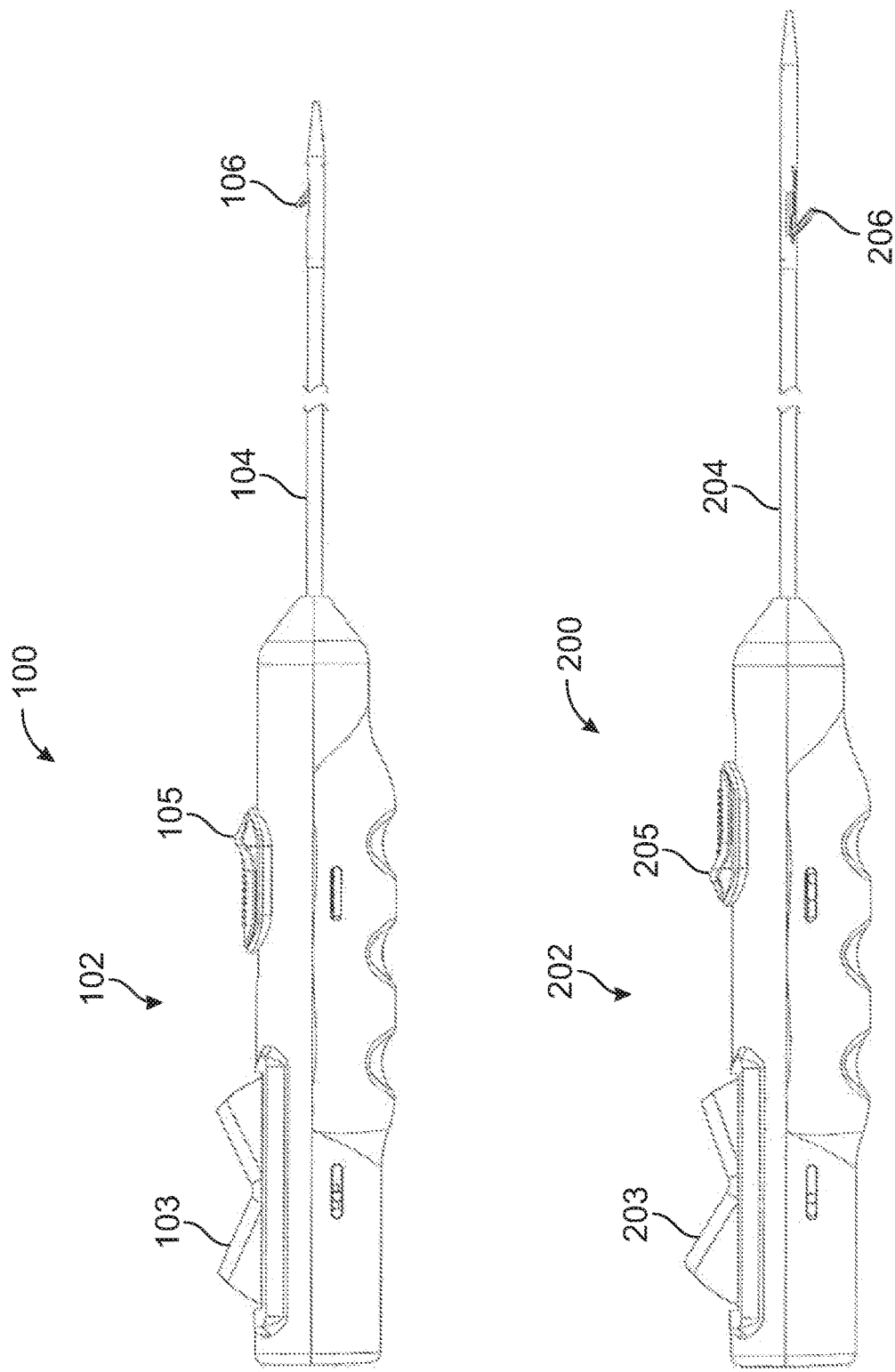
FIG. 1 shows a side view of an embodiment of a system of suturing devices.

FIG. 1 shows a pair of suturing devices 100 and 200 for suturing an opening in a vessel wall (such as a heart wall) or other biological tissue. While the devices will be described in reference to suturing an opening in a heart wall, such as a patent foramen ovale (PFO), one or both of the devices 100/200, could be used to close other openings in the heart wall, such as a patent ductus arteriosus (PDA) or an atrial septal defect (ASD), other openings in bodily tissue, or the like. The devices 100/200 could also be used to suture adjacent biological structures or any other time it may be desired to apply a suture to a biological structure, or to perform other procedures.

As shown, the suturing device 100 can have a handle 102 at the proximal end of the suturing device 100. The handle 102 can include any number of knobs/actuators/switches/buttons 103/105 that can control functionality of the suturing device 100 as discussed in detail below. For example, switch 103 can control the arm of the device 100 and switch 105 can control the movement of the needle, the motion of both discussed in detail below.

The suturing device 100 includes an elongate body 104 (e.g., elongate tubular member, elongate member) having a proximal end that can be connected to the handle 102 and a distal end of which can be used for positioning at the biological tissue to be sutured, such as in the opening of the PFO. The elongate body 104 can include one or more elongate members between the handle 102 and the distal end of the assembly (e.g., attached end to end or an elongate body within the lumen of another elongate body). The axial length and flexibility of the elongated tubular member 104 can be sufficient to percutaneously access the patient's vasculature and advance the elongate body 104 through the venous system to the patient's heart with the proximal end of the device remaining outside the patient's body. The distal end of the elongate body 104 can also include a suture clasp arm 106, which can be used for retaining a suture for closure of a PFO. The suture clasp arm 106 can rotate between a retracted position, wherein the suture clasp arm 106 is located in the elongate body 104 or generally parallel to it, to a deployed position where the suture clasp arm 106 extends away from the elongate body 104.

Suturing device 200 can be similar to suturing device 100, and can contain essentially the same components as shown in FIG. 1, such as the handle 202, actuators 203/205, elongate body 204, and suture clasp arm 206. However, there may be modifications between the suturing device 200 and suturing device 100. For example, the devices 100/200 may have different lengths of the elongate bodies 104/204, though in some embodiments they may be the same length. Further, the suture clasp arms 204/206 may extend in different directions upon deployment, as discussed in detail below.

Figure 2:
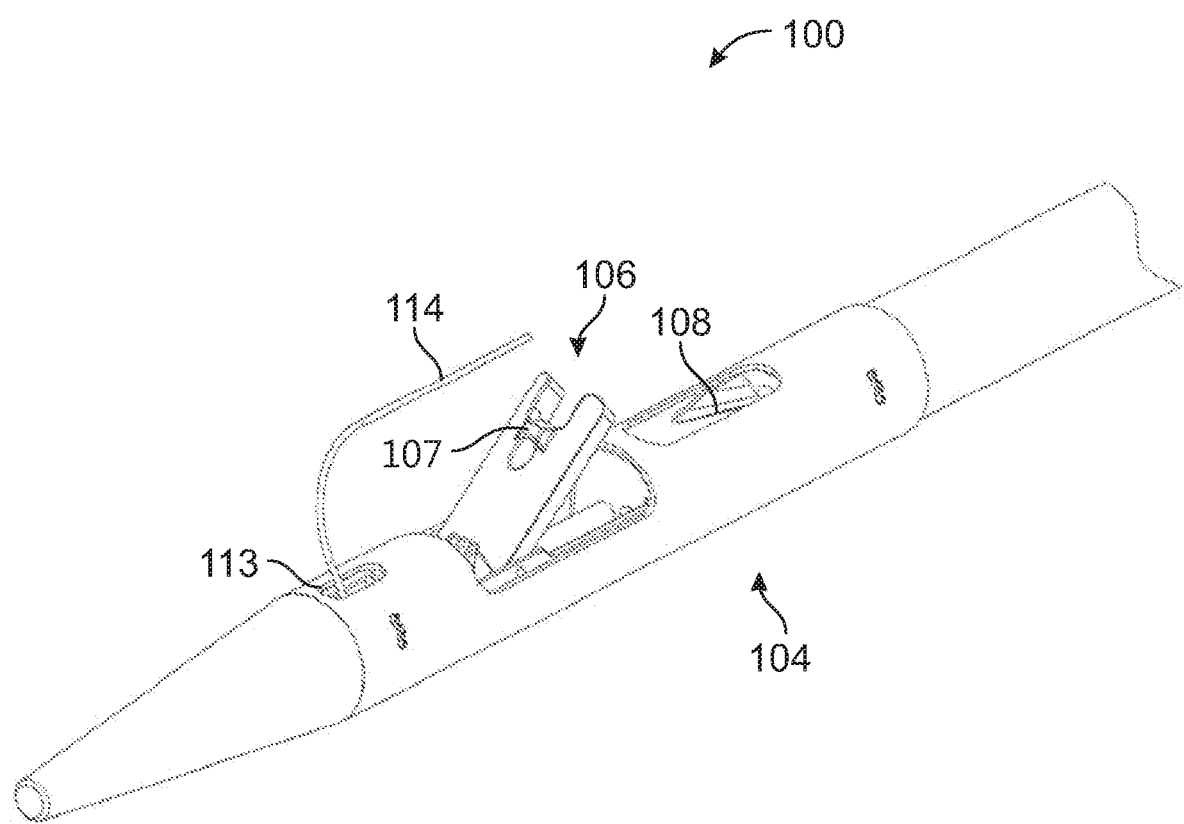
FIG. 2 shows a perspective view of one of the suturing devices of FIG. 1.

FIG. 2 illustrates a distal end of suturing device 100. As shown, the distal end can include a needle guide 108 for guiding a needle to suture clasp arm 106. In some embodiments, the needle guide 108 can have an angled groove or channel such that it will deflect a suture catch mechanism, or needle, exiting the elongate body 104 along a path that intercepts the suture clasp arm 106. Further, FIG. 2 illustrates the suture clasp arm 106 in a deployed position and as shown, the suture clasp arm 106 extends generally proximally. In the embodiment illustrated in FIG. 2, the suture clasp arm 106 is distal to the needle guide 108, and thus the needle is configured to move distally. In some embodiments, a guidewire can be used to deliver the suturing device, with the elongate body 104 passing over the guidewire such that the guidewire extends through a distal tip of the elongate body 104. In some embodiments, a suture portion 114 extends through an interior of the elongate body 104 and exits through an aperture 113 in order to be held by the suture clasp arm 106. The aperture 113 can be distal to the suture clasp arm 106 and needle guide 108, and the suture portion 114 can be drawn proximally from the suture clasp arm 106 by the needle 112 into the elongate body 104 as discussed below.

Figure 3:
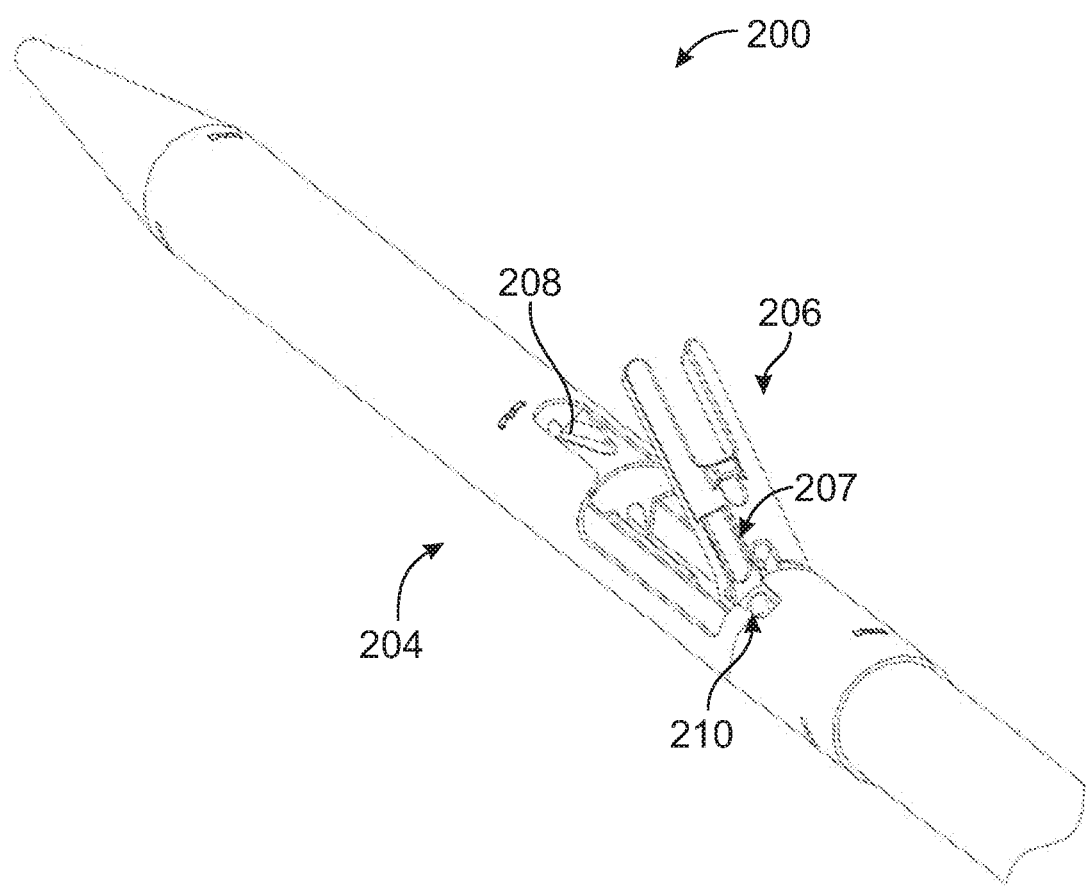
FIG. 3 shows a perspective view of one of the suturing devices of FIG. 1.

FIG. 3 illustrates a distal end of suturing device 200. As shown, the distal end can include a needle guide 208 for guiding a needle to suture clasp arm 206. In some embodiments, the needle guide 208 can have an angled groove or channel such that it will deflect a suture catch mechanism, or needle, exiting the elongate body 204 along a path that intercepts the suture clasp arm 206. Further, FIG. 3 illustrates the suture clasp arm 206 in a deployed position and as shown, the suture clasp arm 206 extends generally distally. In some embodiments, the distal end may include an opening or aperture, such as at the distal tip, for a first guidewire to extend. There may be an additional opening proximal to the suture clasp arm 206 for a second guidewire to extend. In the embodiment illustrated in FIG. 3, the suture clasp arm 206 is proximal to the needle guide 208, and thus the needle is configured to move proximally. In some embodiments, the elongate body 204 can include an aperture 213 for a suture portion 214 to extend out of (shown in FIG. 4E) to be held by the arm 206. The aperture 213 can be proximal to the suture clasp arm 206 and needle guide 208, and thus the suture portion 214 can extend distally from the aperture 213 to the suture clasp arm 206, and can further be drawn distally from the suture clasp arm 206 by the needle 212 into the elongate body 204 as discussed below.

The suture clasp arms 106/206 can comprise one or more suture mounts or clasps 107/207. The suture clasps 107/207 can be adapted to releasably retain a suture portion 114/214. In some embodiments, the suture clasps can releasably retain a suture portion 114/214 while the suture clasp arms 106/206 are in the retracted position and in the extended position. In some embodiments, a suture end may be retained in the suture clasps. In some embodiments, the suture clasps may retain a portion of suture that is not the suture end.

Further details on the suturing devices 100/200 can be found in U.S. Pat. No. 9,131,938, filed Feb. 7, 2013, the entirety of which is hereby incorporated by reference in its entirety.

Methods of Use of Dual Device System

Figure 4A:
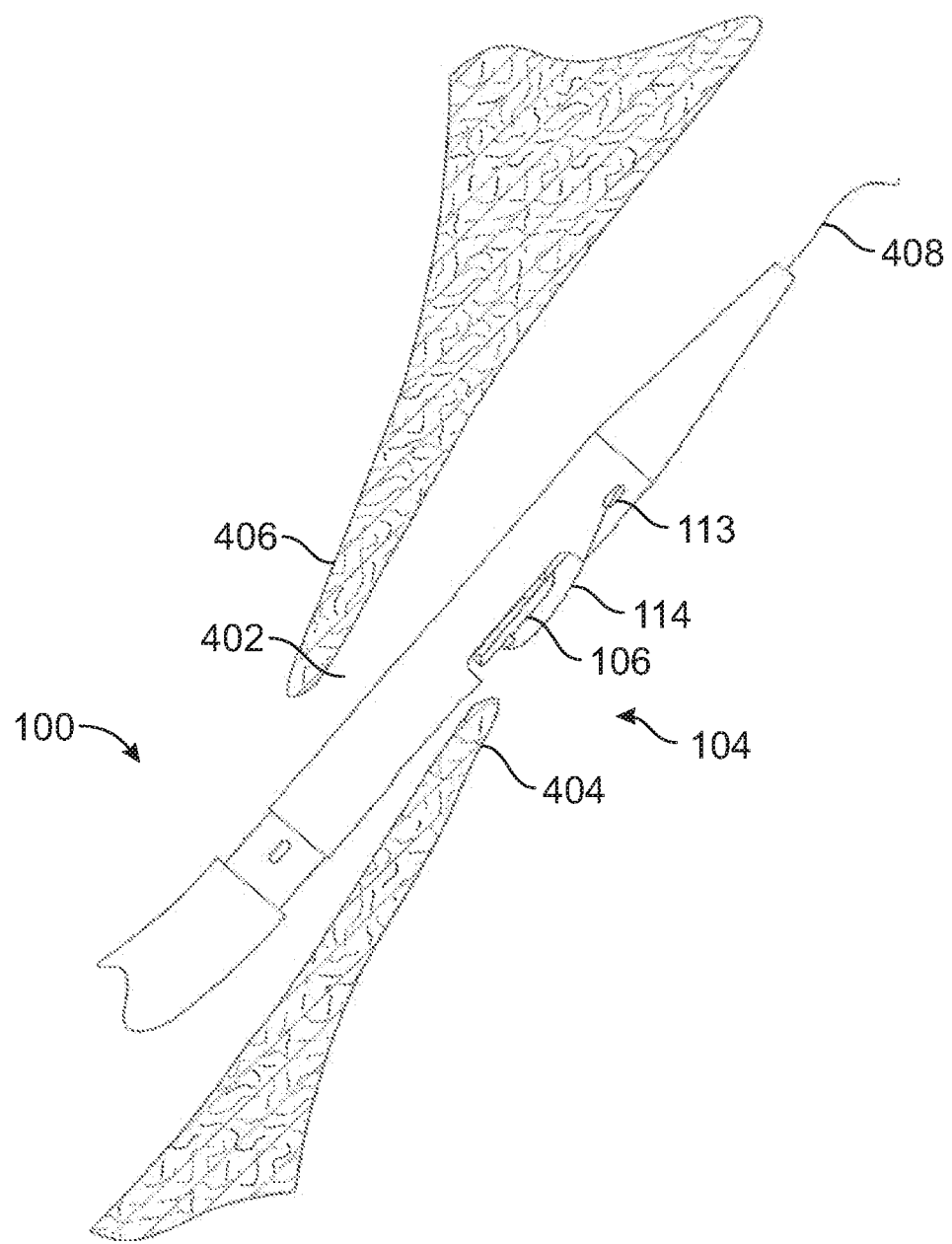
FIGS. 4A-K illustrate an embodiment of a procedure for suturing a PFO using the disclosed suturing devices.

The operation of the system comprising the first suturing device 100 and the second suturing device 200, described above, is illustrated according to one embodiment in FIGS. 4A-J in conjunction with a procedure for closing a PFO. As shown in FIG. 4A, the distal end of a suturing device 100 can be advanced through the vasculature and positioned in the tunnel 402 of the PFO between the septum primum 404 and the septum secundum 406. The suturing device 100 may be advanced over a guidewire 408 or alternatively delivered through a catheter introducer sheath using techniques which are known in the art.

Figure 4B:
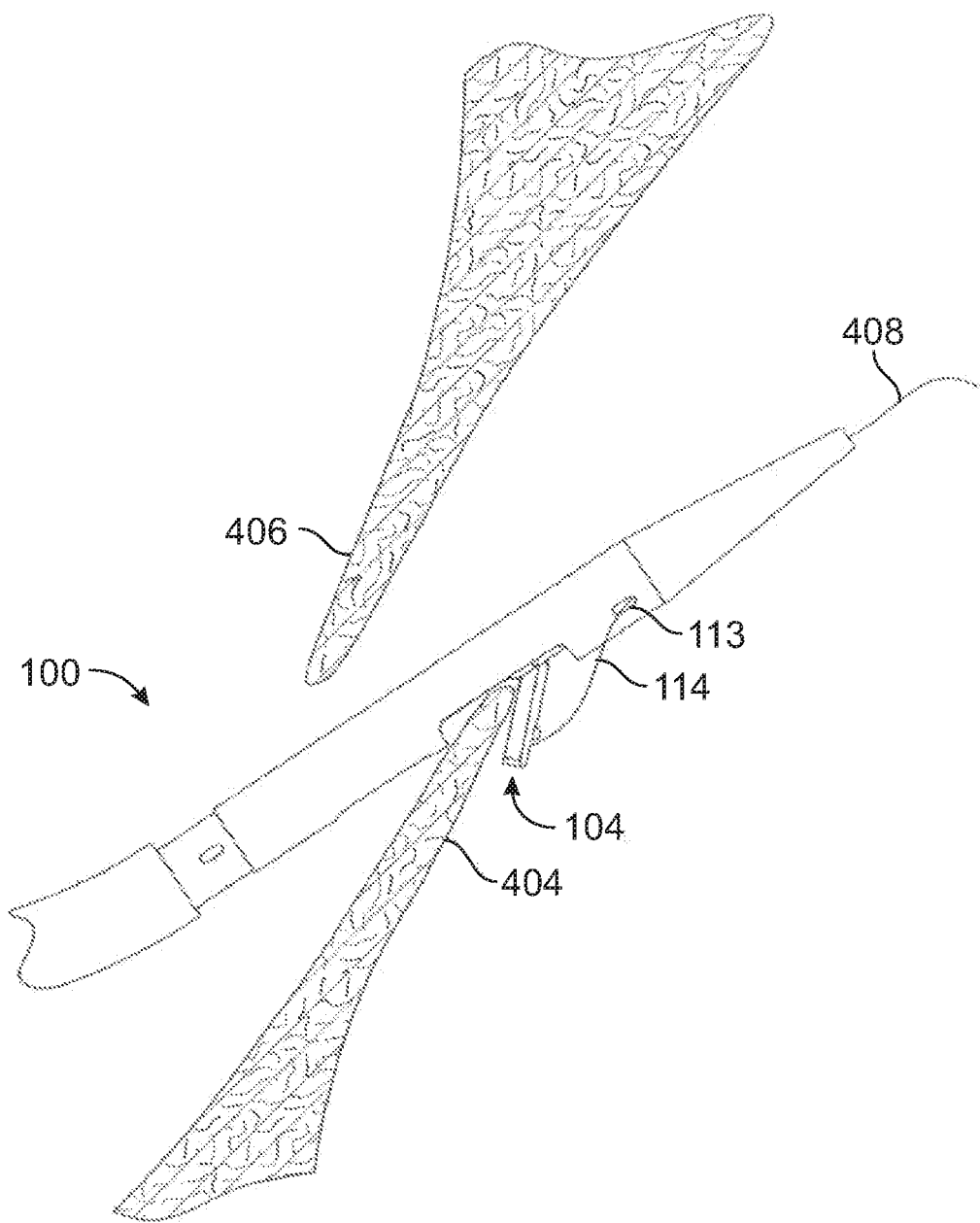

The suturing device 100 can be initially positioned such that the suture clasp arm 106 is near the tip of the septum primum 404, thus suture clasp arm 106 is permitted to extend from the elongate body 104. The suture clasp arm 106 may then deployed and then the device 100 is retracted until the suture clasp arm 106 extends around the tip of the septum primum 404, as shown in FIG. 4B, and gathers the tissue of the septum primum 404 between the suture clasp arm 106 and the elongate body 104.

Figure 4C:
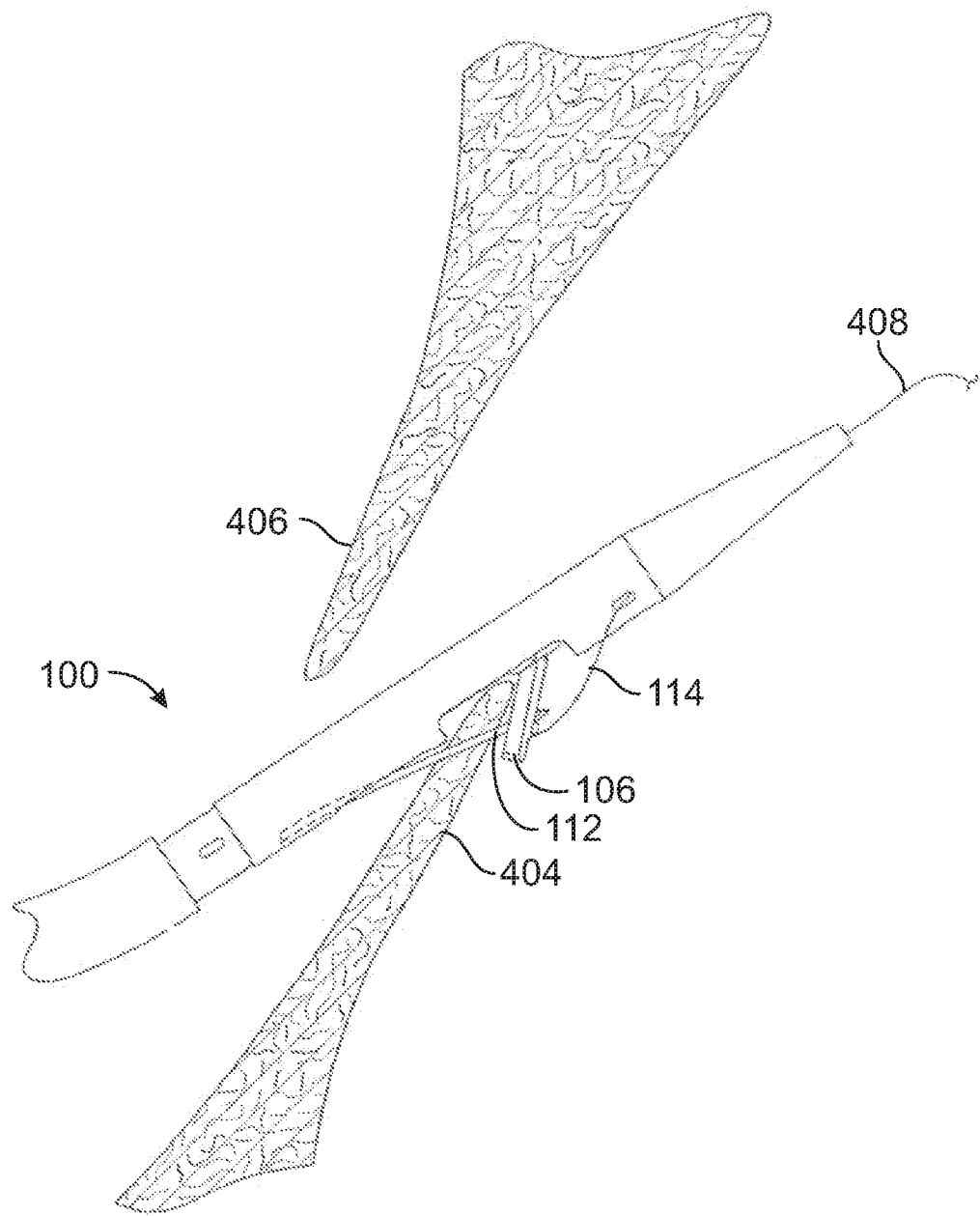

Once the suture clasp arm 106 has been properly positioned around the septum primum 404, needle 112 may be deployed from the suturing device 110 to penetrate the septum primum 404 and engage the suture clasp arm 106. The needle 112 is advanced through a passageway in the suturing device 100 and deflected by needle guide 108 along an angle that intersects the deployed suture clasp arm 106 as it exits the suturing device 100. The needle 112 engages the suture clasp arm 106, as shown in FIG. 4C, to engage the suture portion 114.

Figure 4D:
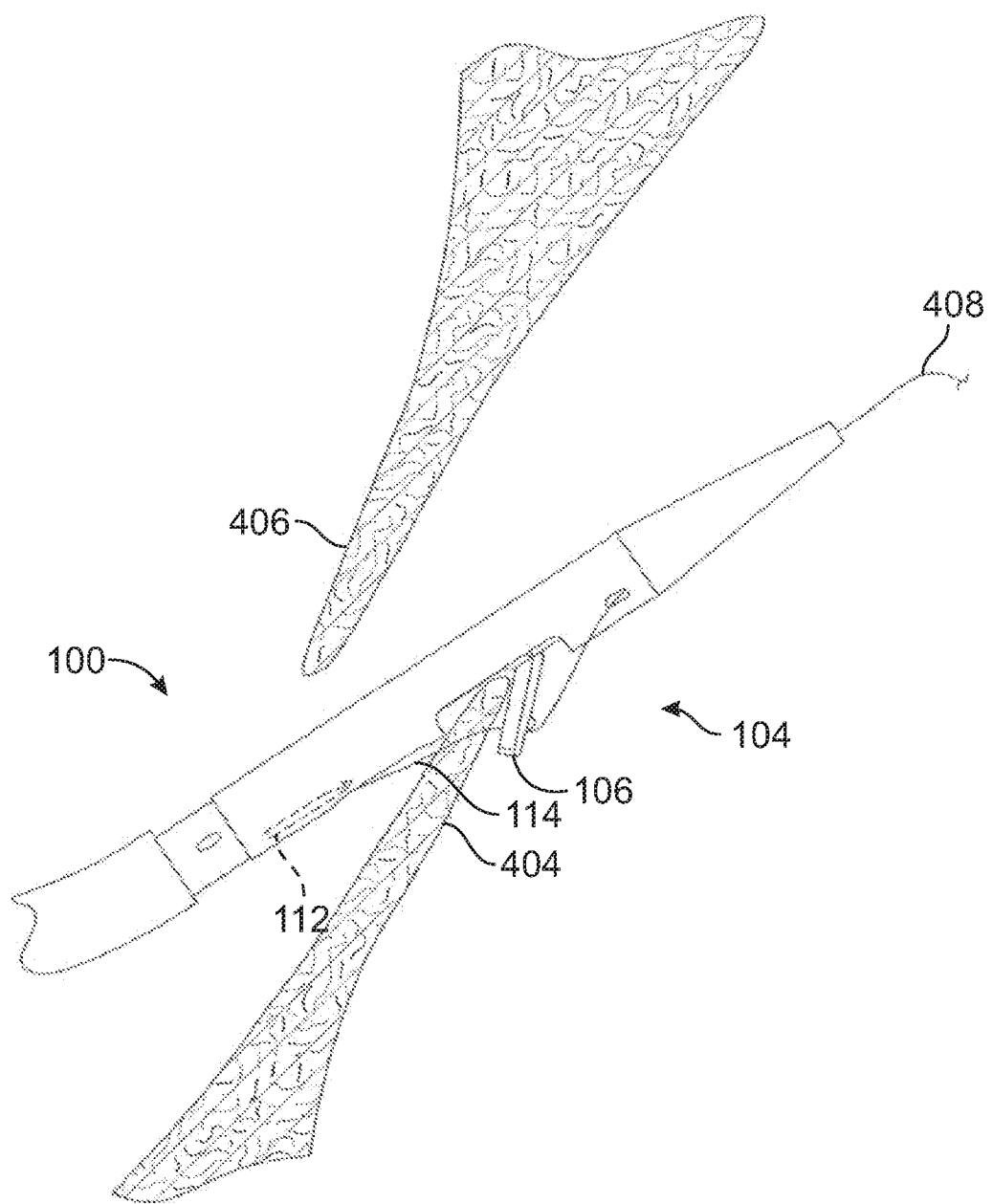

As shown in FIG. 4D, once the suture portion 114 has been engaged, the needle 112 and engaged suture portion 114 can then be retracted through the tissue of the septum primum 404 into the elongate body 104 of the suturing device 110. The device 100 may be advanced slightly so that the suture clasp arm 106 can be closed without pinching the septum primum 404. The first suturing device 100 may then be withdrawn from the vasculature over the guidewire 408, pulling the suture through the penetrated body tissue of the septum primum.

Figure 4E:
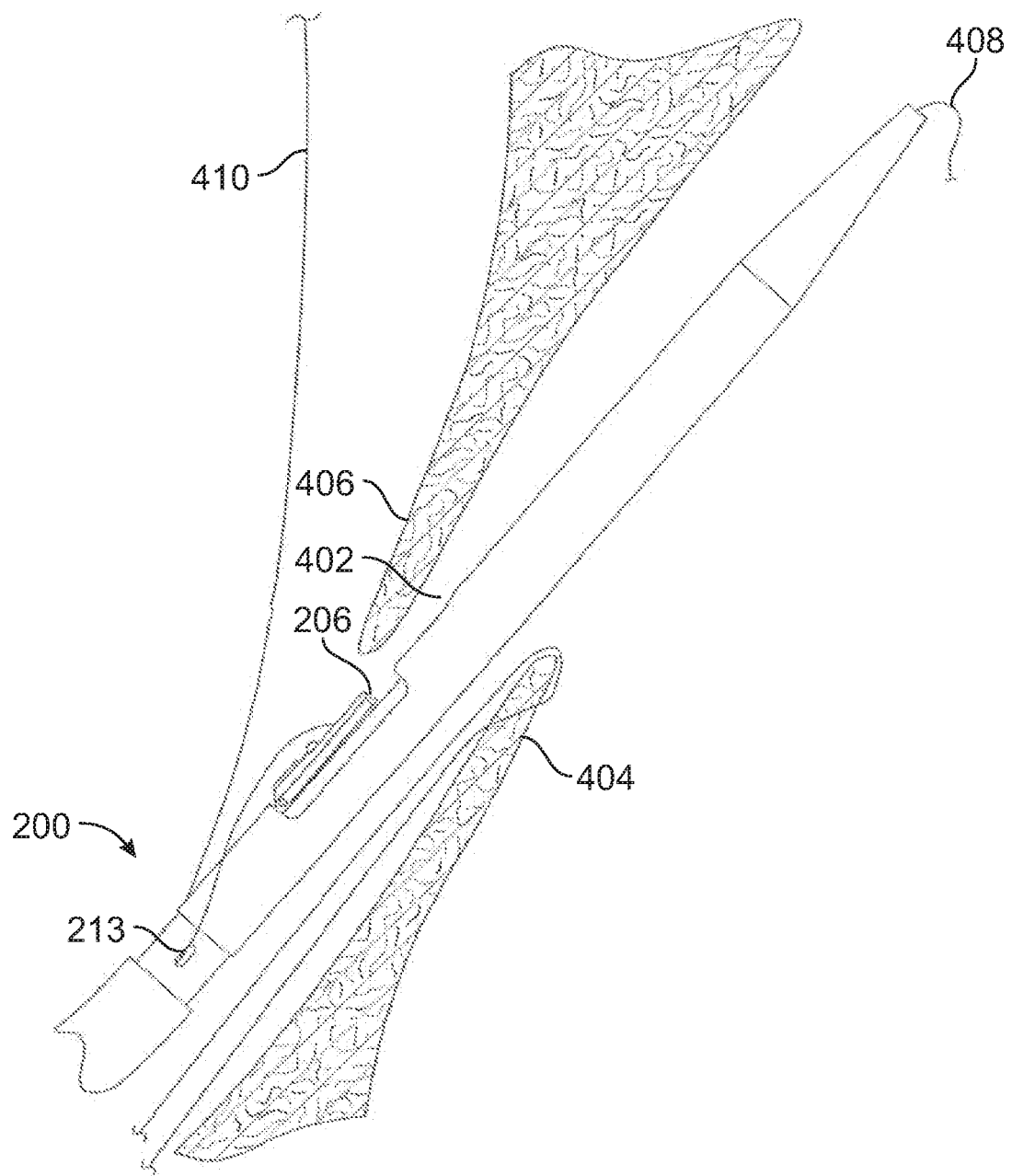

The second suturing device 200 may then be advanced through the venous access into the tunnel 402 of the PFO between the septum primum 404 and the septum secundum 406, as shown in FIG. 4E. The second guidewire 410 can be advanced through the opening into the superior vena cava. The second guidewire 410 may be preloaded in the device 200 before introduction of the device 200 into the body such that a distal end of the second guidewire is near the opening.

Figure 4F:
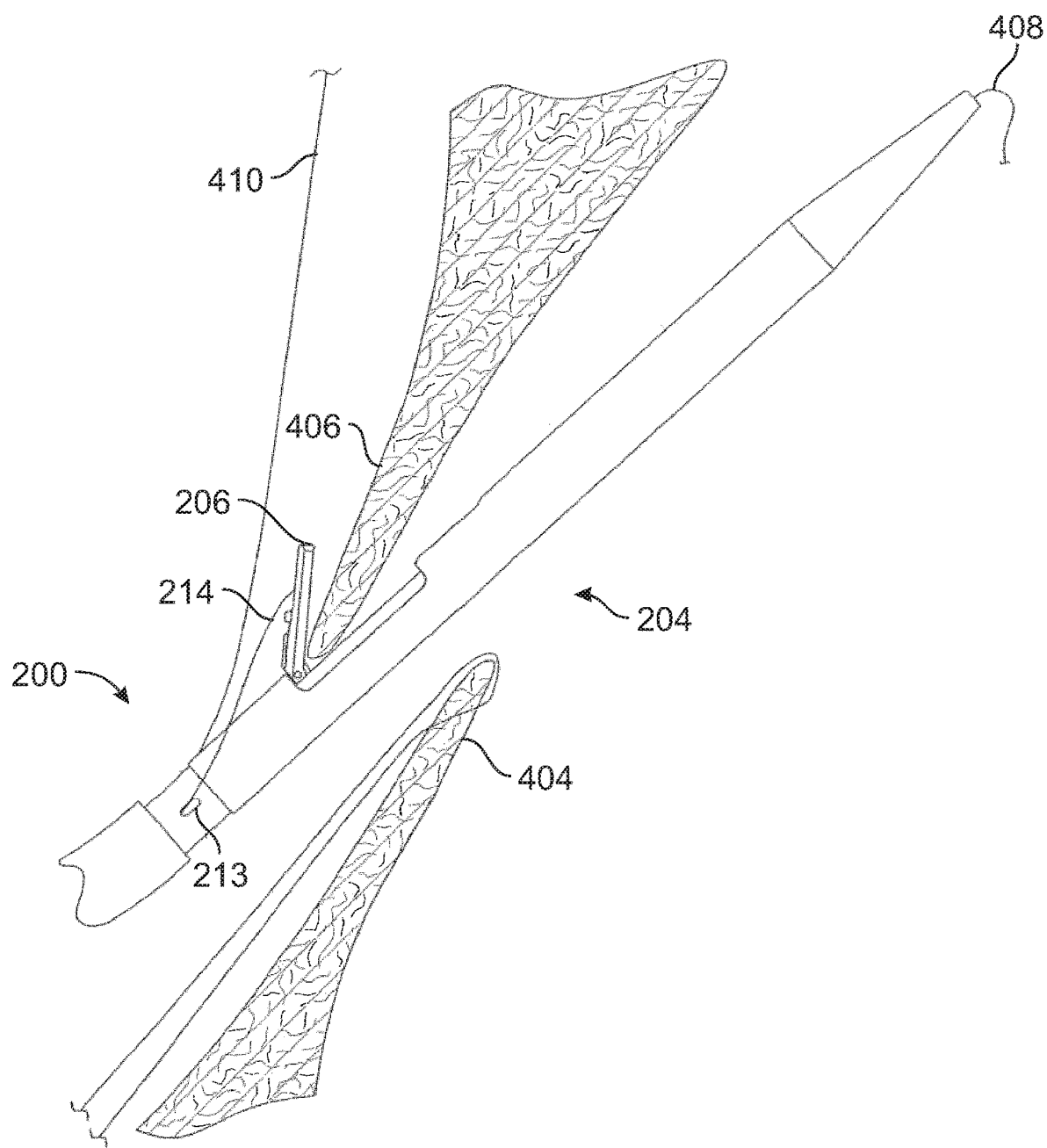

The suture clasp arm 206 can then be extended and the device 200 can be advanced such that the suture clasp arm 206 extends around the tip of the septum secundum 406, as shown in FIG. 4F, and gathers the tissue of the septum secundum 406 between the arm 406 and the elongate body 402. Alternatively, the suture clasp arm 406 can be extended from the elongate body 402 before the second guidewire 410 is advanced into the superior vena cava. The suturing device 200 can be configured such that when the second guidewire 410 is advanced into the superior vena cava, the second guidewire 410 directs the device 200 toward the center of the septum secundum 406 as the device 200 is advanced.

Figure 4G:
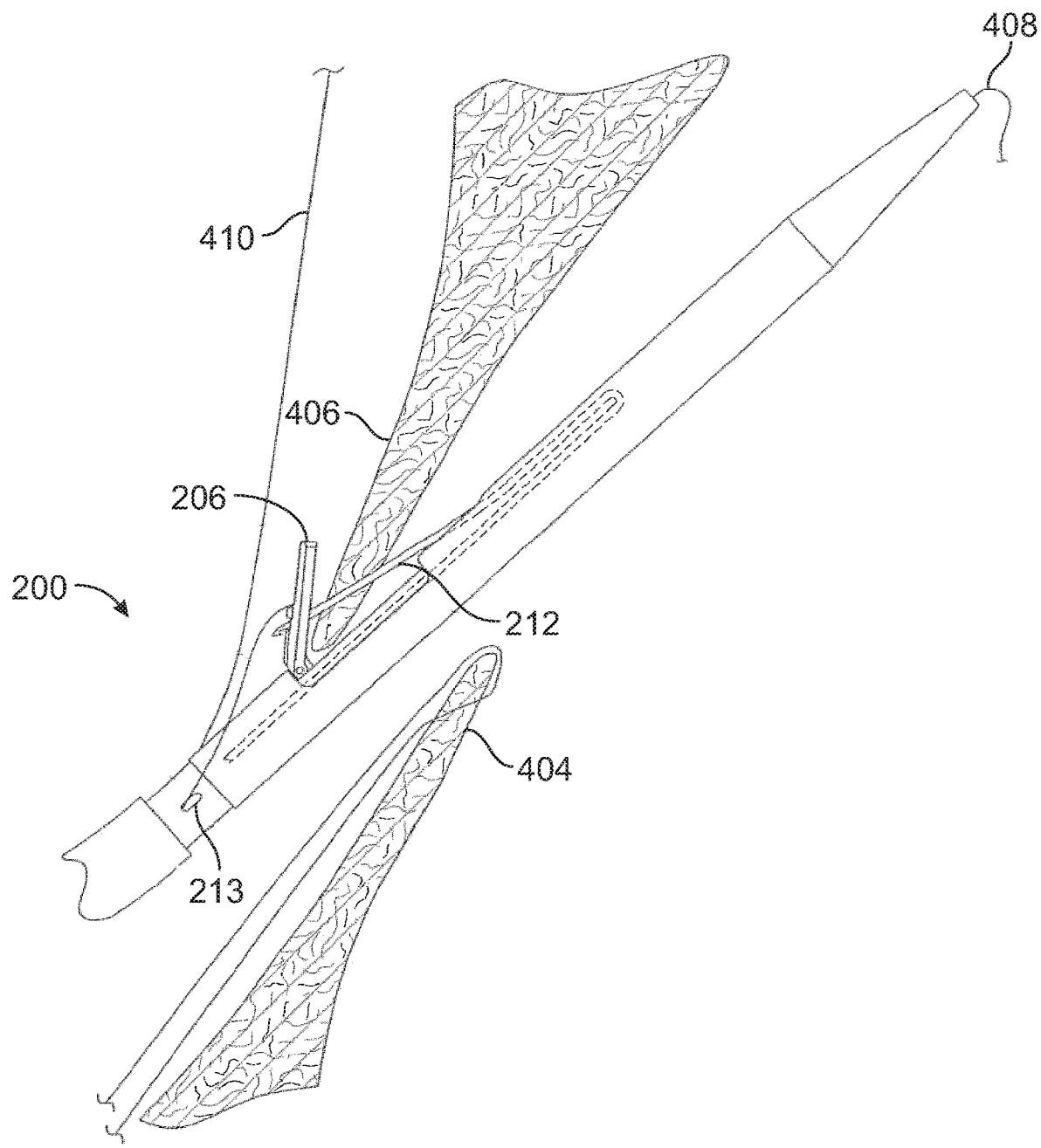

Once the suture clasp arm 206 and suture portion 214 have been properly positioned around the septum secundum 406, the needle 212 may be deployed from the distal end of the suturing device 200 to penetrate the septum secundum 406 and engage the suture portion 214. As shown in FIG. 4G, the tip of the needle 212 is pulled proximally from a location distal the suture clasp arm 206 through the tissue of the septum secundum 406 towards deployed suture clasp arm 206 to engage the suture portion 214, as shown in FIG. 4G.

Figure 4H:
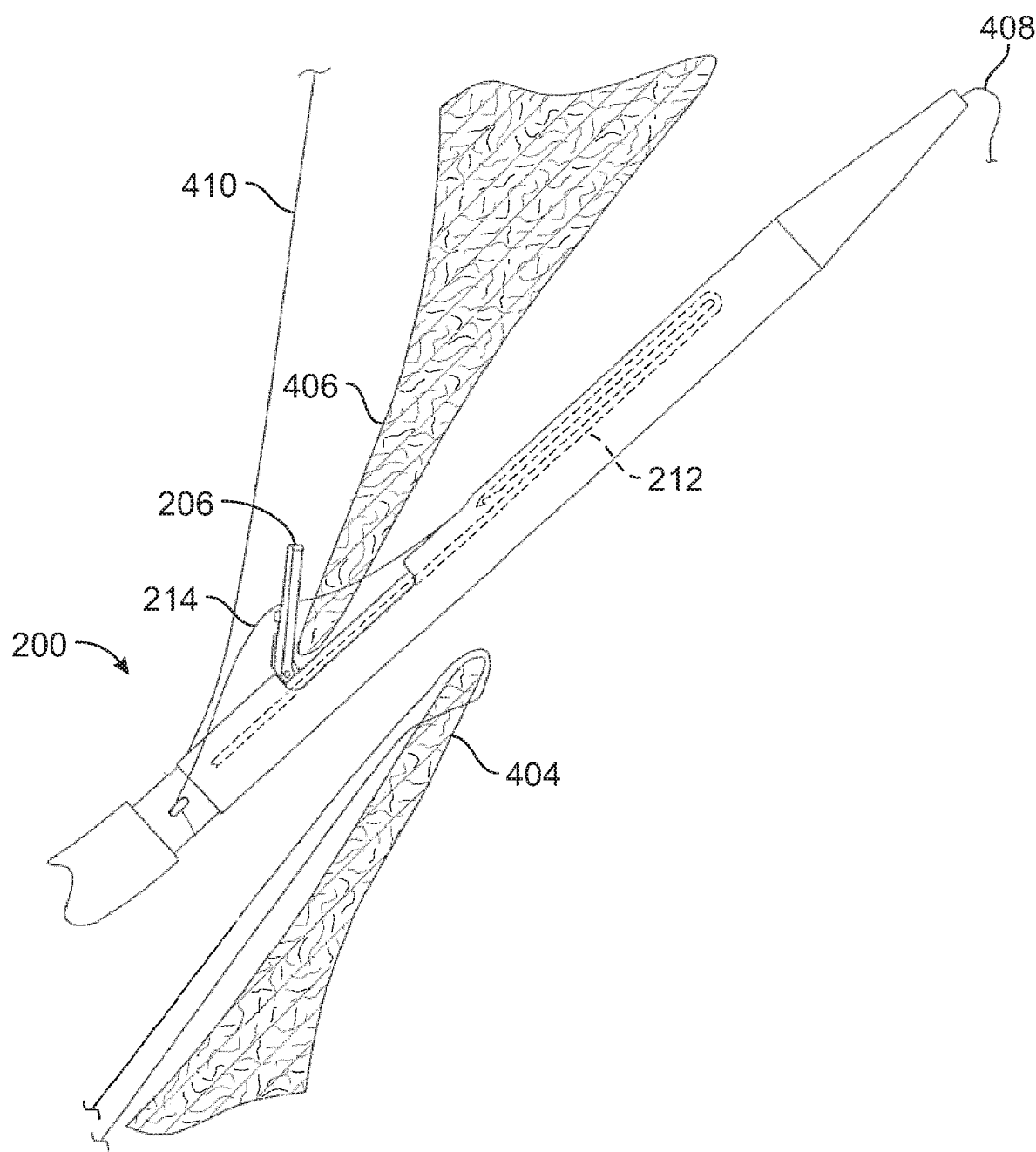

After the suture portion 214 has been engaged, the needle 212 and engaged suture portion 214 can then be retracted distally through the tissue of the septum secundum 406 and into the suturing device 200, as illustrated in FIG. 4H. The suture clasp arm 206 may then be closed and thereafter the second guidewire 410 retracted into the suturing device 200. Alternatively, the second guidewire 410 can be retracted into the suturing device 200 before the suture clasp arm 206 is closed. Once the suture clasp arm 206 is closed, the suturing device 200 may be withdrawn from the patient's heart, pulling the suture through the penetrated body tissue of the septum secundum.

Figure 4I:
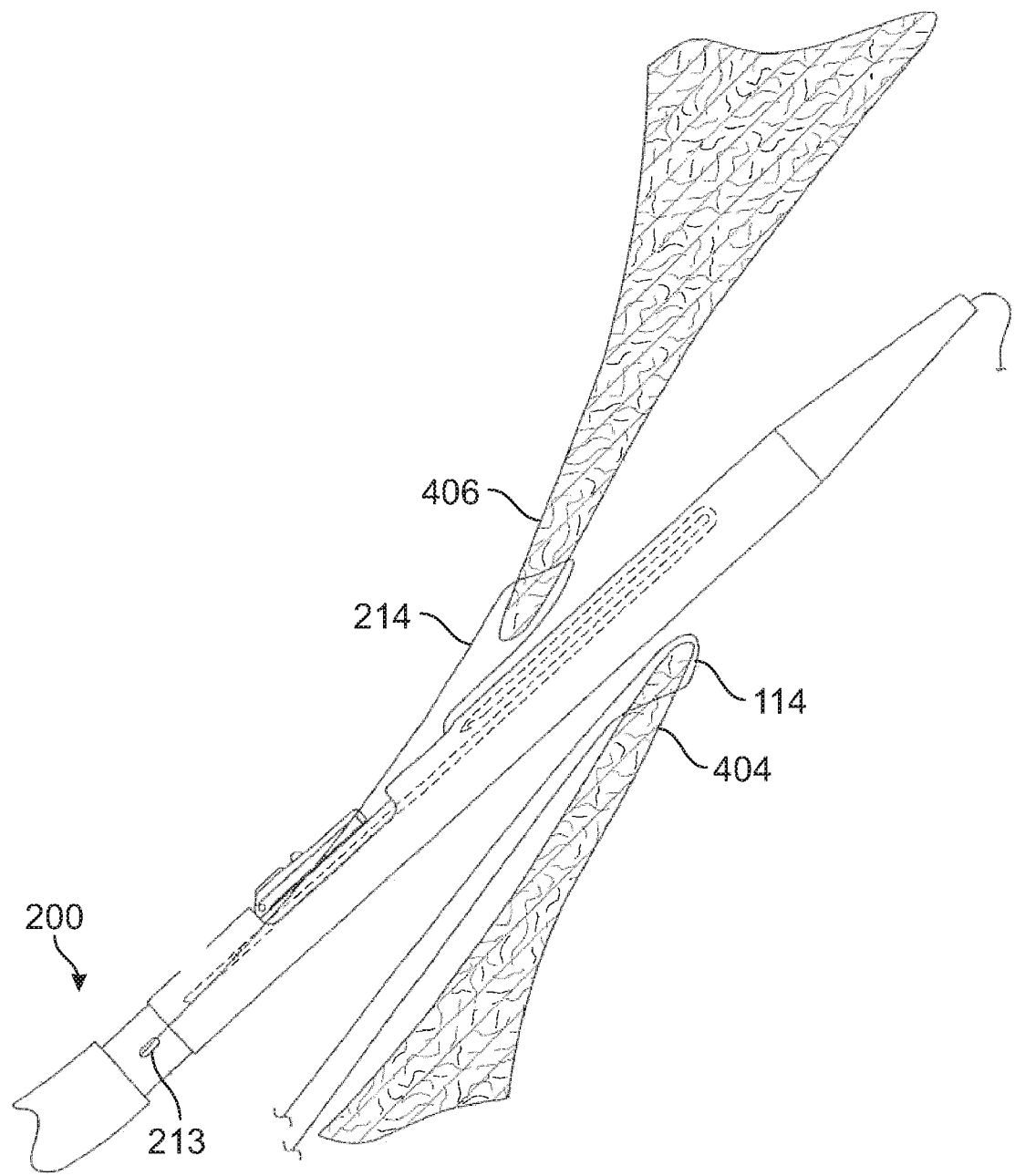
Figure 4J:
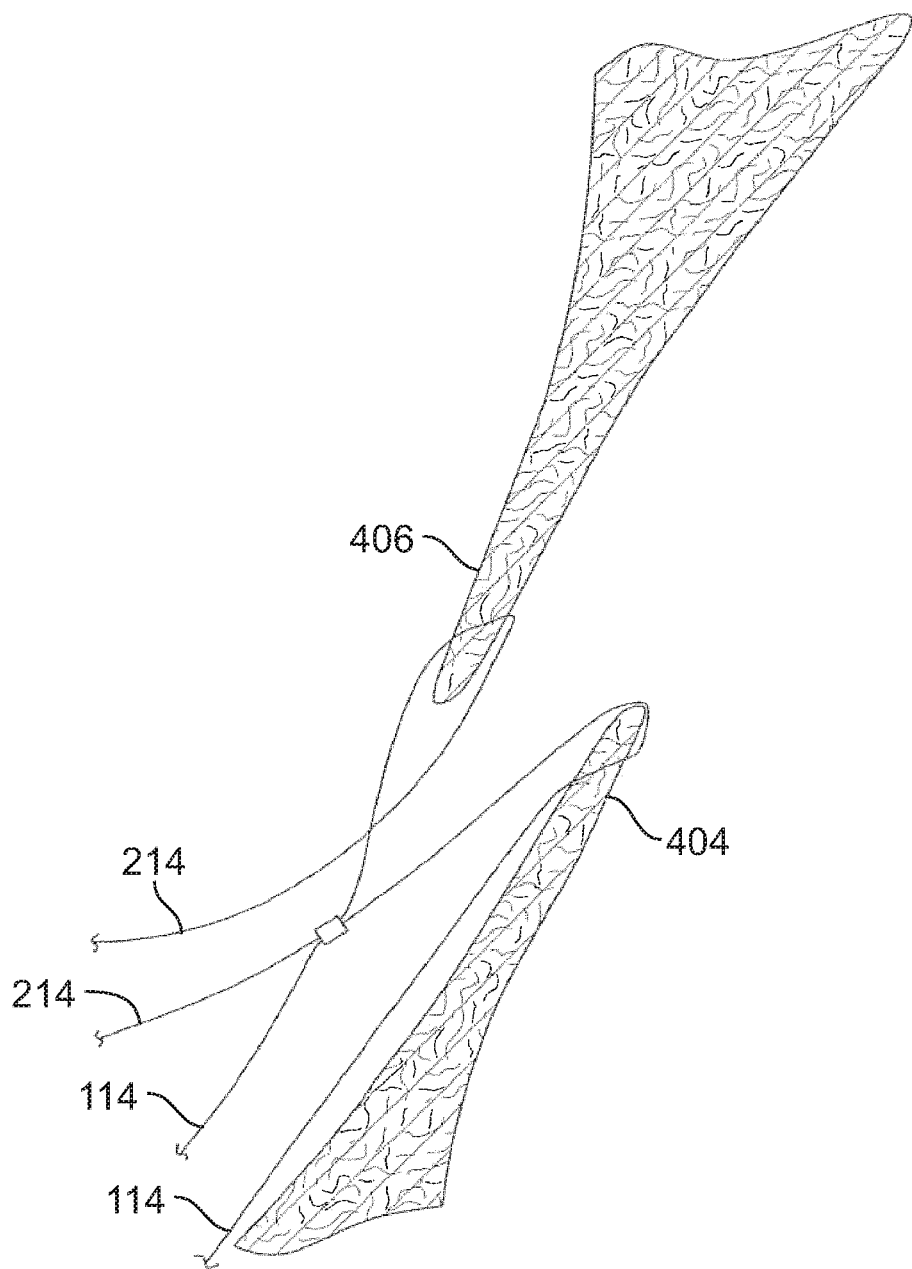

As shown in FIG. 4I, the suture portion 114 has been positioned through the septum primum 404 while suture portion 214 has been positioned through the septum secundum 406. After the suturing device 200 has been withdrawn, the suture portions 114/214 will extend proximally from the PFO. The suture portions 114/214 can then be secured together, as illustrated in FIG. 4J, by tying a knot according to any known method or by applying a knot by any method or device that is described or referenced herein. The suture portions FIG. 4J can be secured together exterior to the body or within the body. Any excess portion of sutures can be trimmed.

Figure 4K:
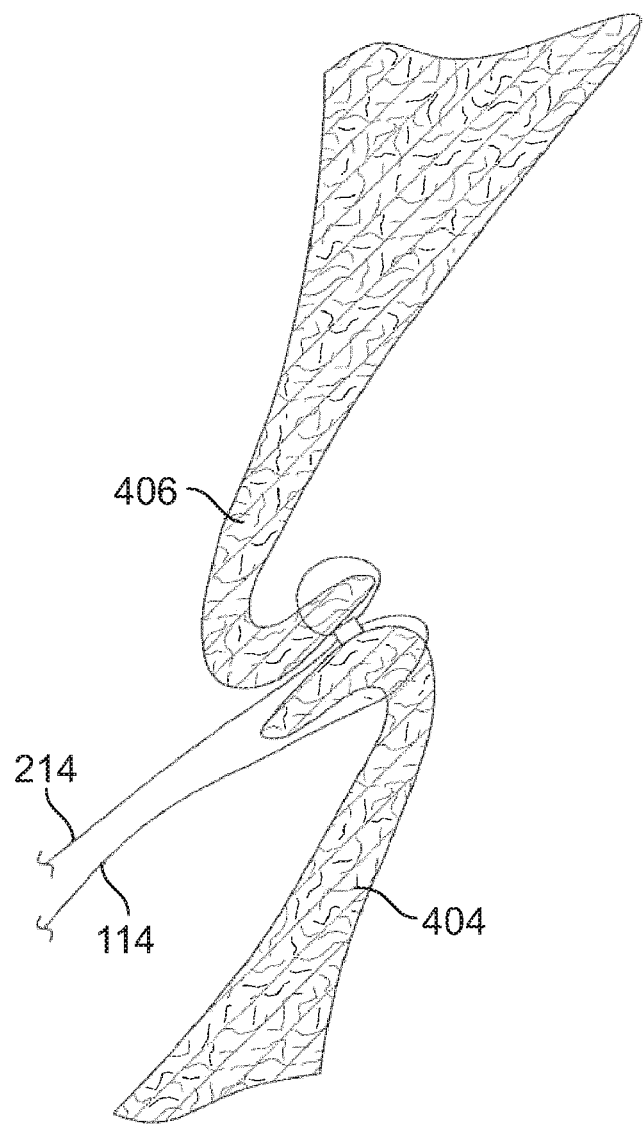

The suture portions 114/214 can then be pulled to draw the septum secundum 406 and septum primum 404 towards one another to close the PFO, as described above. As the sutures are pulled tight, the sutures preferably cause the septum secundum 406 and septum primum 404 to turns or folds so that the tip of the septum primum 404 extends in the opposite direction compared to the tip of the septum secundum 406, as shown in FIG. 4K. The knot can be positioned between the septum primum 404 and the septum secundum 406, as illustrated in FIG. 4K. Such placement of the knot may agitate the tissue and promote healing between the septum primum 404 and the septum secundum 406. In one embodiment, the knot is positioned between the septum primum 404 and the septum secundum 406, as illustrated in FIG. 4K, by pulling the suture portion 214 until the knot is pulled against the septum secundum 406 then pulling the suture portion 114 to those the PFO.

Figure 5A:
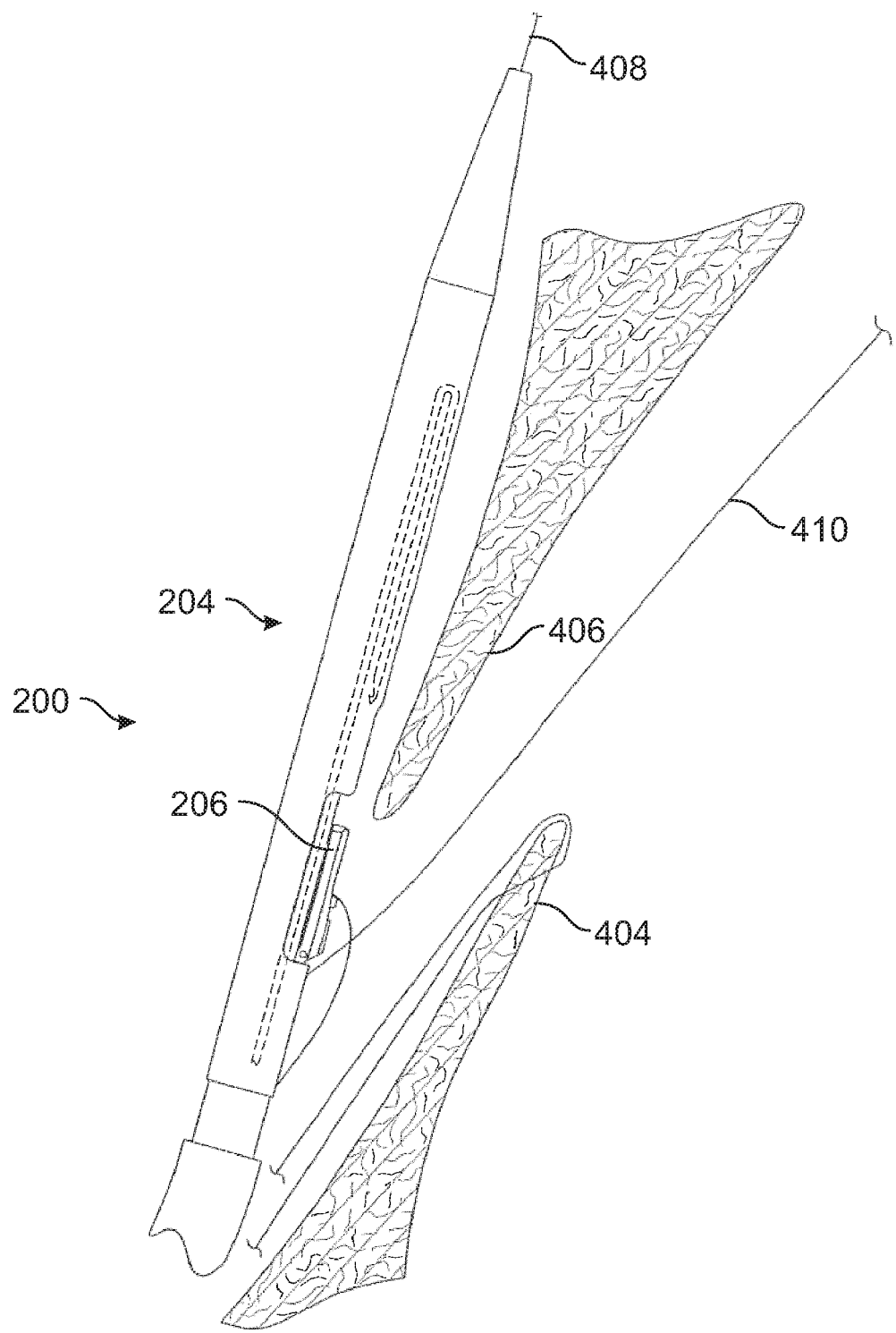
FIGS. 5A-E illustrates another embodiment of a procedure for suturing a PFO using the disclosed suturing devices.

An alternative method of operation of the second suturing device 200 is illustrated according to one embodiment in FIG. 5A-E. After operating the first suturing device 100 according to the above description of FIGS. 4A-D and withdrawn, the second suturing device 200 may then be advanced through the venous access into the right atrium of the heart adjacent to the PFO, as shown in FIG. 5A. The first guidewire 408 can be withdrawn from the PFO and advanced into the superior vena cava before or after introduction of the second suturing device 200. Additionally or alternatively, a portion of the device 200 can be advanced into the superior vena cava.

Figure 5B:
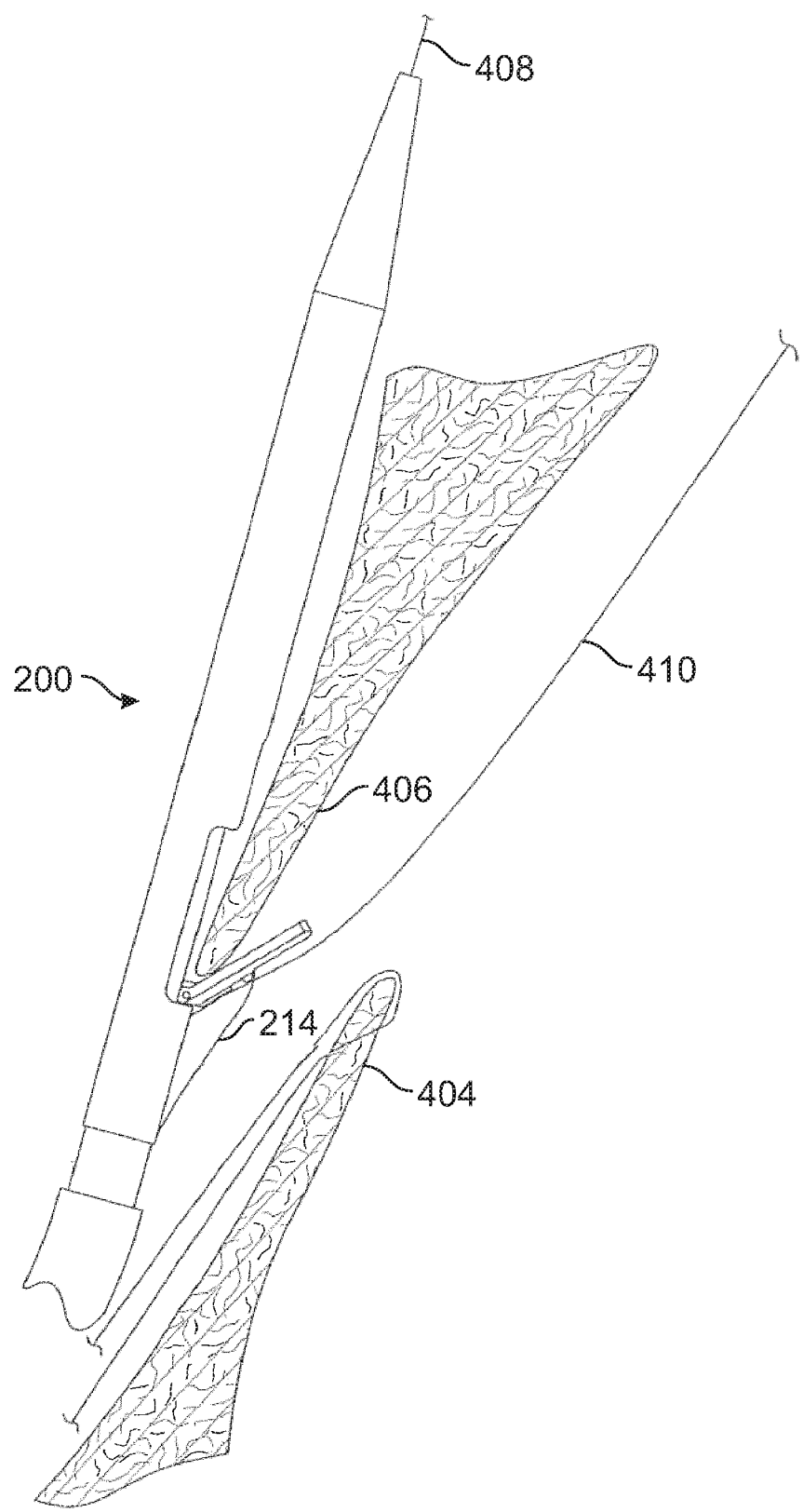

The second guidewire 410 can be advanced from the opening through the PFO between the septum primum 404 and the septum secundum 406. The suture clasp arm 206 can then be extended and the device 200 can be advanced such that the suture clasp arm 206 extends around the tip of the septum secundum 406, as shown in FIG. 5B, and gathers the tissue of the septum secundum 406 between the arm 206 and the elongate body 204. Alternatively, the suture clasp arm 206 can be extended from the elongate body 204 before the second guidewire 410 is advanced into the PFO. The suturing device 200 can be configured such that when the first guidewire 408 is advanced into the superior vena cava and the second guidewire 410 is positioned through the PFO, the first guidewire 408 and the second guidewire 410 direct the device 200 toward the center of the septum secundum 406 as the device 200 is advanced.

Figure 5C:
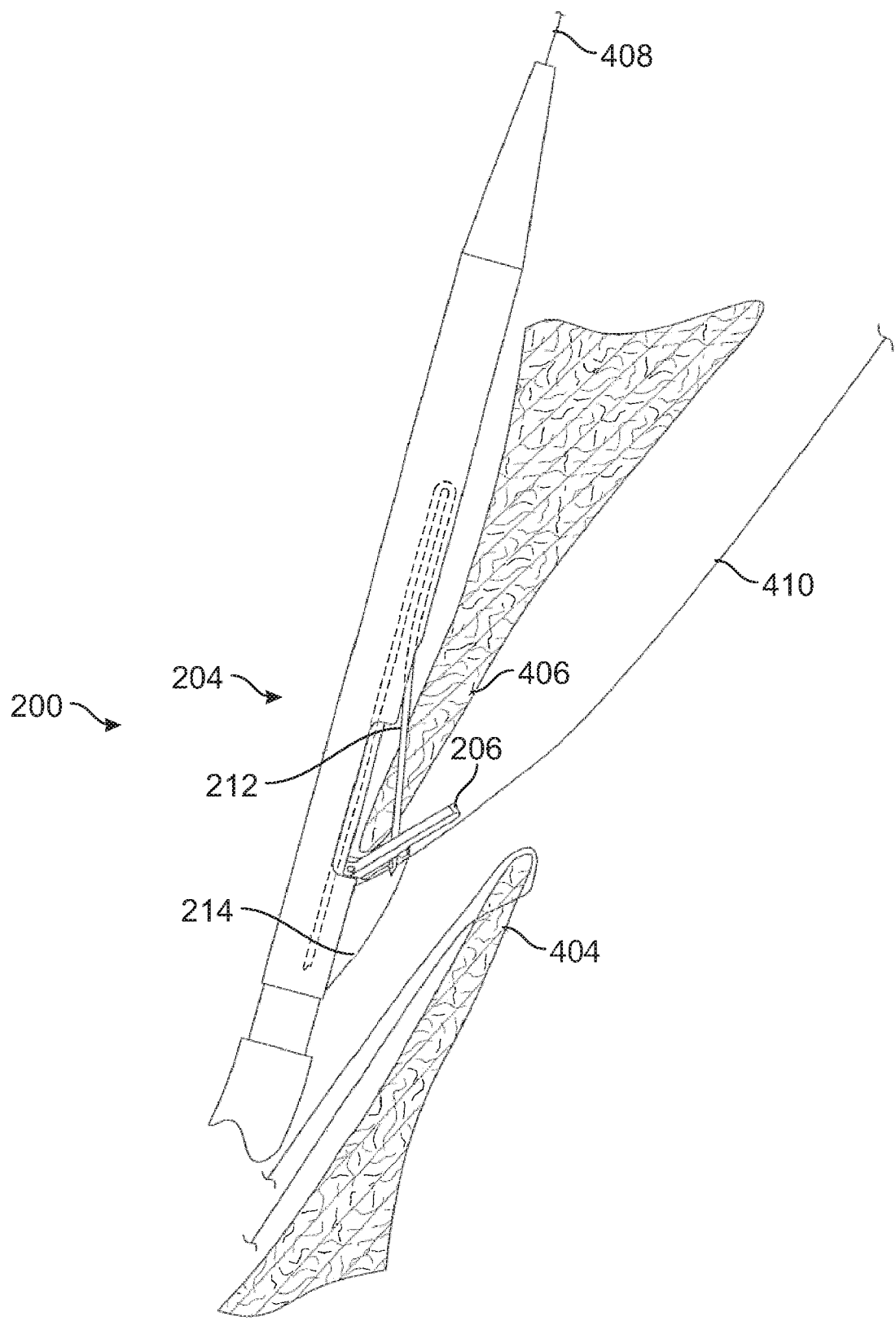

Once the suture clasp arm 206 and suture portion 214 have been properly positioned around the septum secundum 206, the needle 212 may be deployed from the distal end of the suturing device 200 to penetrate the septum secundum 406 and engage the suture portion 214. As shown in FIG. 5C, the tip of the needle 212 is pulled proximally from a location distal the suture clasp arm 206 through the tissue of the septum secundum 406 towards deployed suture clasp arm 206 to engage the suture portion 214.

Figure 5D:
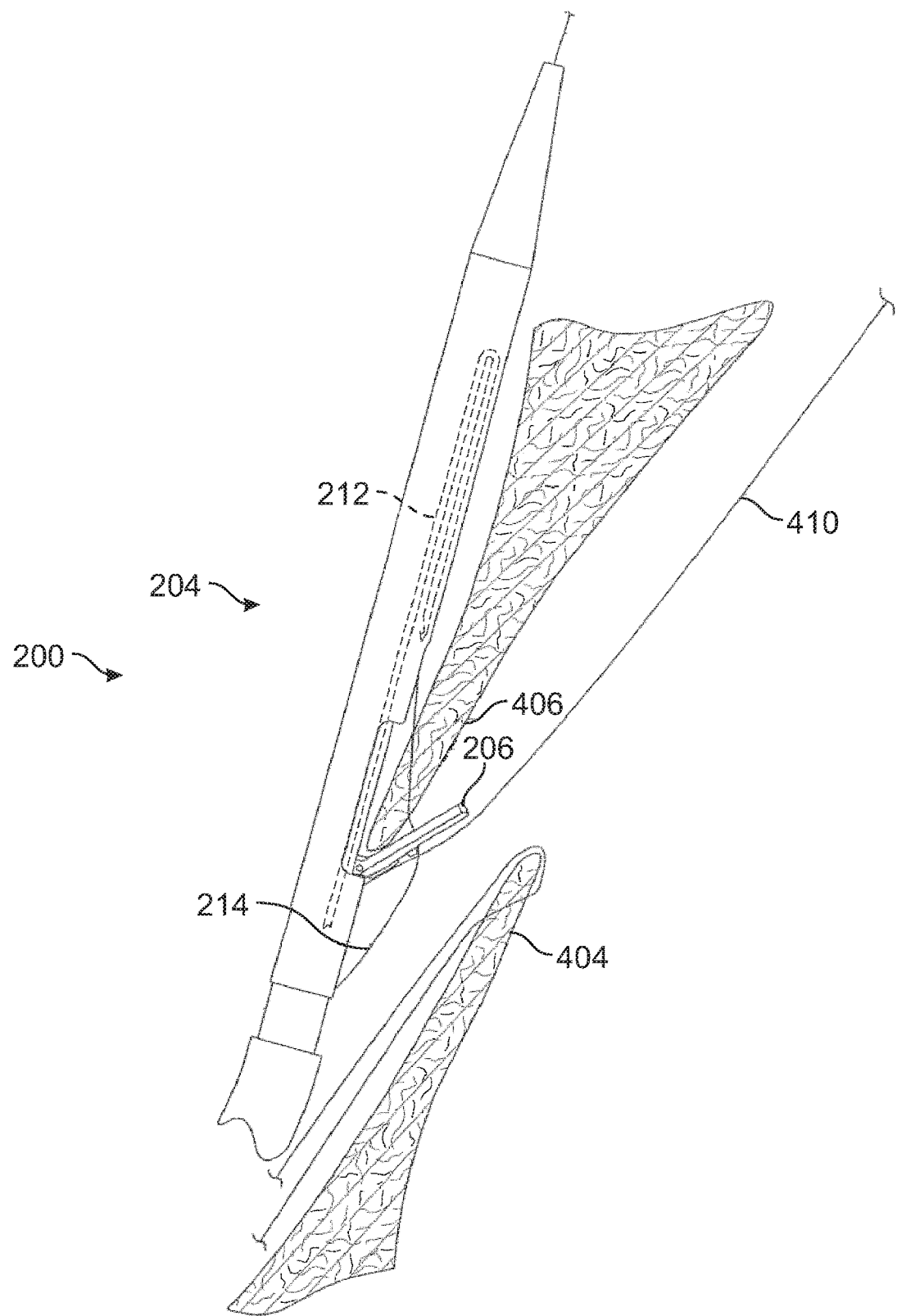

As shown in FIG. 5D, once the suture portion 214 has been engaged, the needle 212 and engaged suture portion 214 can be retracted distally through the tissue of the septum secundum 406 and into the suturing device 200. The device 200 can then be retracted slightly to permit the suture clasp arm 206 to close. Thereafter, the second guidewire 410 can be retracted into the suturing device 200. Alternatively, the second guidewire 410 can be retracted into the suturing device 200 before the suture clasp arm 206 is closed. Once the suture clasp arm 206 is closed, the suturing device 200 may be withdrawn from the patient's heart, pulling the suture through the penetrated body tissue of the septum secundum.

Figure 5E:
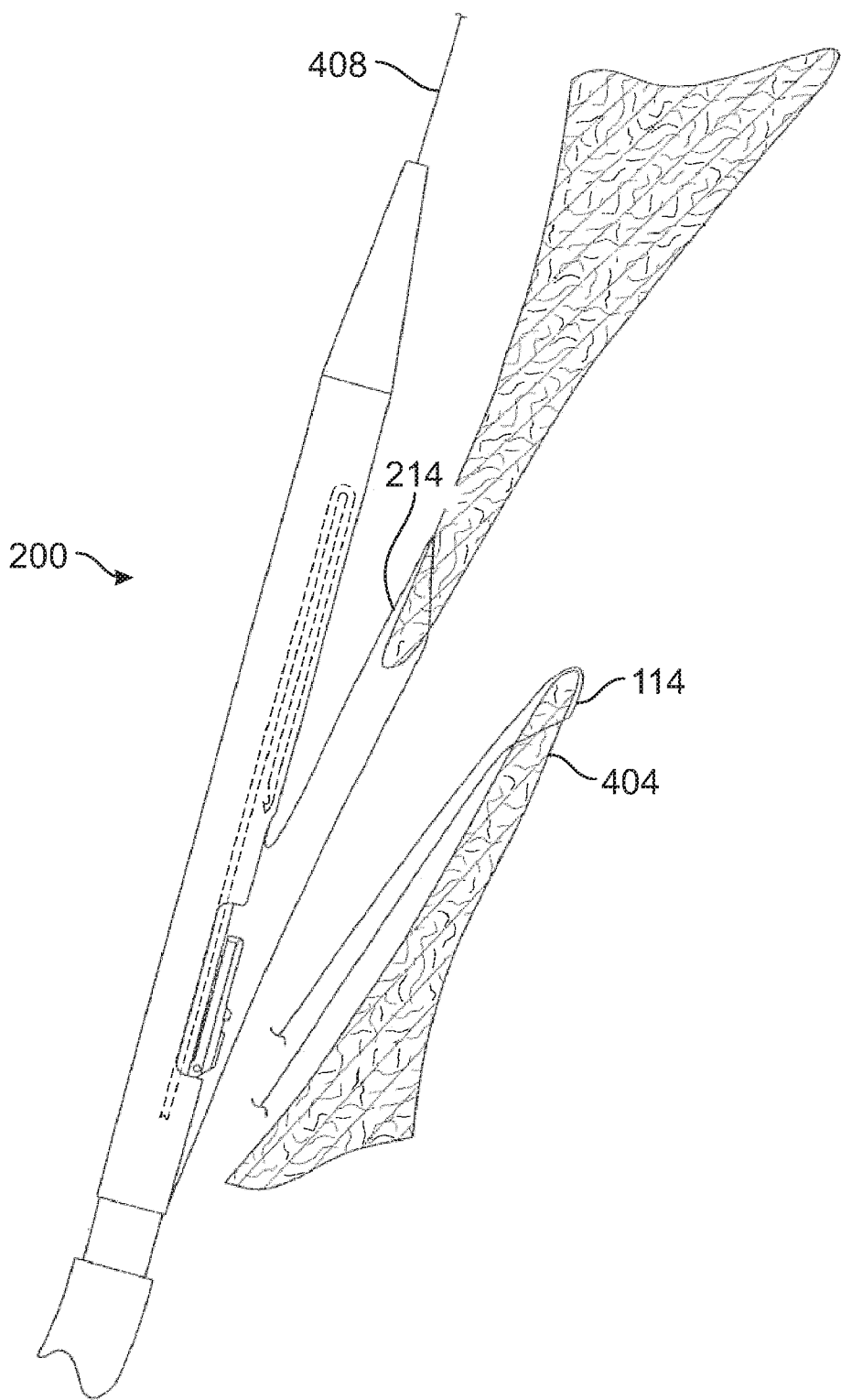

As shown in FIG. 5E, the suture portion 114 has been positioned through the septum primum 404 while suture portion 214 has been positioned through the septum secundum 406. After the suturing device 200 has been withdrawn, the sutures and can be used to draw the septum secundum 406 and septum primum 402 together to close the PFO, as described above.

Although the operation of the devices 100 and 200 has been described with reference to two sutures, the devices 100/200 can be used in some embodiments to place a single suture through both the septum primum 404 and the septum secundum 406, or to place multiple sutures through each of the septum primum 404 and the septum secundum 406. In some embodiments, plural devices 100, plural devices 200, or both can be used to place multiple sutures through one or both of the septum primum 404, the septum secundum 406, or other biological tissue, biological structure, prosthetic, or synthetic material or implantable device in the body. For example, plural devices may be used to suture a prosthetic heart valve to the heart or to affix a balloon, umbrella, or other device that is not properly positioned to the surrounding tissue.

Further details on the methodology for using suturing devices 100/200 can be found in U.S. Pat. No. 9,131,938, filed Feb. 7, 2013, the entirety of which is hereby incorporated by reference in its entirety.

Multi-Armed Suturing Device

Figure 6B:
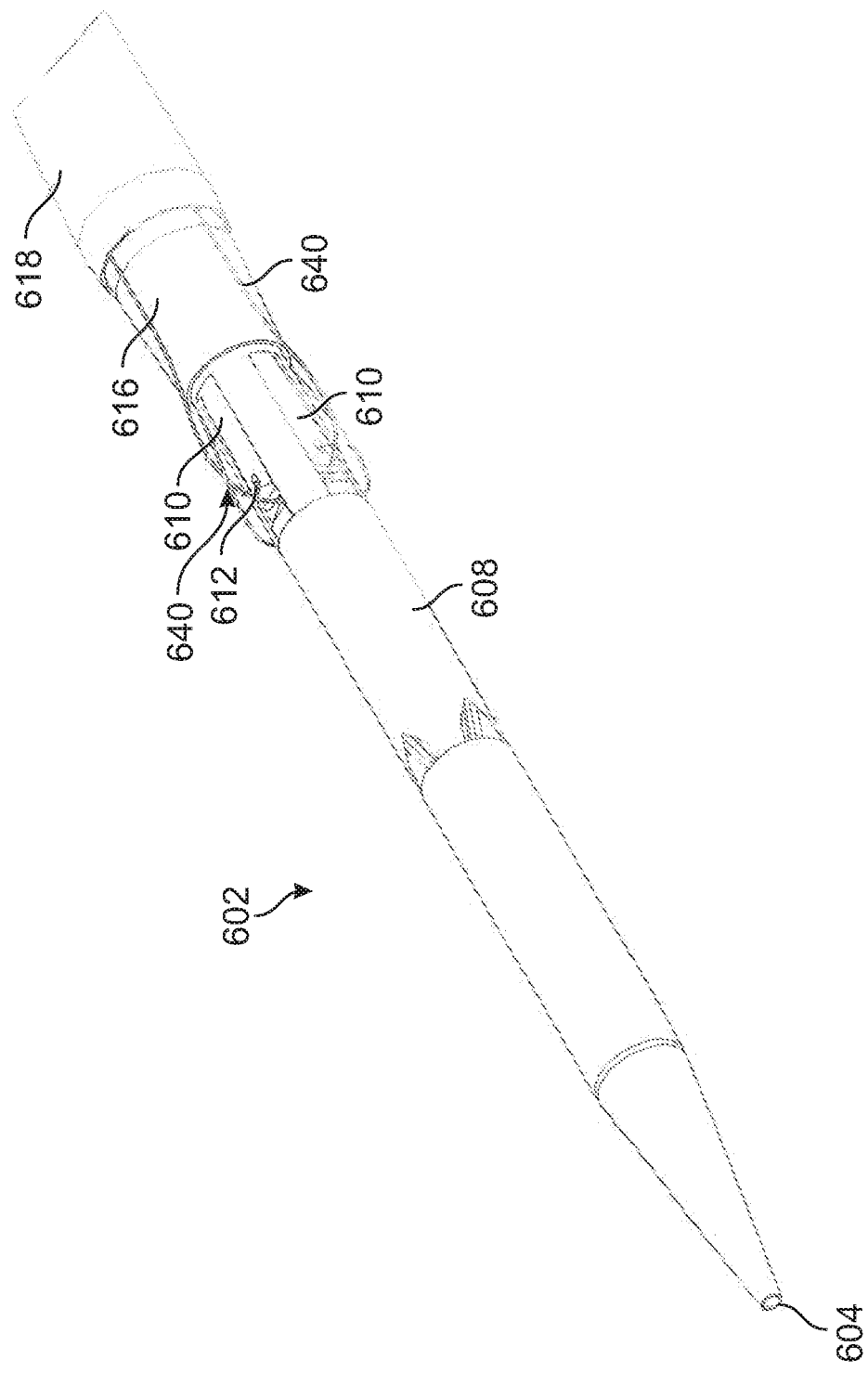

FIGS. 6A-B illustrate perspective views of another embodiment of a suturing device 600. FIG. 6A is an embodiment of the entire device, and FIG. 6B illustrates a section of a distal assembly of the device. The device can be used, for example, to insert sutures through the outer wall of a heart in anticipation of a surgical procedure within the heart. The device has a proximal and a distal end. At the distal end, the device can have a guide wire lumen 604, which can allow the device to follow a guide wire to a desired position. However, in some embodiments a guide wire may not be used. At the proximal end, the suturing device can comprise one or more handles 606 with various mechanisms that can be used to control the elements of the distal assembly. Further details regarding handles and associated components, including actuator rods, are provided in U.S. Pat. No. 8,246,636, published on filed on Feb. 12, 2013, which is hereby incorporated by reference herein in its entirety.

The device can comprise an elongate body 608 (e.g., elongate tubular member, elongate member) which can include a plurality of suture clasp arms 610. The elongate body 608 can include one or more elongate members between the handle 606 and the distal end of the assembly (e.g., attached end to end or an elongate body within the lumen of another elongate body). The suture clasp arms 610 can move from a retracted position, as illustrated, in which the suture arms are at least partially within the elongate body 608, to an extended position, described and illustrated below in which the suture arms extend outward from the elongate body. The suture arms can also be positioned at varying angles from each other around the circumference of the elongate body. The illustrated embodiment has four suture clasp arms 610 spaced 90 degrees apart. In some embodiments, there may be more suture arms spaced varying degrees apart. In some embodiments, there may be just one suture arm, which can be rotated about an opening in the heart to place multiple sutures around the opening. For purposes of closing the opening, it can be advantageous to have an even number of suture arms, such as 2, 4, 6, or 8, each suture arm part of a pair with another suture arm spaced 180 degrees apart around the circumference of the elongate body. In some embodiments, the device can also have an odd number of suture arms. If just a single suture arm is used to position multiple sutures around the opening, the sutures can be positioned in pairs spaced 180 degrees apart around the opening.

The suture clasp arms 610 can comprise one or more suture mounts or clasps 612 at a distal end. The suture clasps 612 can be adapted to releasably retain a suture portion 614. In some embodiments, the suture clasps can releasably retain a suture portion 614 while the suture clasp arms 610 are in the retracted position and in the extended position. In some embodiments, a suture end may be retained in the suture clasps. In some embodiments, the suture clasps may retain a portion of suture that is not the suture end.

When the device is assembled, it can be pre-loaded with a first sheath 616 (for example an 18 French sheath, though other sizes can be used as well) that surrounds at least a portion of the elongate body and a second sheath 618 surrounding at least a portion of the first sheath 616. In some embodiments, as illustrated, a distal end of the first sheath 616 can extend to a position just proximal to the suture clasp arms 610, thereby allowing the suture clasp arms 610 to move into the extended position or into the retracted position, though the first sheath 616 can be substantially proximal to the suture clasp arms 610 as well. The suture portions 614 can run outside of the first sheath 616 and through the second sheath 618 to a position proximal to at least the second sheath 618. The second sheath can help confine the suture portions such that they do not get tangled or otherwise interfere with a procedure, described below. In some embodiments, the second sheath 618 is shorter than first sheath 616. In some embodiments, the second sheath 618 can be a peel-away (or peelable) sheath that can be removed from around the first sheath 616 and around the suturing device 600. In some embodiments, the device may not include a first sheath 616 and may only include the second sheath 618.

The device 600 can also include suture catch mechanisms (referred to herein as needles), described below, that can retrieve sections of suture from the suture clasps 612. In some embodiments, the device can include one or more needle exit channels 620, from which the needles can exit an interior of the elongate body 608 in order to reach the suture clasps 612. In some embodiments, there can be an equal number of needle exit channels 620 as there are suture clasp arms 610, and the needle exit channels can be configured to align with a corresponding suture clasp arm 610.

Figure 7:
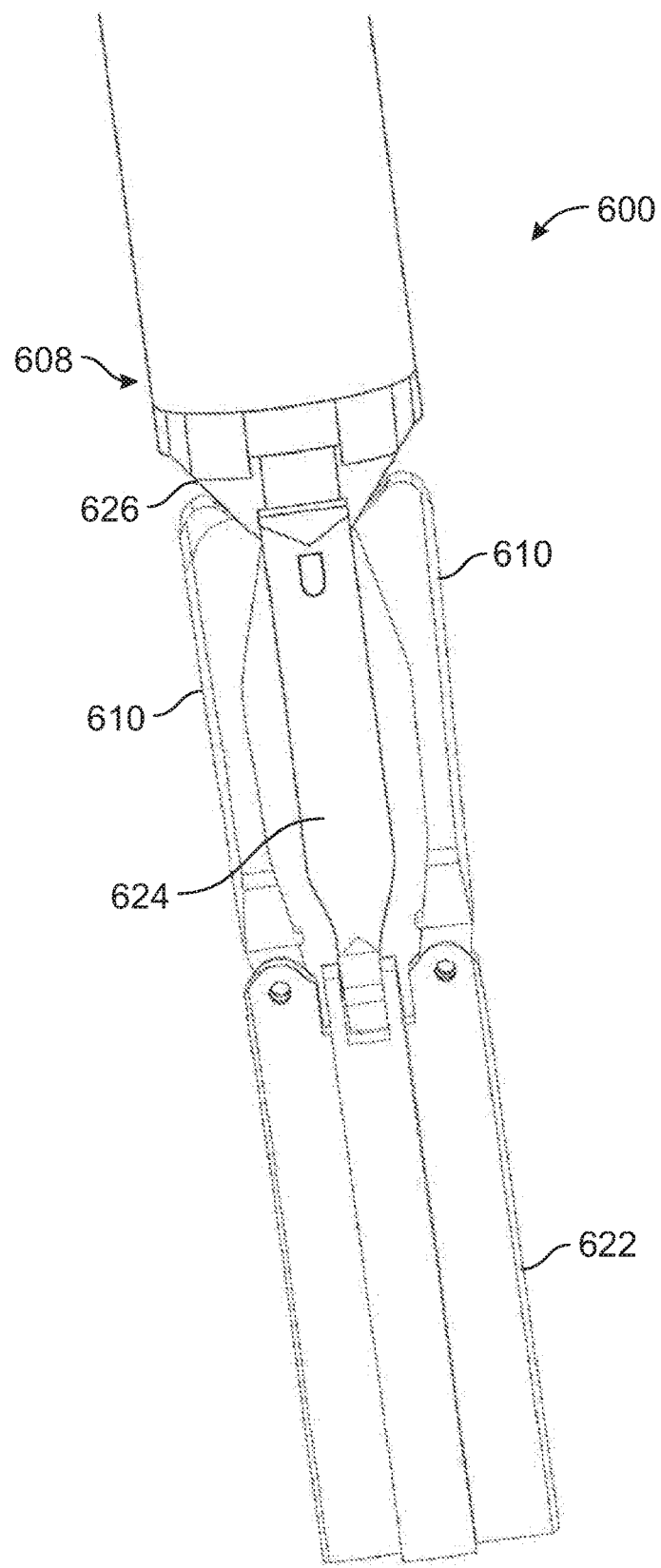
FIG. 7 illustrates a perspective view of a multi-armed suturing device showing suture arms in a retracted position with certain external components not illustrated.
Figure 8:
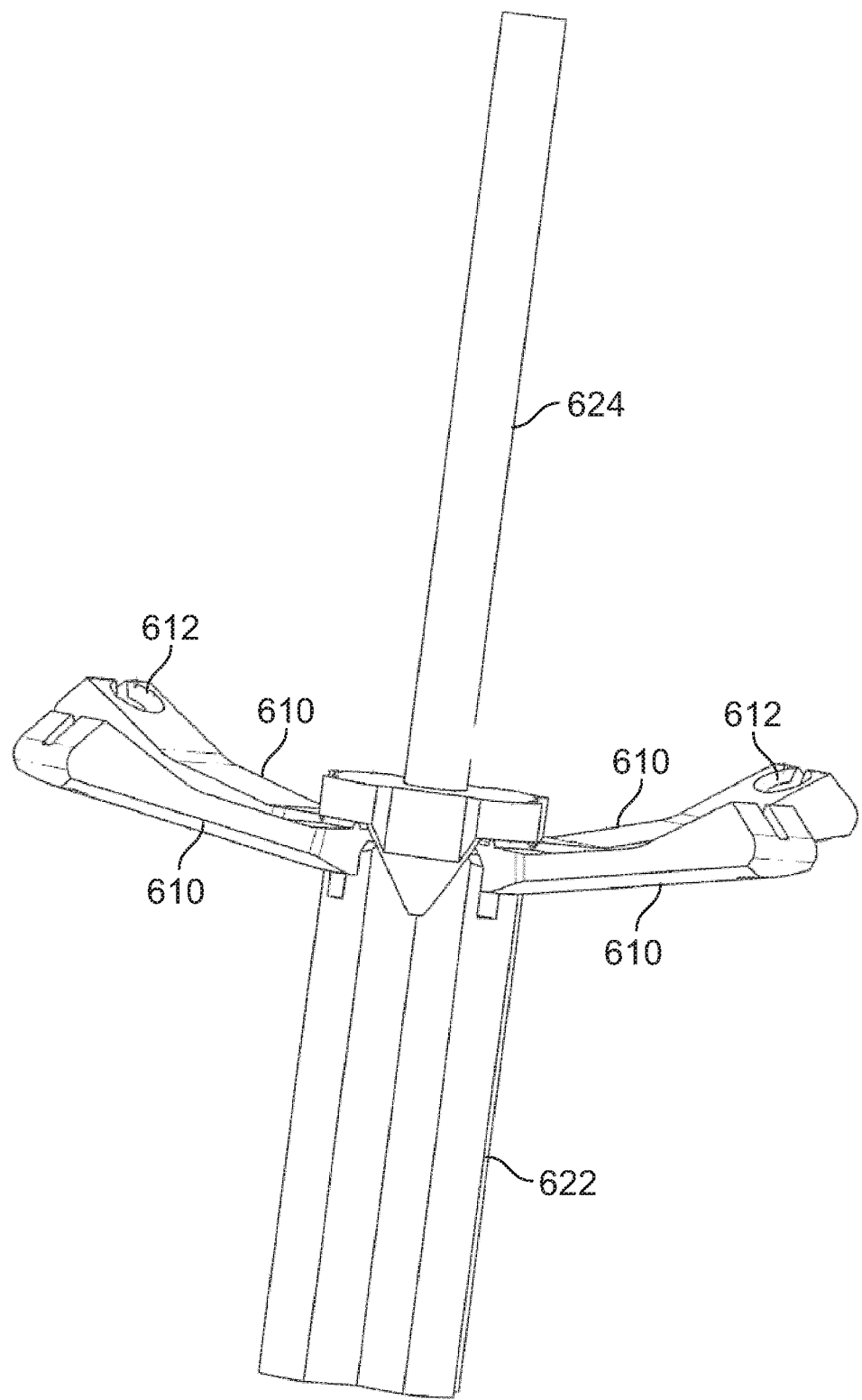
FIG. 8 illustrates a perspective view of a multi-armed suturing device showing suture arms in a deployed position with certain external components not illustrated.

FIGS. 7 and 8 illustrate the suture clasp arms 610 in more detail. FIG. 7 is a perspective view of a portion of the device with certain external components not illustrated in order to improve visibility. The device can have a suture arm driver 622, to which the suture clasp arms 610 can rotatably attach at a first end thereof. The suture clasp arms 610 can be free at a second end opposite the first end, allowing the second end to swing outward such that the suture clasp arms 610 can move from the retracted position to the extended position, or to swing inward such that the suture clasp arms 610 can move from the extended position to the retracted position.

As illustrated, the suture clasp arms 610 can rotate about a proximal end of the suture clasp arms 610. In some embodiments, the suture clasp arms 610 can slide or move in other ways from the retracted to the extended position, or from the extended to the retracted position. In the illustrated embodiment, as the suture clasp arms 610 rotate from the extended to the retracted position, the suture clasps 612 will move toward a distal end of the suturing device. In some embodiments, the suture clasp arms 610 can be configured such that the suture clasp moves distally as the suture clasp arms 610 rotate from the retracted to the extended position. In some embodiments, the suture clasp arms 610 can rotate about a distal end of the suture clasp arms 610.

In some embodiments, as illustrated in FIG. 7, the suture arm driver 622 can translate along a central shaft 624. As it translates it can move the suture clasp arms 610 with it. In some embodiments, the suture arm driver 622 can translate far enough such that the suture clasp arms 610 can contact a section 626 of the elongate body 608, as illustrated. In some embodiments, the section 626 of the elongate body contacted by the suture clasp arms 610 can be angled. The ends of the suture clasp arms 610 opposite the suture arm driver 622 can also have an angled surface, and as the suture arm driver 622 moves farther toward the section 628 the suture clasp arms 610 will be pushed outward toward the extended position. To move the suture clasp arms 610 from the extended position to the retracted position, the suture arm driver 622 can translate along the central shaft 624 in the opposite direction, and the suture clasp arms 610 can return to the retracted position.

FIG. 8 is a perspective view of a section of the distal assembly with certain external components not illustrated in order to improve visibility. FIG. 8 illustrates one embodiment of the suture clasp arms 610 in an extended position. In some embodiments, the suture clasp arms 610 can be generally straight. In some embodiments, the suture clasp arms 610 can extend from the elongate body at approximately 90 degrees. In some embodiments, the suture arms can extend from the elongate body at an angle less than 90 degrees or greater than 90 degrees. In some embodiments, the suture clasp arms 610 can have angled or curved segments, and can extend from the elongate body at a first angle and have other sections at other angles relative to the elongate body. In some embodiments, the suture clasps 612 can be on a section of the suture clasp arms 610 that is at an angle relative to the elongate body that is different from the first angle.

In some embodiments, the needles can be located distal to the suture clasp arms 610 and point proximally toward the suture clasp arms 610. In some embodiments, the needles can be located proximal to the suture clasp arms 610 and point distally toward the suture clasp arms 610. The needles 630 can attach to a needle drive tube 632, which can be positioned around the central shaft 624 and which can translate along the central shaft 624. In some embodiments, a collar can be used to lock the needles 630 to the needle drive tube 632.

The needle drive tube 632 can move the needles toward or away from the suture clasp arms 610. As the drive tube moves the needles toward the suture clasp arms 610 the needles will eventually reach the needle exit channels 620 (visible in FIG. 6B). The needle exit channels can be angled to direct the needles toward the suture clasp arms 610, and specifically the suture clasps 612.

Figure 9A:
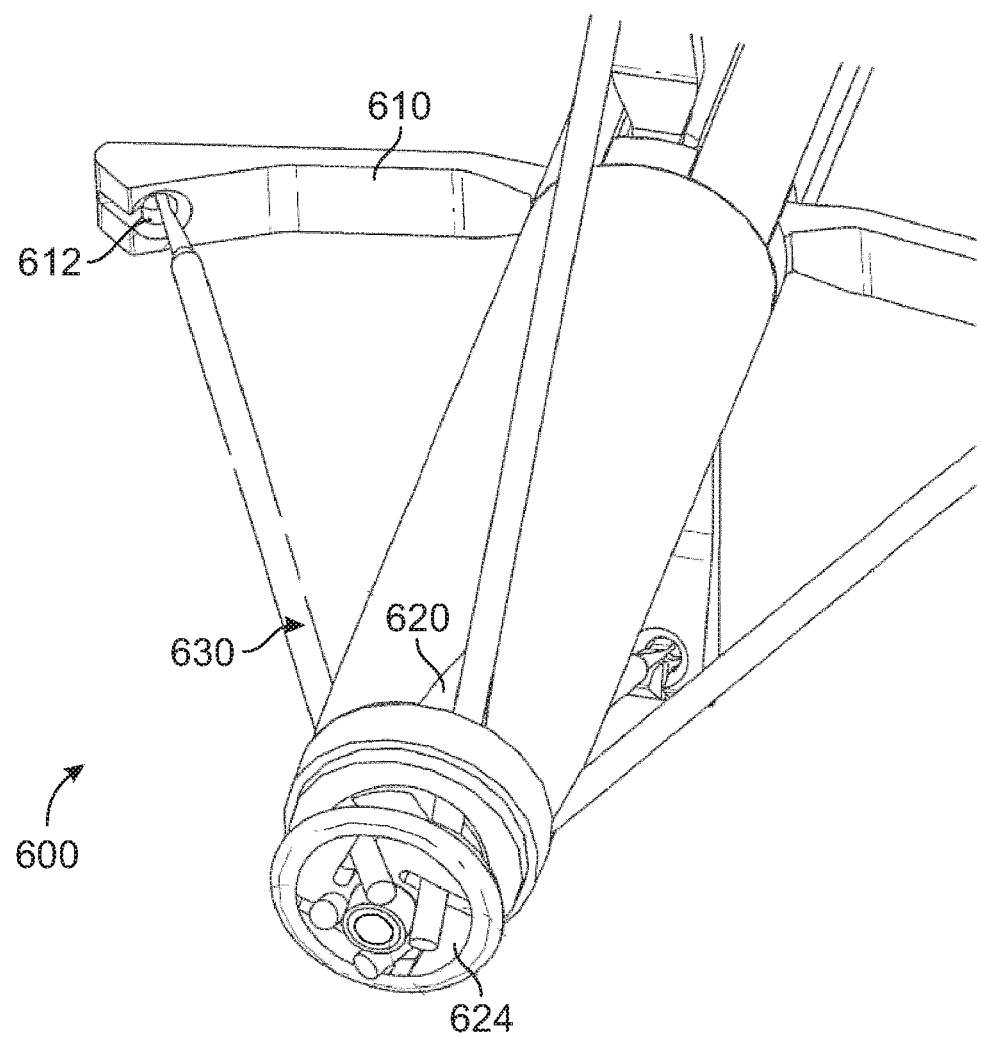
FIGS. 9A-B show a perspective view of an embodiment of a multi-armed suturing device.
Figure 9B:
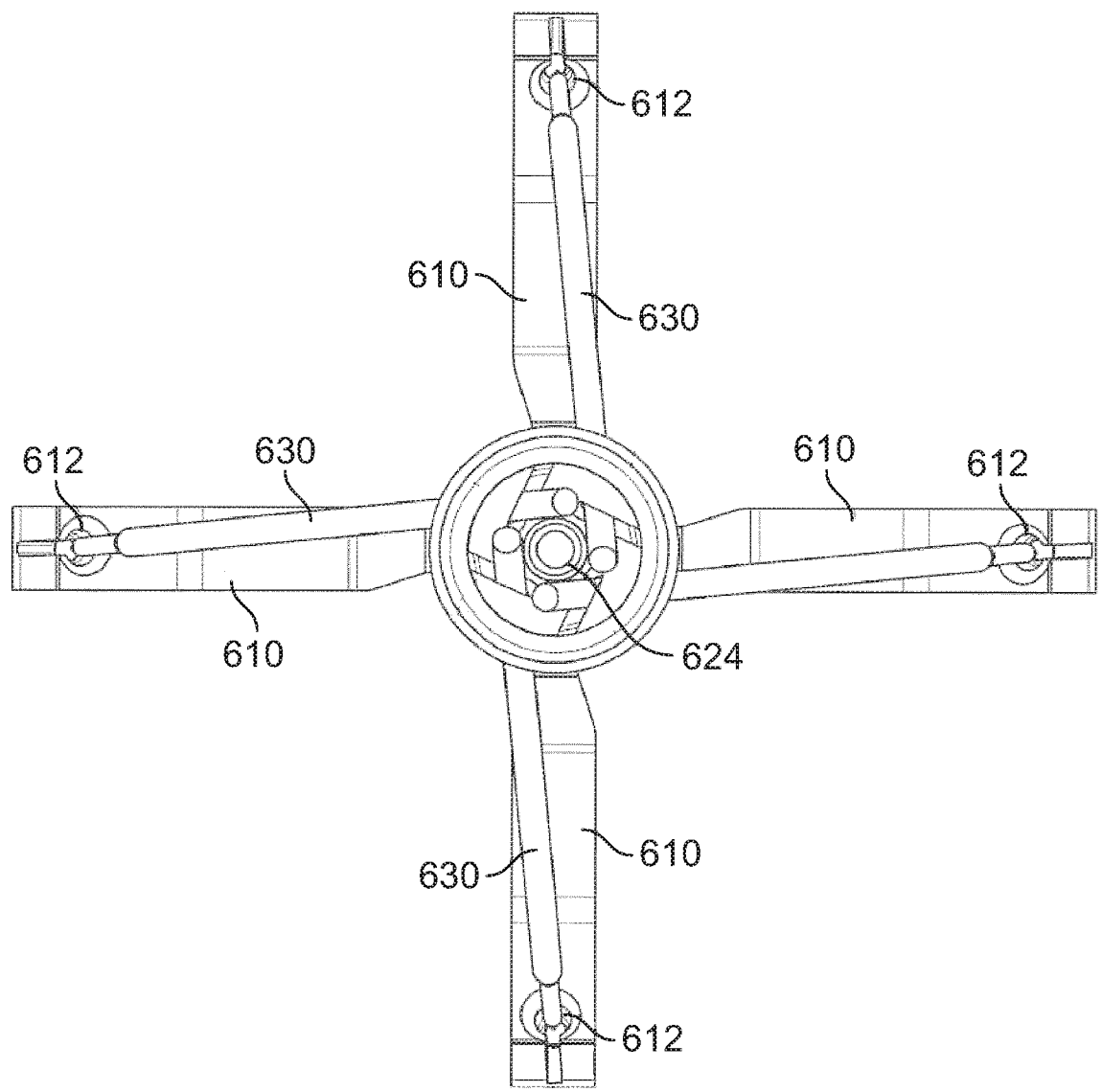

FIG. 9A is a perspective view of a section of the distal assembly with various components removed for visibility. FIG. 9B is a top view of the section shown in FIG. 9A. As illustrated, the suture clasp arms 610 can extend radially outward along a line passing through the longitudinal axis of the distal assembly. As illustrated in FIG. 9A, the needle exit channels 620 can spaced or offset from a plane defined by an extended suture clasp arm 610 and the longitudinal axis of the distal assembly, so that the needle 630 extends at an angle to this plane and intersects the plane at suture mount 612. However, the needles 630 and extended suture clasp arms 610 can be aligned. In some embodiments the suture clasp arms 610 can be symmetrically spaced about the distal assembly. In embodiments with four suture clasp arms 610, as illustrated, they can be spaced 90 degrees apart from each other when extended.

FIGS. 9A and 9B illustrates the needles 630 in a deployed position in which a distal tip of each needle is within a suture mount 612. In some embodiments, moving away from the suture clasp arms 610 can be in the distal direction. In some embodiments, moving away from the suture clasp arms 610 can be in the proximal direction. In some embodiments, the needles can move to a retracted position in which they are entirely or substantially within the elongate body.

Methods of Use of Four Arm Suture Device

FIGS. 10A-10J illustrate one method of using the suturing device 600 to place sutures through tissue near an opening in the heart and to position a sheath through the opening to allow for entry of other devices, while maintaining or nearly maintaining haemostasis. The suturing device can have a guide wire lumen, not illustrated, that can allow the suturing device to follow a guide wire 702 into a position within the heart. In a typical procedure, a hollow needle (delivered, for example, through a trocar into the thoracic cavity) can be used to puncture an opening at or near the apex of the heart and to feed a guide wire through the opening and into the heart. The suturing device can then follow the guide wire into the opening and into the heart. The suturing device can have a tapered end at the distal end of the elongate body 608, as illustrated in FIG. 7, and the taper can be configured such that the device is capable of following the guide wire through the opening formed by the needle, widening the opening as the device is advanced further into the heart. The device can then be used to place a plurality of sutures through the tissue of the heart near the opening. The device can then be removed, leaving the sutures in place. In some embodiments, the first sheath can also be left within the opening in the heart, thereby allowing other devices to be inserted through the sheath to perform a desired procedure within the heart. The sutures can then be used to tighten the opening closed after the desired procedure has been performed and while the sheath and/or device is being removed.

Figure 10A:
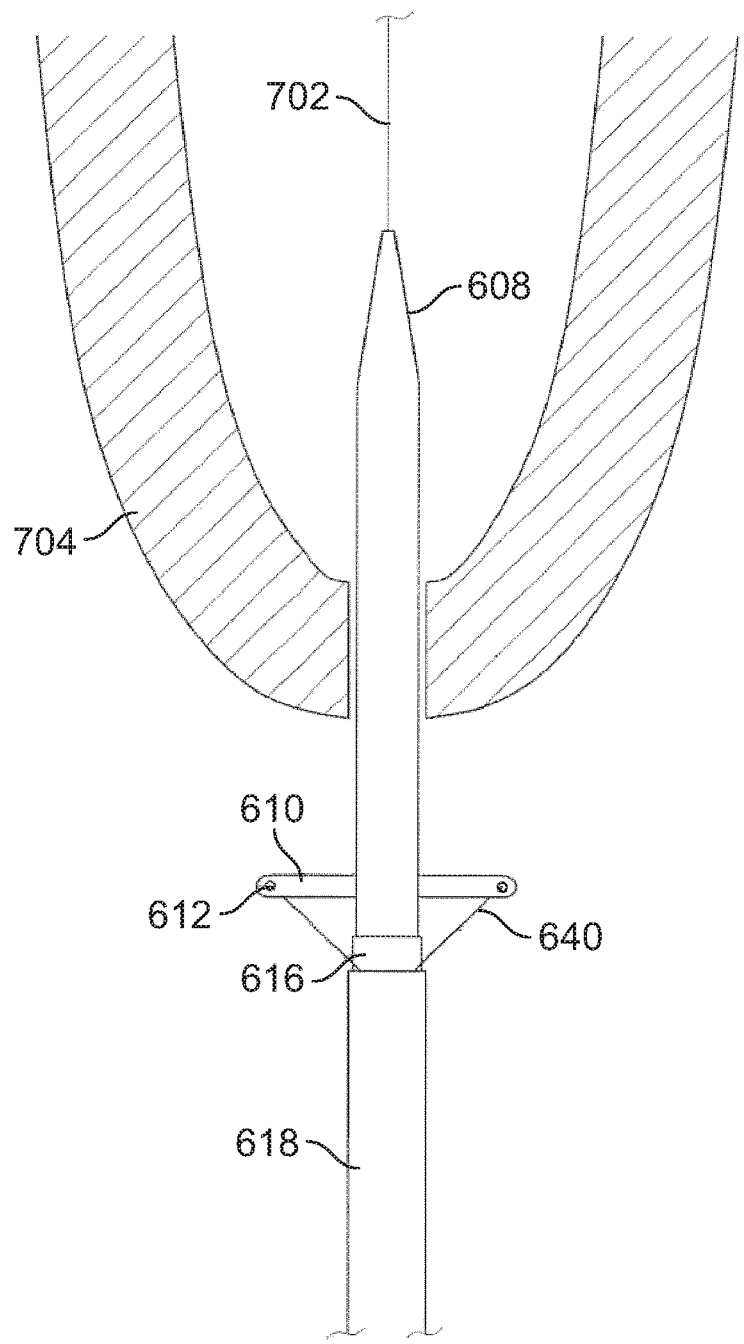
FIGS. 10A-J show a cross sectional schematic representation of an embodiment of a procedure using a multi-armed suturing device suturing an apex of the heart.

FIGS. 10A-10J illustrate one method of using the suturing device 600 to place sutures through tissue near an opening in the heart and to position a sheath through the opening to allow for entry of other devices, while maintaining or nearly maintaining haemostasis. As discussed above, the device 600 can follow a guide wire 702 through a puncture in or near the apex of a heart, the tapered end of the device widening the opening in the heart wall 704, as the device enters further into the heart. The suture clasp arms 610 can be moved into an extended position, as shown in FIG. 10A. FIGS. 10A-J show a cross sectional view of the heart, and only show the two suture clasp arms 610 of the device that lie in the illustrated planes. Although the method illustrated in FIGS. 10A-J can be performed with a device having only the two illustrated arms, the description of the method will be with reference to the device of FIGS. 6A-B, which has four arms. Each suture clasp arm 610 holds a separate suture 640, so there are a total of four separate sutures when the device is positioned.

Figure 10B:
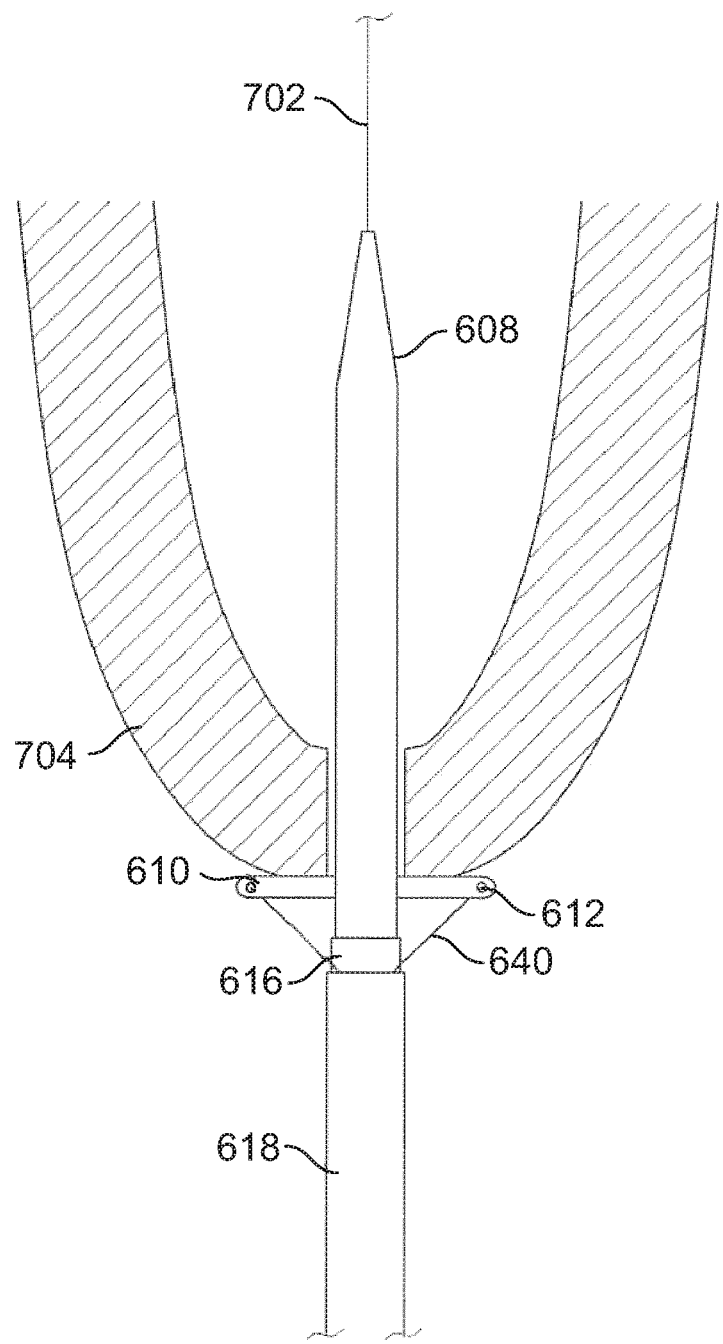
Figure 10C:
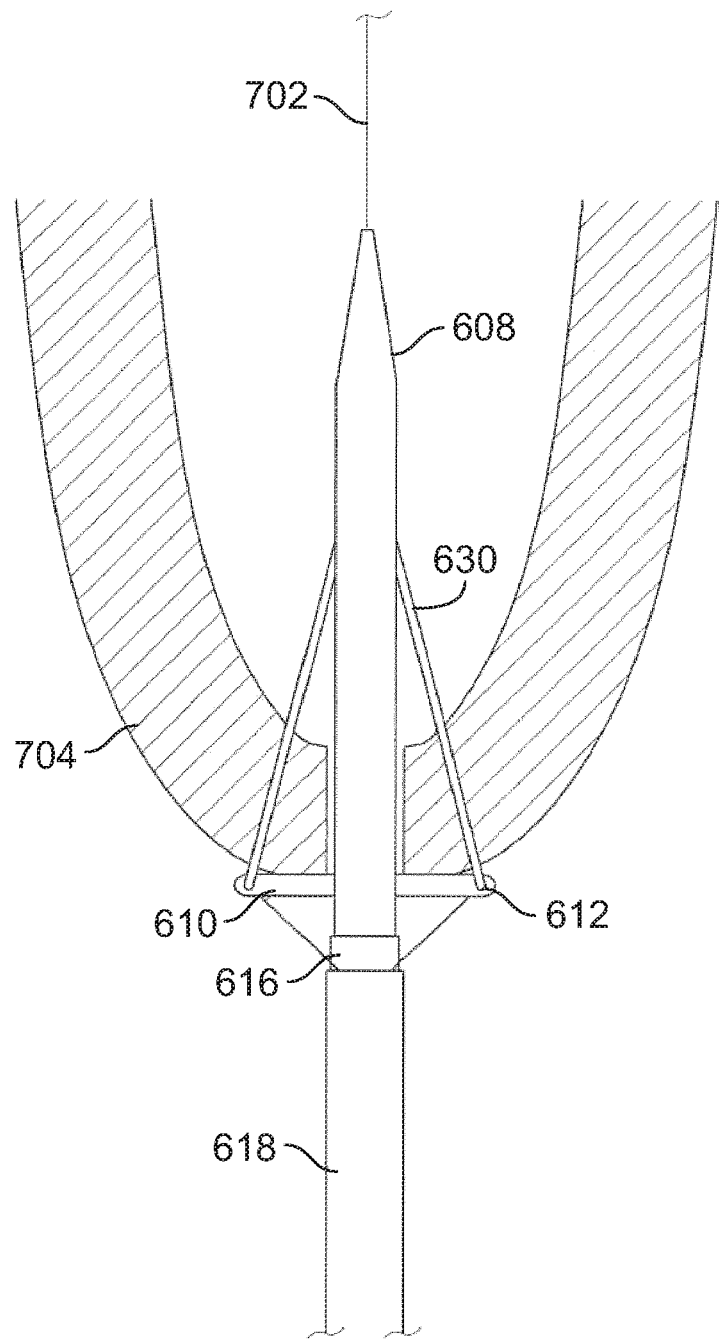
Figure 10D:
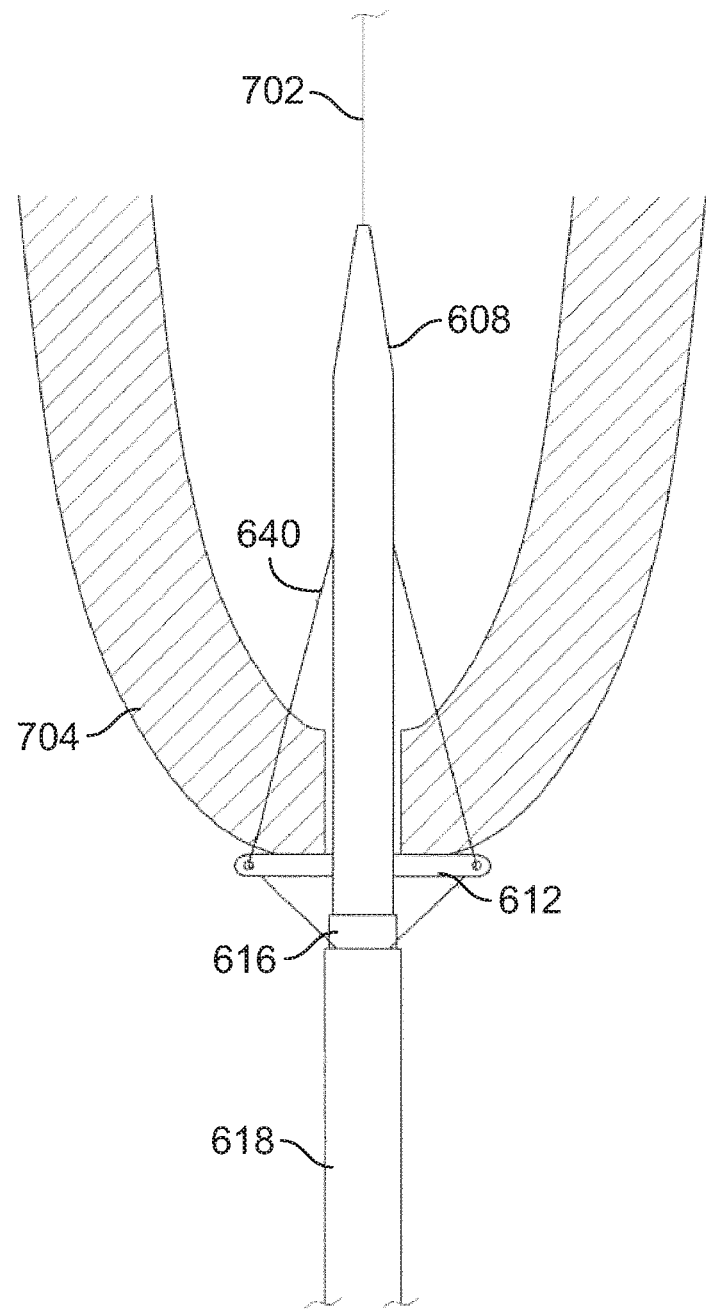

With the suture clasp arms 610 in the extended position, the device can be further advanced into the heart until the suture clasp arms 610 press against tissue of the heart, as shown in FIG. 10B. Once in position at the base of the heart, needles 630 can fire and extend from a distal end of the elongate body 608, through tissue of the heart, and into the suture clasps 612, as illustrated in FIG. 10C. In some embodiments, the device can have a needle 630 that corresponds to each suture clasp arm 610, a needle that corresponds to multiple suture clasp arms 610, or multiple needles that correspond to a single suture clasp arm 610. The needles can engage the sutures 640, releasably positioned in the suture clasp 612, such that when the needles 630 retract back into the elongate body 608 they draw a portion of suture 640 with them, as shown in FIG. 10D. In some embodiments, the needles 630 can fire simultaneously, and in some embodiments they can fire sequentially.

Figure 10E:
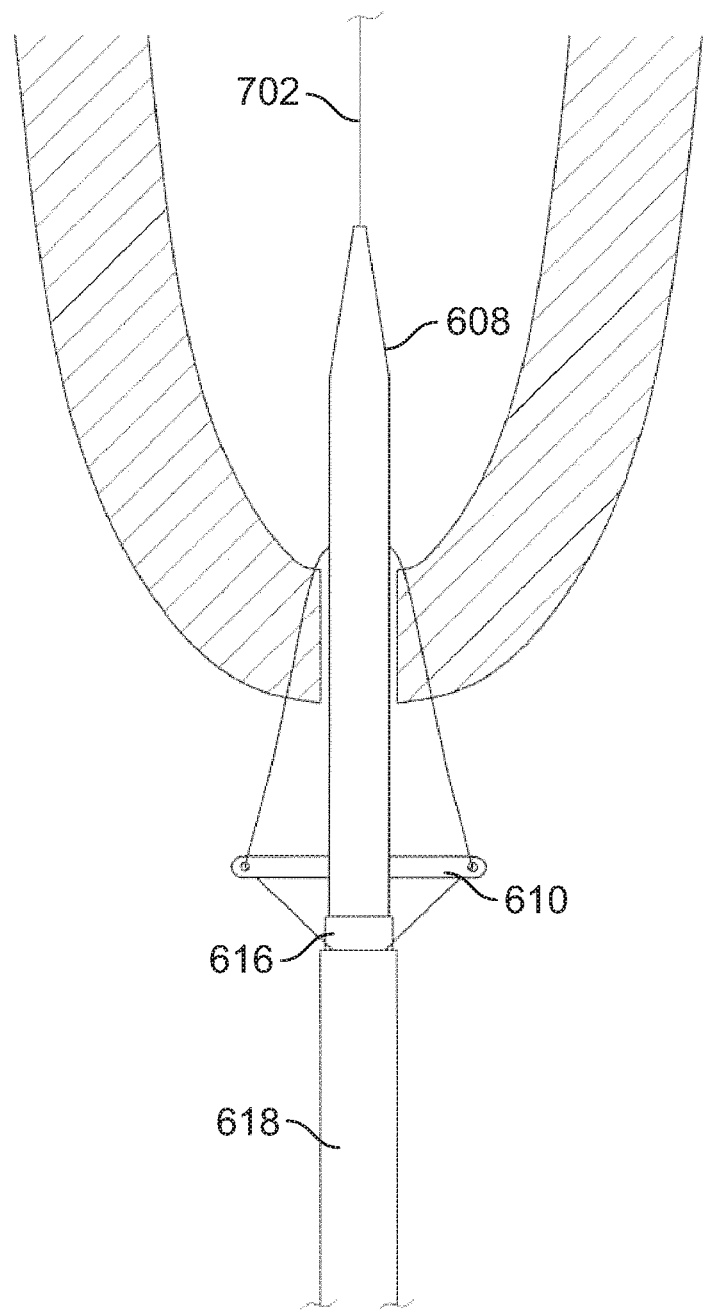
Figure 10F:
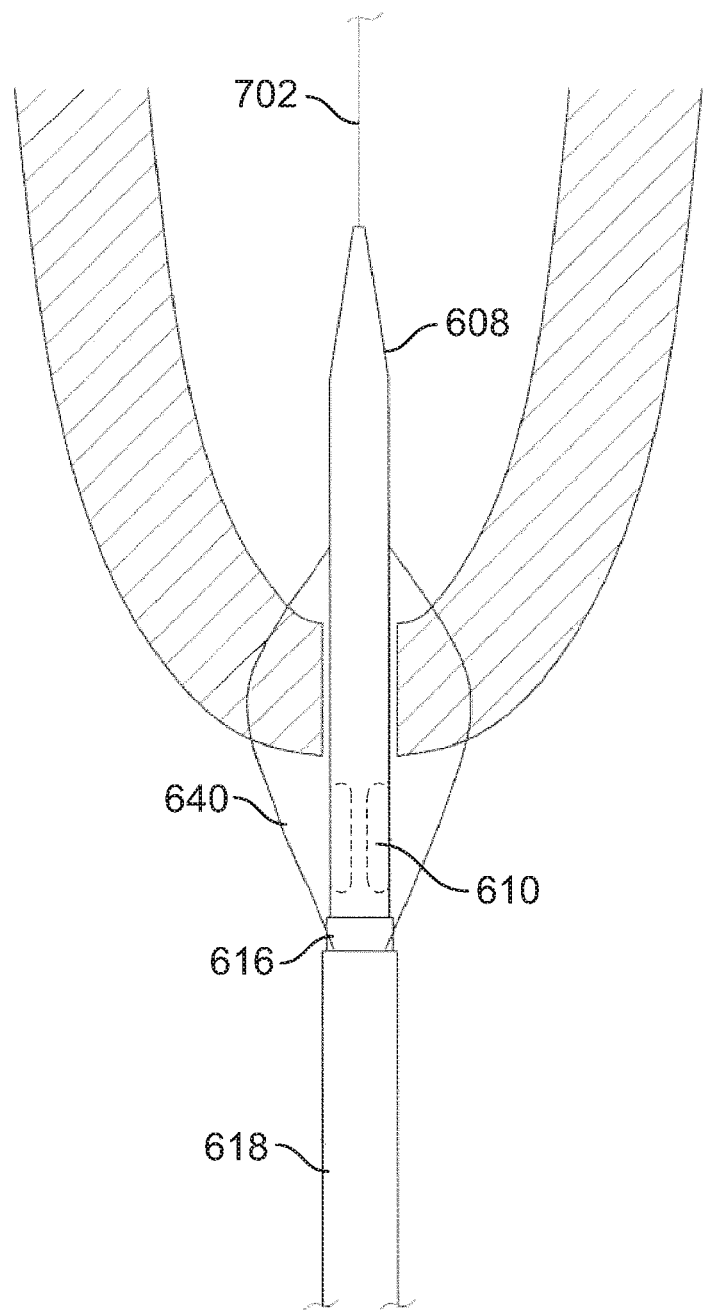
Figure 10G:
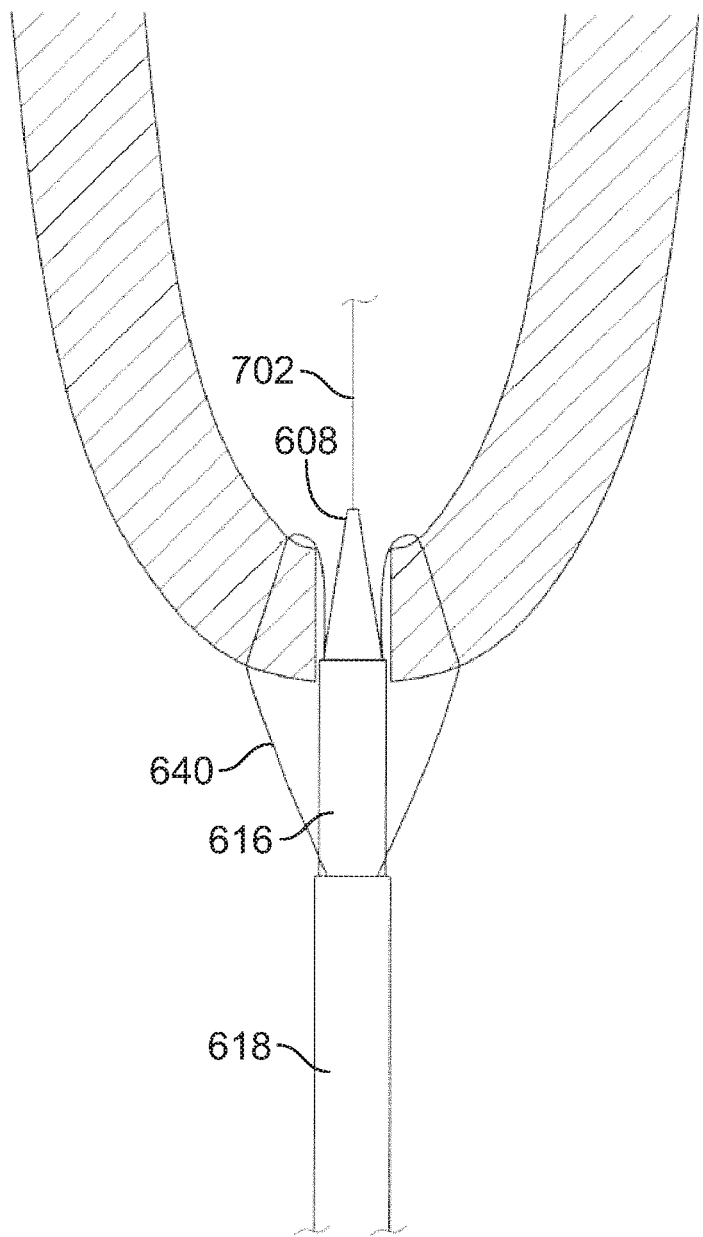

Once the needles have fired and drawn sutures through tissue of the heart, the device can be withdrawn slightly from the heart in order to allow the suture clasp arms 610 to return to a retracted position, as shown in FIG. 10E. In embodiments where the distal ends of the suture clasp arms 610 move proximally as the suture clasp arms 610 rotate from an extended to a retracted position, it may not be necessary to withdraw the device prior to retracting the suture clasp arms 610. Once the suture clasp arms 610 have been retracted, as shown in FIG. 10F, the sutures 640 will run from within the device, through the tissue of the heart, and to a proximal end of the device while passing beneath the second sheath 618 but over the first sheath 616, as shown in FIG. 10F. If a first sheath 616 is used, the first sheath 616 can then be moved into the opening in the heart while the elongate body 608 is withdrawn, as illustrated in FIG. 10G. In some embodiments, the sheath can fully pass into the opening before the elongate body has begun to be withdrawn. In FIG. 10G, the sheath has begun to be advanced into the opening of the heart while the elongate body has begun to be withdrawn.

Figure 10H:
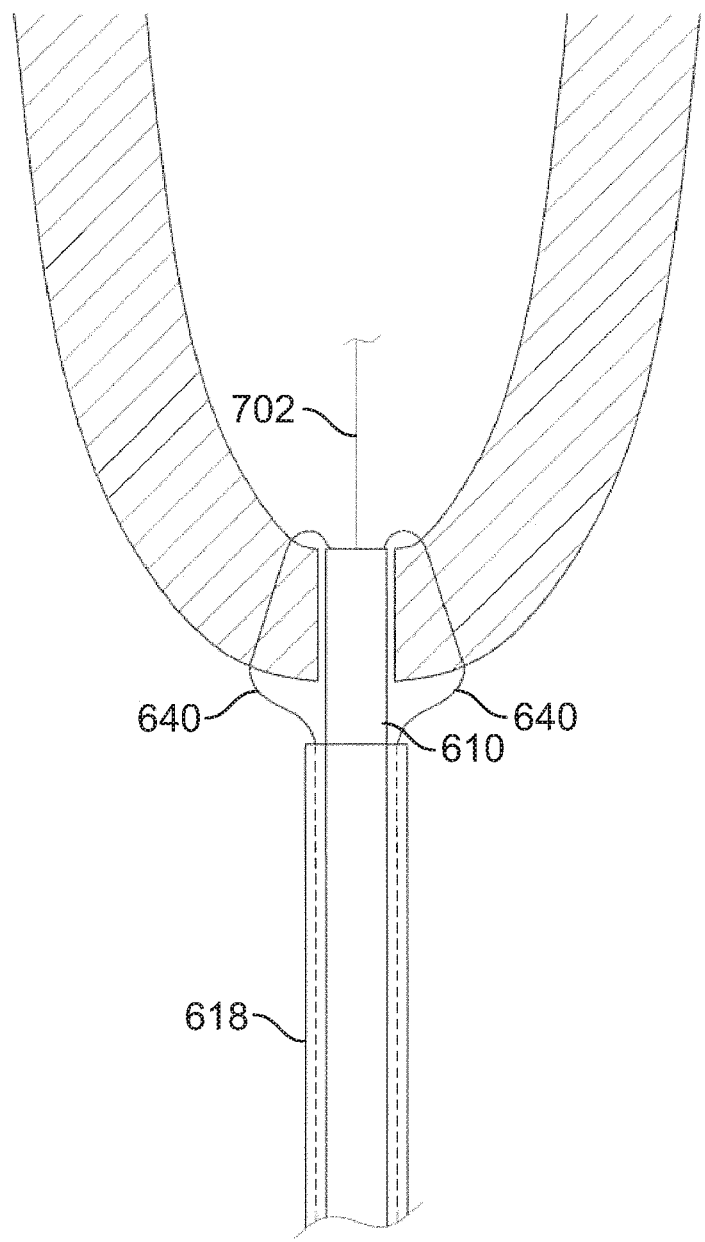
Figure 10I:
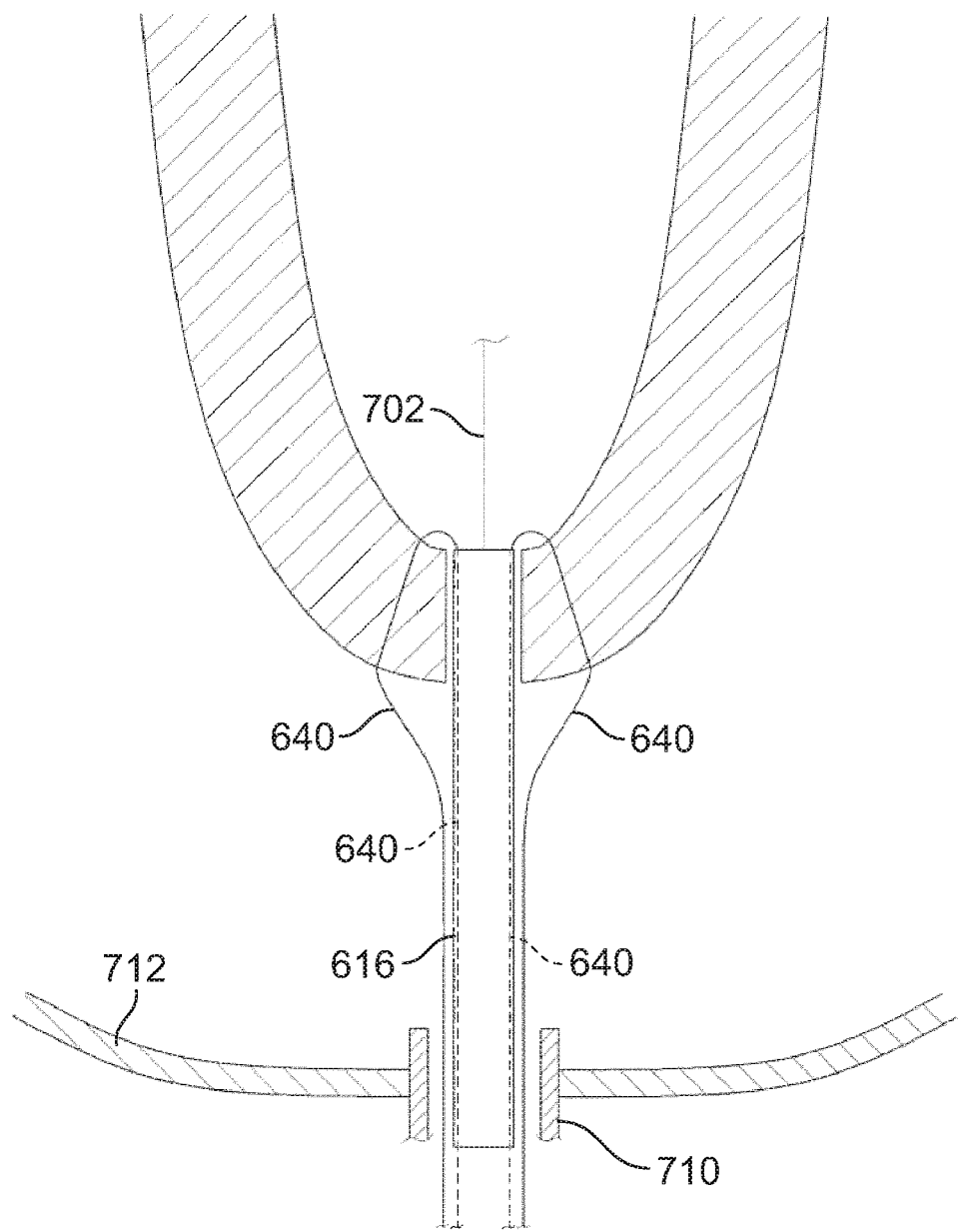

In FIG. 10H, the first sheath 616 has been fully advanced into the opening of the heart and the elongate body has been withdrawn. In some embodiments, the first sheath 616 can have a hemostatic valve (not illustrated) that can prevent extraneous bleed back, and in some embodiments the valve can be at a proximal end of the first sheath 616. The suture ends that were within the elongate body now pass through the first sheath 616 and run to a proximal position outside of the patient where they can be manipulated, as shown in FIG. 10I. From the proximal position of those suture ends, the sutures run through the sheath and into the heart, through tissue of the heart, and back to the proximal position while remaining outside of the first sheath 616 and inside of the second sheath 618. The second sheath 618 has been illustrated wider than in previous figures in order to improve visibility of sutures 640 running between the first and second sheaths. In some embodiments, the second sheath 618 can be wider or narrower in order to have a looser or tighter fit around the first sheath 616, and the first sheath can be wider or narrower in order to have a looser or tighter fit around the elongate body.

In FIG. 10I, the second sheath 618 has been removed from around the first sheath 616 (e.g. by peeling it off), and the portions of the sutures 640 within the first sheath 616 are illustrated. FIG. 10I also illustrates the proximal end of the first sheath 616, which can be extending through a trocar 710 positioned through the chest wall 712. Each suture 640 has a free end at the proximal position outside of the patient that passes through the first sheath 616, into the heart, through tissue of the heart, and back to the proximal position while remaining outside of the first sheath 616. Thus, there are four suture ends that pass through the first sheath 616 and four suture ends that pass outside of the first sheath 616. The guide wire 702 also passes through the first sheath 616, but it is not shown within the first sheath in FIG. 10I for the sake of clarity.

Figure 10J:
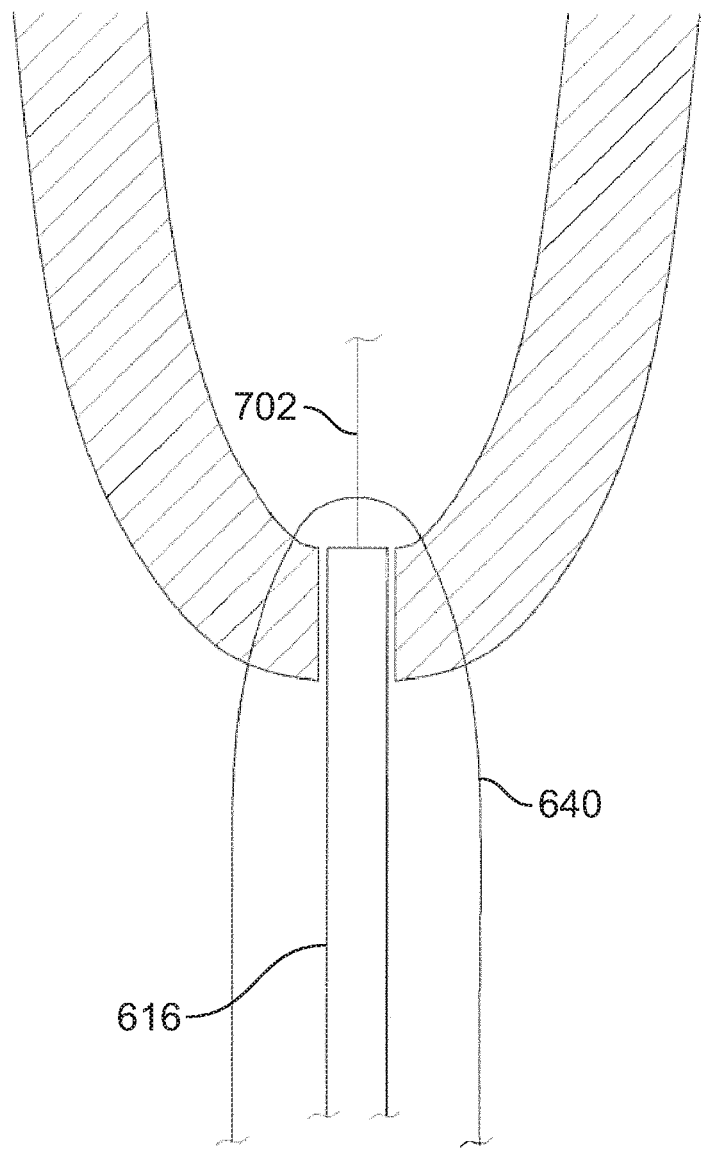

Suture ends that pass through the first sheath 616 can be secured together with a knot or other device. Further details regarding a device for joining sutures are provided in U.S. Pat. App. Pub. No. 2011/0190793, filed on Jan. 28, 2011, which is hereby incorporated by reference herein in its entirety. In some embodiments, suture ends that pass through the first sheath 616 can be secured together in pairs, each pair having suture ends that had been releasably attached to suture clasp arms 610 spaced 180 degrees about the circumference of the elongate body 608 of the device 600. By then pulling on one or more of the remaining free suture ends, the joined suture 640 can be pulled through the first sheath 616 and into the heart, as illustrated in FIG. 10J. FIG. 10J only shows one suture, but when the two pairs of suture ends that pass through the first sheath 616 have been secured together and pulled into the heart, a second suture would pass through the heart in the plane substantially perpendicular to the illustrated cross section.

In some embodiments, the point where a pair of suture ends has been joined together can be passed through the tissue of the heart and outside of the heart by pulling on one of the remaining free suture ends. In some embodiments, prior to joining the two suture ends that pass through the first sheath, a pledget can be slidably attached to a suture end, such as by threading a suture end through a hole in the pledget. After the two suture ends that pass through the first sheath have been secured together, the joined suture can be pulled through the tissue of the heart by one of the remaining free ends until the pledget contacts an inner surface of the heart wall, where it may remain. In some embodiments, prior to or after joining the two suture ends within the sheath, a pledget can be attached to a free suture end that passes outside of the first sheath 616. With the two suture ends within the first sheath joined, the opposite free suture end can be pulled until the pledget contacts an outer surface of the heart, where it may remain.

Suture Spool

Figure 11A:
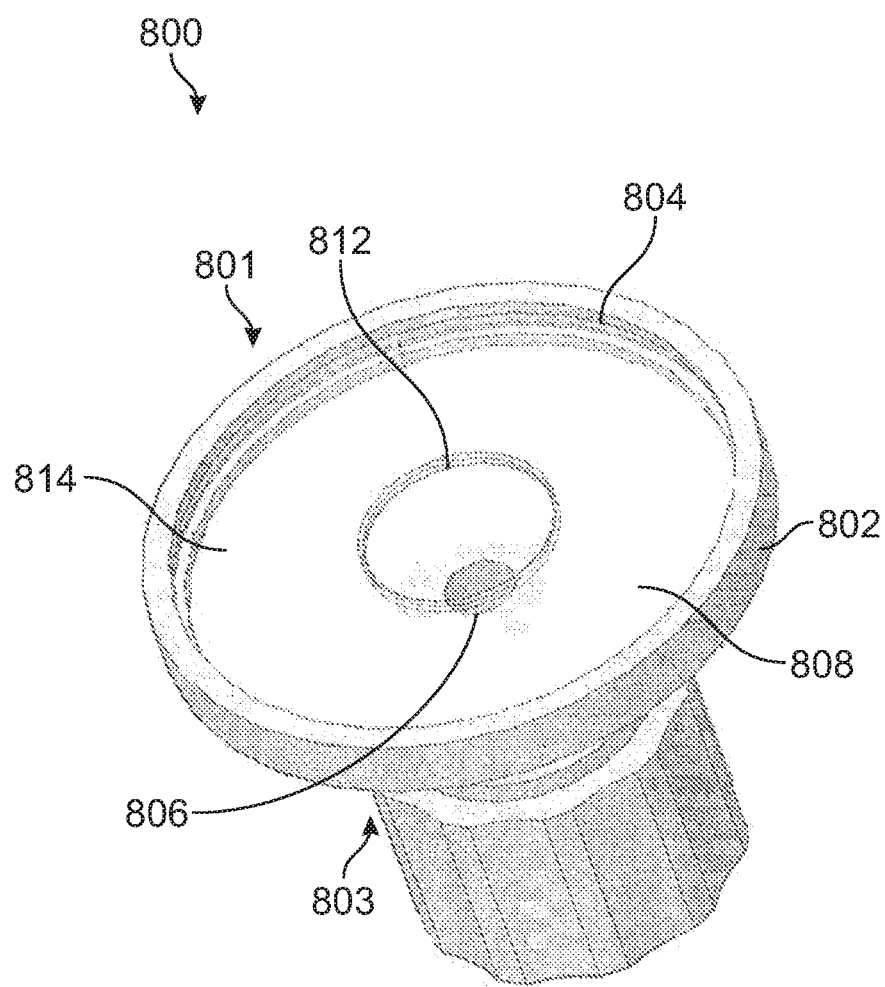
FIGS. 11A-C illustrate a top perspective view, side view, and bottom perspective view, respectively, of an embodiment of a suture spool.
Figure 11B:
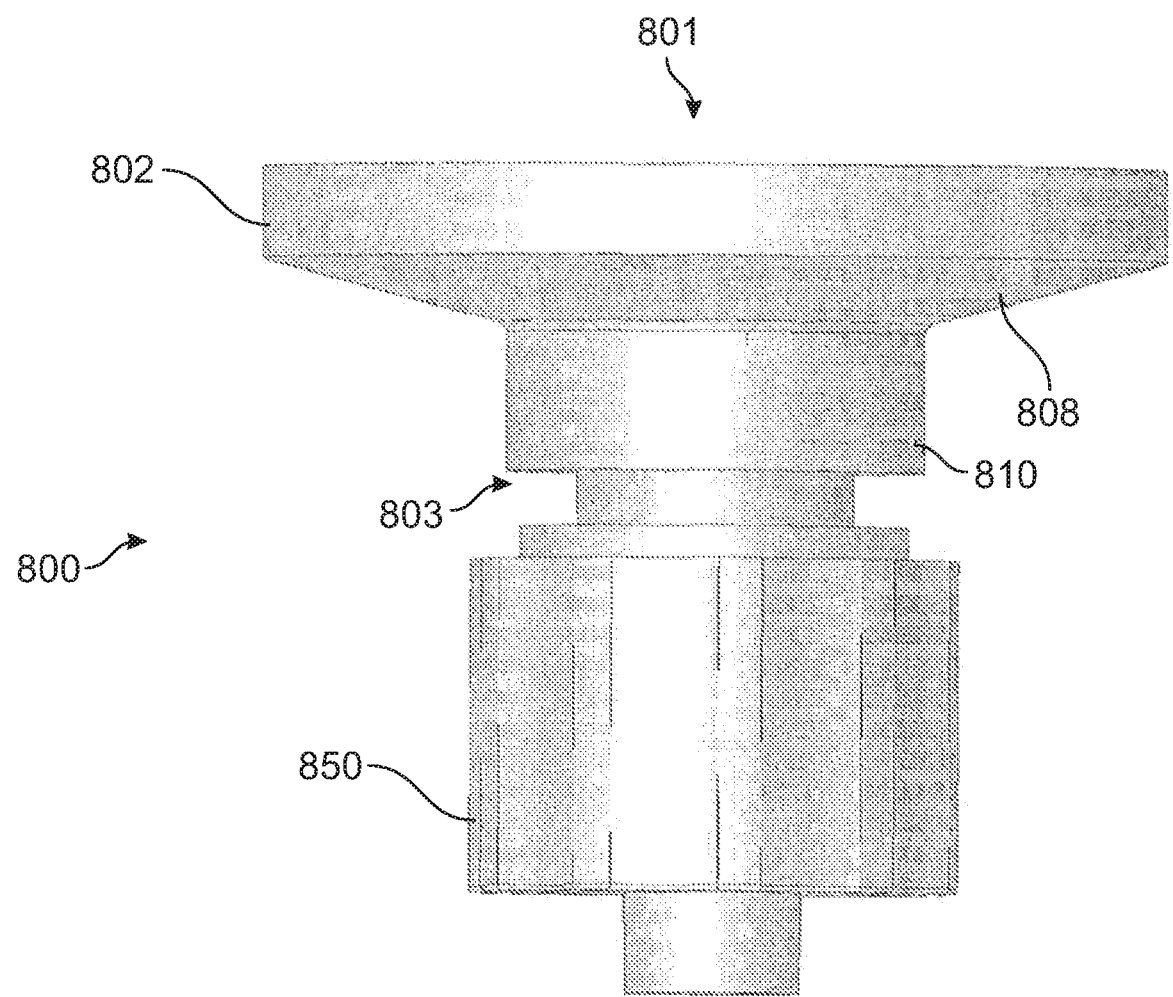
Figure 11C:
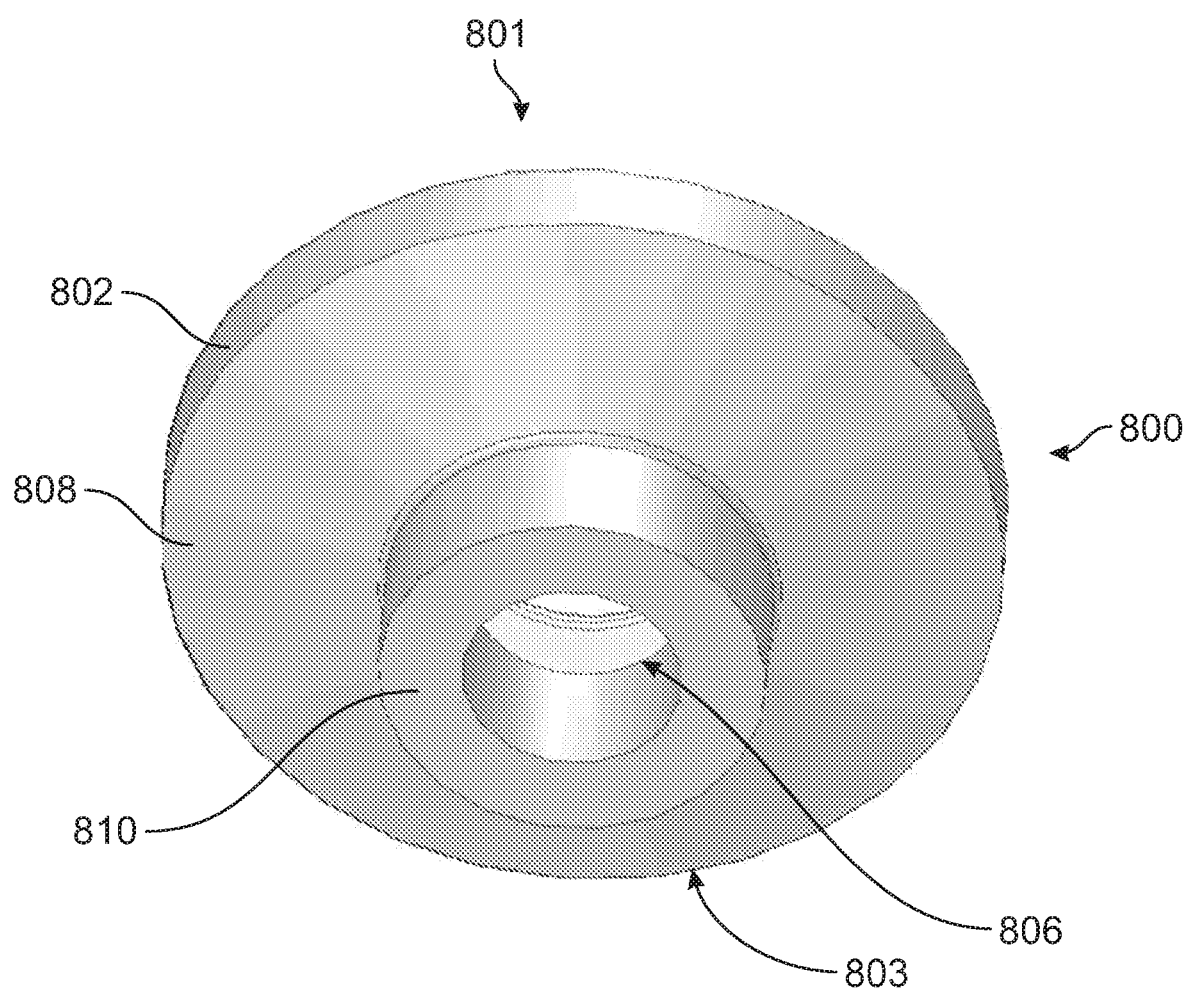

In some embodiments, a spooling suture system (e.g. suture spool or suture reel) can be used with embodiments of the above disclosed suturing devices. An example of such a suture spool 800 is shown in FIGS. 11A-C. The suture spool can advantageously allow for a suture or sutures to pass through the suturing device to its distal end or to the portion of the device where a suture end or portion will be held (such as the arms described above), while minimizing hangups, tangles, or other issues that can occur if the sutures were left unorganized outside of the patient. Any number of suture spools can be used and can be coordinated with the number of arms on the suturing devices described above. For example, there can be a 1:1 ratio between suture spools and arms. However, other ratios can be used as well, and there can be more or less suture spools than arms.

In some embodiments, the suture spool 800 can be located outside of the handle (e.g., external to the handle) and outside of the elongate body or shaft of the device itself (e.g., external to the elongate body or shaft). By having the suture spool 800 outside of the handle as disclosed herein, this frees up valuable space within the handle to perform other operations or have additional components, or even reduce the size of the handle. In some embodiments, the suture spool 800 can be located distal to the handle, but proximal to the arm(s) as discussed above. However, the particular location of the suture spools 800 is not limiting. In some embodiments, the suture spool 800 can be located on or inside the handle. In some embodiments, the suture spool 800 can be removably attachable to the suturing device, such as those discussed above. In some embodiments, the suture spool 800 may be fixedly coupled or mounted to the suturing device (either through or around the elongate member or the handle). Thus, the suture spool may move along with the suturing device. Thus, in some embodiments, the suture spools may not be able to move independent of the suturing device, at least during use.

The suturing spool 800 may have a proximal end 801 and a distal end 803. The distal end of the suturing spool is the end closer to the distal tip of the suturing device (as illustrated for example in FIG. 12), when the suture spool 800 is mounted to the suturing device). In some embodiments, the suturing spool 800 can be made up of a generally cylindrical container portion 802 located at the proximal end 801. This container portion 802 can be configured to hold excess suture within its internal surface. For example, the suture can wind (or circle) around an inner surface of the container surface, thus forming a generally cylindrical wrapped up suture, as shown in FIGS. 12-18. In some embodiments, the inner surface 804 of the container portion 802 can be grooved or internally threaded (such as a helical or screw-like threading) to allow for the suture to properly wind and be held within the container portion. In some embodiments, a proximal end of the suture can be connected into or held by the suture spool 800, with the distal end of the suture being attached to the arm of the suturing device until use.

In some embodiments, the suturing spool 800 can have an aperture 806 distal to the cylindrical container portion 802, with a tapered or conical section 808 therebetween. The suture can extend and wind from the container portion 802 along an inner conical surface of the tapered or conical section 808, through the aperture 806, and proceed towards the distal end of the suturing device.

Thus, the cylindrical container portion 802 and the conical section 808 can help guide the suture into the aperture 806 while preventing the suture from catching or tangling. In some embodiments, the suture can be loaded into the suture spool 800 so that it pulls through the aperture 806 opposite of how the suture was loaded in the container portion 802. For example, a first end of the suture can be attached in the suture spool 800 such as at the proximal end 801 and wrapped around the cylindrical container portion 802, such as along helical grooves, so that that when a second end of the suture is pulled through the aperture 806 the suture unwinds from the spool in a distal-first fashion.

In some embodiments, the suture spool 800 can contain a guide portion 810 distal to the tapered or conical section 808, shown in FIG. 11B. This guide portion 810 can therefore be located distal to the aperture 806. It may be internally formed to the suture spool 800 or may be attached to the suture spool 800. The guide portion 810 can be generally cylindrical, and can provide an extension to the aperture 806, thereby helping to guide the suture in the right direction. Further, the guide portion 810 can be used as a connection, for example having mating structures (either male or female, such as with threading) that allow it to be attached to another component, such as discussed below with respect to connector piece 850. However, the particular shape of the guide portion 810 is not limiting. FIG. 11C illustrates the suture spool 800 with no connector piece 850 so guide portion 810 is exposed.

On the opposite side of the aperture 806, e.g., on the proximal end 801 of the suture spool 800, the suture spool may be open, e.g., have an opening which may be defined by a rim of the cylindrical container portion 802 The opening of the suture spool 800 may be generally circular, though the particular shape of the opening 812 is not limiting. A suture cover 814 can be used to cover the proximal opening, though in some embodiments the proximal end of the suture spool 800 may instead be closed. The proximal cover 814 can prevent the suture from falling out of the spool 800 when in the container portion 802. In some embodiments, the cover 814 can be clear so that a user can see into a spool 800 and know how much suture is still left in the spool 800. However, in some embodiments the cover 814 may be opaque. In some embodiments, the cover 814 can be removable and replaceable on the container portion 802. In some embodiments, the cover 814 may have a generally circular aperture 812 smaller than the proximal opening of the suture spool to access the inside of the suture spool 800 and to more easily remove the cover.

As mentioned, the suture can unwind from the suture spool 800 through the aperture 806 during operation, such as discussed in detail above. In some embodiments, the suture spool 800, or other portion of the suturing device, can include a stopping mechanism to prevent further unwinding from the suture spool. For example, there can be another actuator on the devices discussed above that can stop the suture from unwinding. In some embodiments, an end of the suture can be attached within the suture spool 800, thus preventing unwinding of the full length of the suture.

Figure 12:
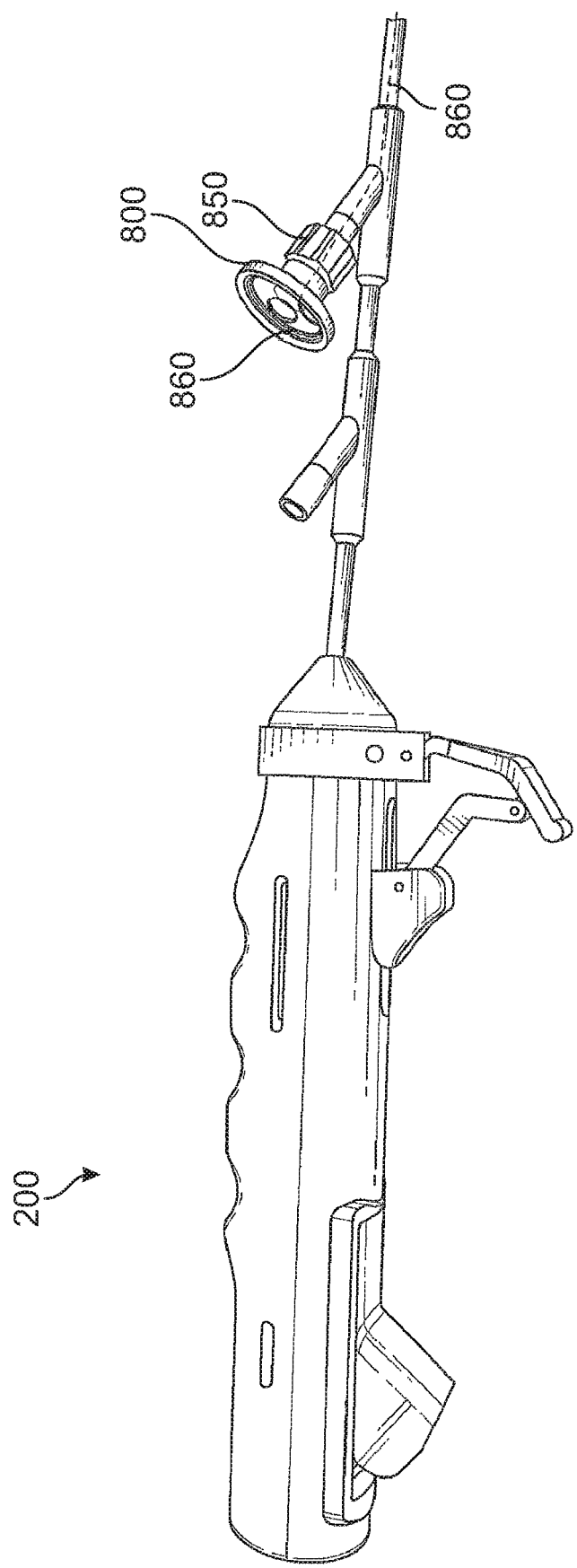
FIG. 12 illustrates a proximal end of an embodiment of a suture spool attached to an embodiment of a suturing device.

FIG. 12 illustrates an embodiment of a suture spool 800 attached to a suturing device, in particular to one of the dual devices 100/200 disclosed in detail above. Actuator 205 has been modified in this embodiment, though is still used to operate the needles. While only one of the suturing devices is shown, suturing device 200, it will be understood that the suture spools 800 can be used on all types of suturing devices, for example suturing device 100. Further, the suture spool 800 can be attached and/or located in generally the same position on either of the suturing devices 100/200, or the position can change between the two devices 100/200. The suture spool 800 can be rotated around the elongate body 204 and the particular location does not matter as long as there is access into the elongate body 204.

As shown in FIG. 12, the suture spool 800 can be attached to a suturing device, such as the suturing device 200, generally near, though distal to, the handle 202. The suture spool 800 may also be mounted over or around the elongate body 204. Further, the suture spool 800 can be angled with respect to the elongate body 204, for example at a 30, 35, 40, or 45 degree angle, though the particular angle is not limiting. Thus, the suture spool 800 can be offset from a longitudinal axis of the elongate body 204, or suturing device 200 as a whole. In some embodiments, the suture spool 800 can be offset from the side in which the arm 206 extends.

In some embodiments suture spool 800 can include a connector piece 850 to attach the suture spool 800 to a Y-junction component 852, which can connect to an inner lumen of the suturing device 200, in particular an inner lumen of the elongate body 204 through an aperture near the proximal end of the elongate body 204. The Y-junction component 852 may be integrally formed on the elongate body 204, or may be slid over and/or screwed/bonded to the elongate body 204. However, in some embodiments the connector piece 850 may be part of the Y-junction component 852, and thus may not be part of the suture spool. The connector piece 850 may insert into, or otherwise be attached to the guide portion 810. In some embodiments, the Y-junction component 842 can be built into the elongate body 204, and thus can be integrally formed with the elongate body 104. In some embodiments, the Y-junction component 852 can be added to the elongate body 204 and mounted thereover. In some embodiments, multiple Y-junctions can be included on the device 200, where an additional Y-junction may be used to thread a guide wire or for other purposes.

Figure 13:
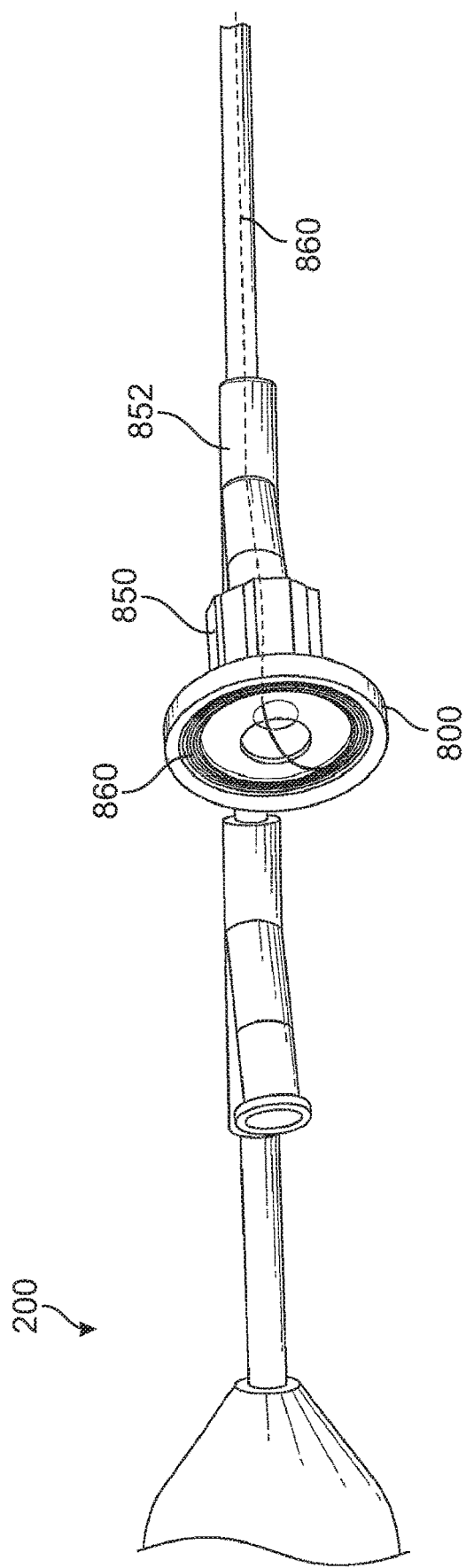
FIG. 13 illustrates an enlarged view of the suture spool of FIG. 12.

A close-up view of the suture spool 800 on the suturing device 200 is shown in FIG. 13. As shown, the suture 860 can wrap around the inner surface 804 of the suture spool 800 and extend distally through the aperture 806 of the suture spool 800. The suture 860 can then pass through the connector piece 850 and into the Y-junction component 852. This allows the suture 860 to pass through an opening (such as a side opening) in the elongate body 204 and pass into a lumen of the elongate body 204 as it travels towards the distal end of the suturing device 200. This can advantageously keep the suture 860 from tangling or catching as it extends proximally from the elongate body 204 to a location outside of the patient.

Figure 14:
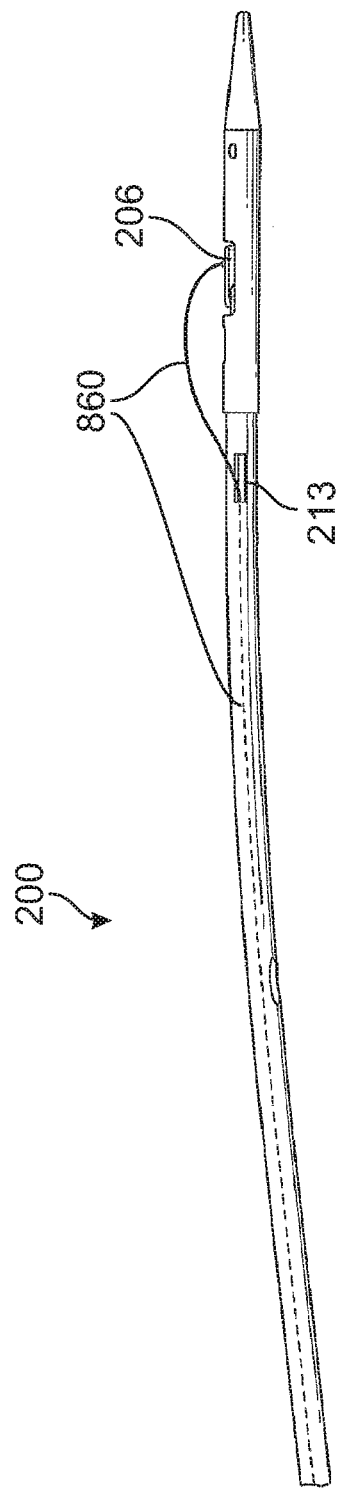
FIG. 14 illustrates a distal end of the suturing device of FIG. 12.

FIG. 14 illustrates a distal end of suturing device 200. As shown, the elongate body 204 can include an aperture 213 which allows the suture 860 to extend out of the elongate body 204. The suture 860 can then be attached to the suture clasp arm 206 at the distal end of the suturing device 200, and can be operated as discussed in detail above. For example, once the needle 212 catches the suture 860 at the distal end, the suture 860 can conveniently and easily be pulled out of the suture spool 800 (e.g., unwound) towards the distal end of the suturing device 200 without entanglement. Further, the suture 860 will be continued to be unwound out of the suture spool 800 when the suturing device 200 is pulled out of patient, such as discussed above with respect to FIGS. 4A-5E. Accordingly, the needle 212 (containing a first portion of the suture 860) will remain within the elongate body 204 as the device 200 is being removed, thus pulling the suture 860 out of the suture spool 800.

Figure 15:
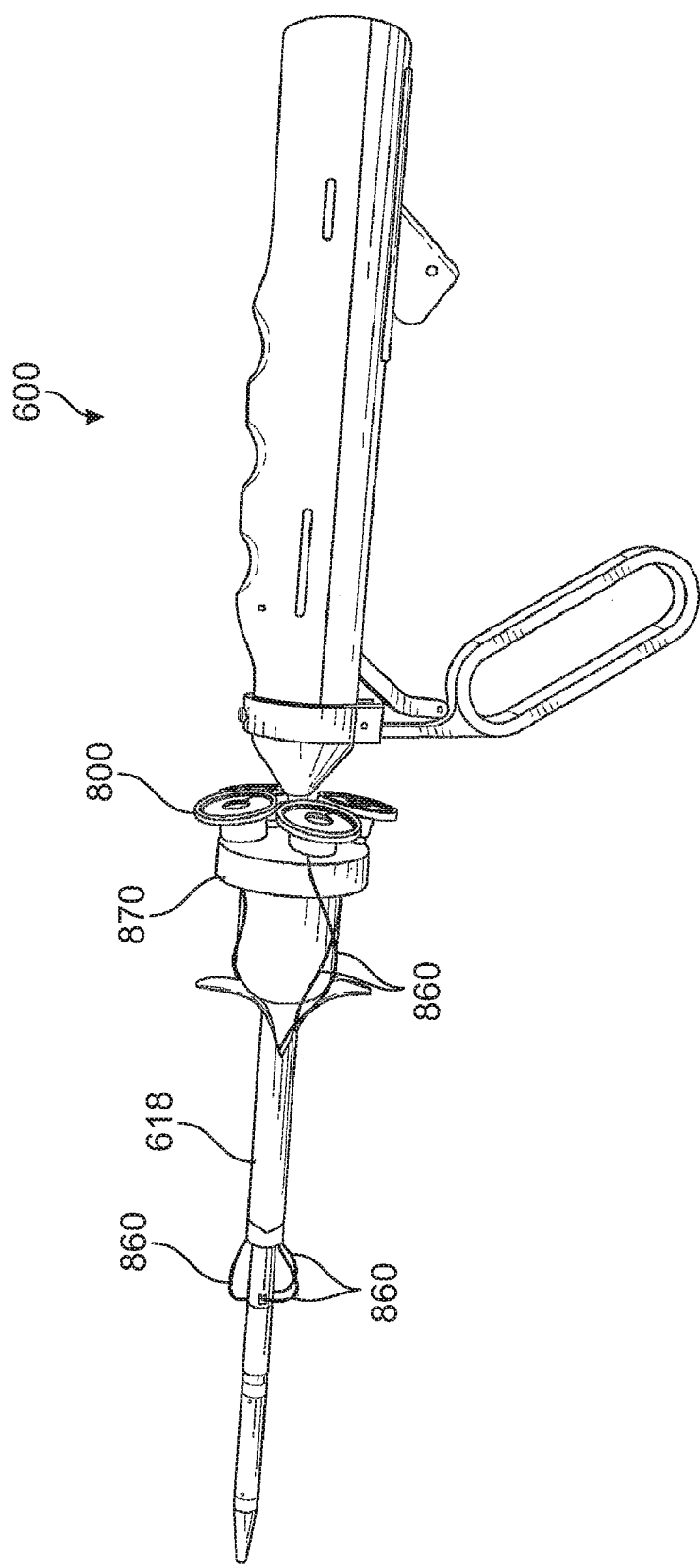
FIG. 15 illustrates an embodiment of a multi-armed suturing device having an embodiment including four suture spools.

Next, FIG. 15 illustrates an embodiment of suturing device 600 which can use embodiments of the suture spool 800. As shown, and described in detail above, the suturing device 600 can have four different suture clasp arms 610 and four different needles 630, and thus can accept four different sutures 860. Accordingly, four suture spools 800 can be used to hold four separate sutures. However, any number of suturing spools 800 can be used based on the number of different arms and needles. Further, in some embodiments a single suture spool 800 could provide multiple sutures to the arms.

Figure 16:
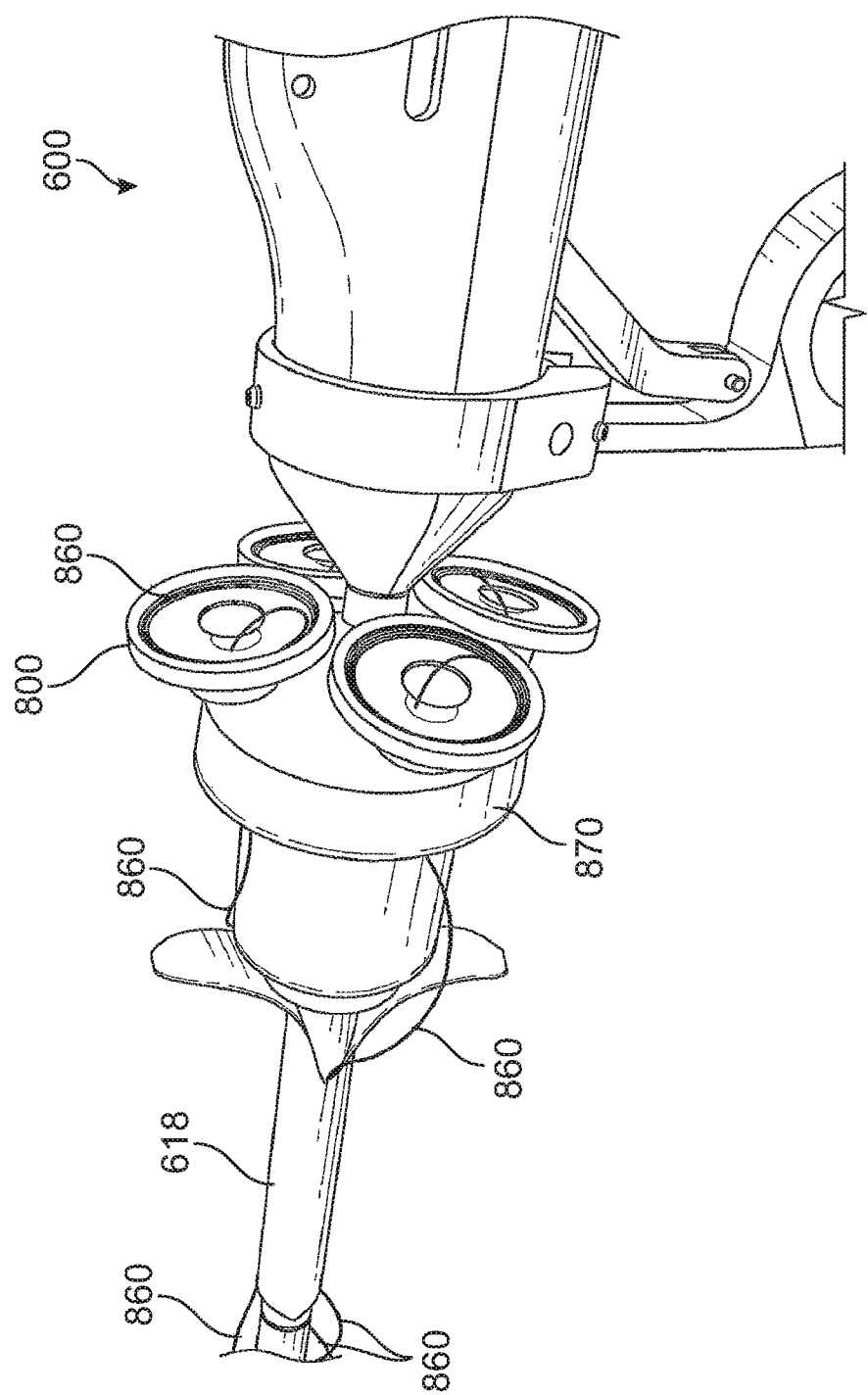
FIG. 16 shows a view of an embodiment including four suture spools from a proximal viewpoint of the device of FIG. 15.
Figure 17:
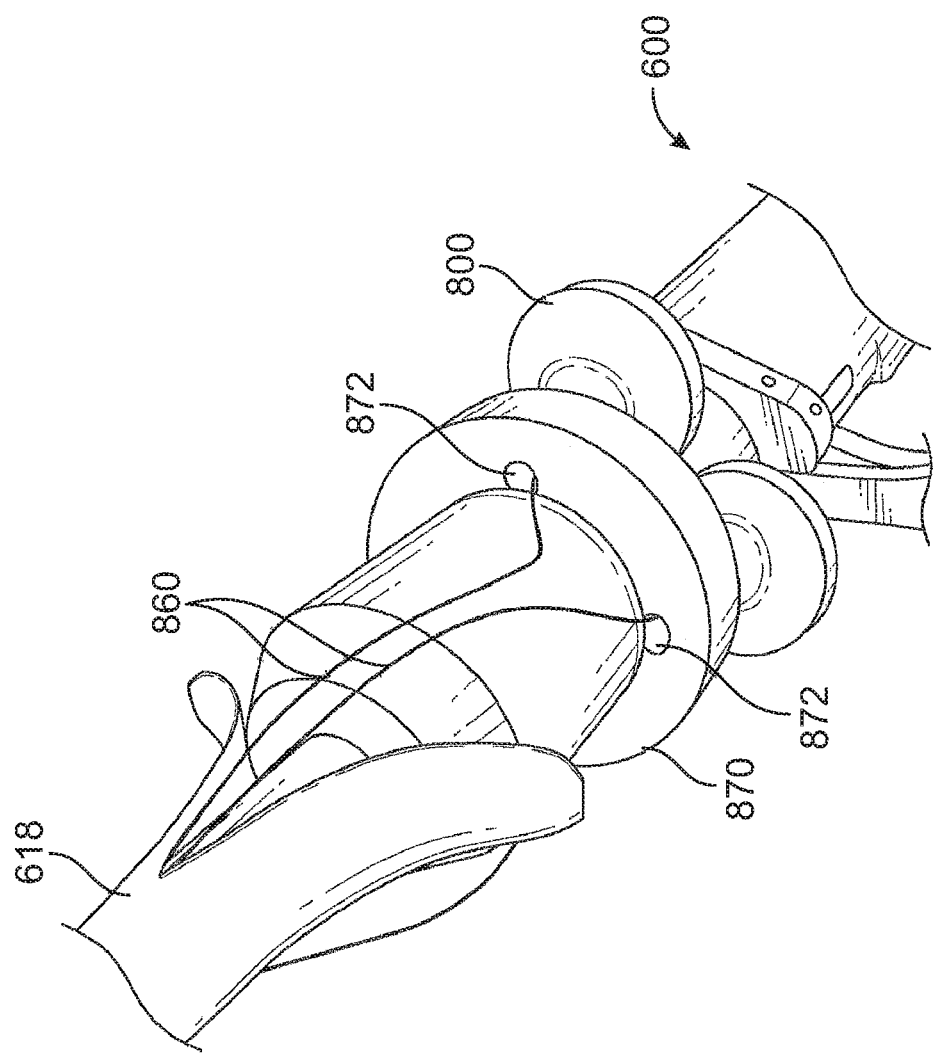
FIG. 17 shows a view of an embodiment including four suture spools from a distal viewpoint of the device of FIG. 15.

In some embodiments, a guide piece 870 can be used in conjunction with the multiple suture spools 800 to provide the sutures 860 to the distal end of the device 600 while reducing or eliminating tangles and/or knots in the sutures 860. As shown in FIGS. 16-17, the guide piece 870 can be located distal to the suture spools 800 but proximal to the second sheath 618. The guide piece 870 can be generally circular in profile with a thickness, thereby forming a disc-like structure. However, the particular shape of the guide piece 870 is not limiting and any number of shapes can be used. Further, as shown, the guide piece 870 can have smaller profile in diameter than the combined diameter of all of the suture spools 800, but this is not limiting.

The guide piece 870 can include a number of apertures 872 equal to the number of suture spools 800 being used. As shown, the guide piece 870 can have four apertures 872 to align with the four distal apertures 806 of the four suture spools 800. Thus, the suture 860 can begin in the suture spools 800, extend through the distal apertures 806 of the suture spools 800, and extend through a respective aperture 872 in the guide piece 870. This can prevent the sutures 860 from interacting with one another during the procedure, thus reducing entanglements. However, the guide piece 870 may have a different number of apertures 870 than spools 800, e.g., more or less apertures 870 than spools 800. Further, in some embodiments a guide piece 870 may not be used. In some embodiments, the guide portion 810 of the suture spool 800 can be attached to the guide piece 870.

In some embodiments, the suture spools 800 can be fused to the guide piece 870. In some embodiments, the suture spools 800 can be removably attachable to the guide piece 870. In some embodiments, the suture spools 800 are mounted to the guide piece 870, either removably or not removably. In some embodiments, the suture spools 800 and guide piece 870 can be formed of a single component, such as a single molded component.

Figure 18:
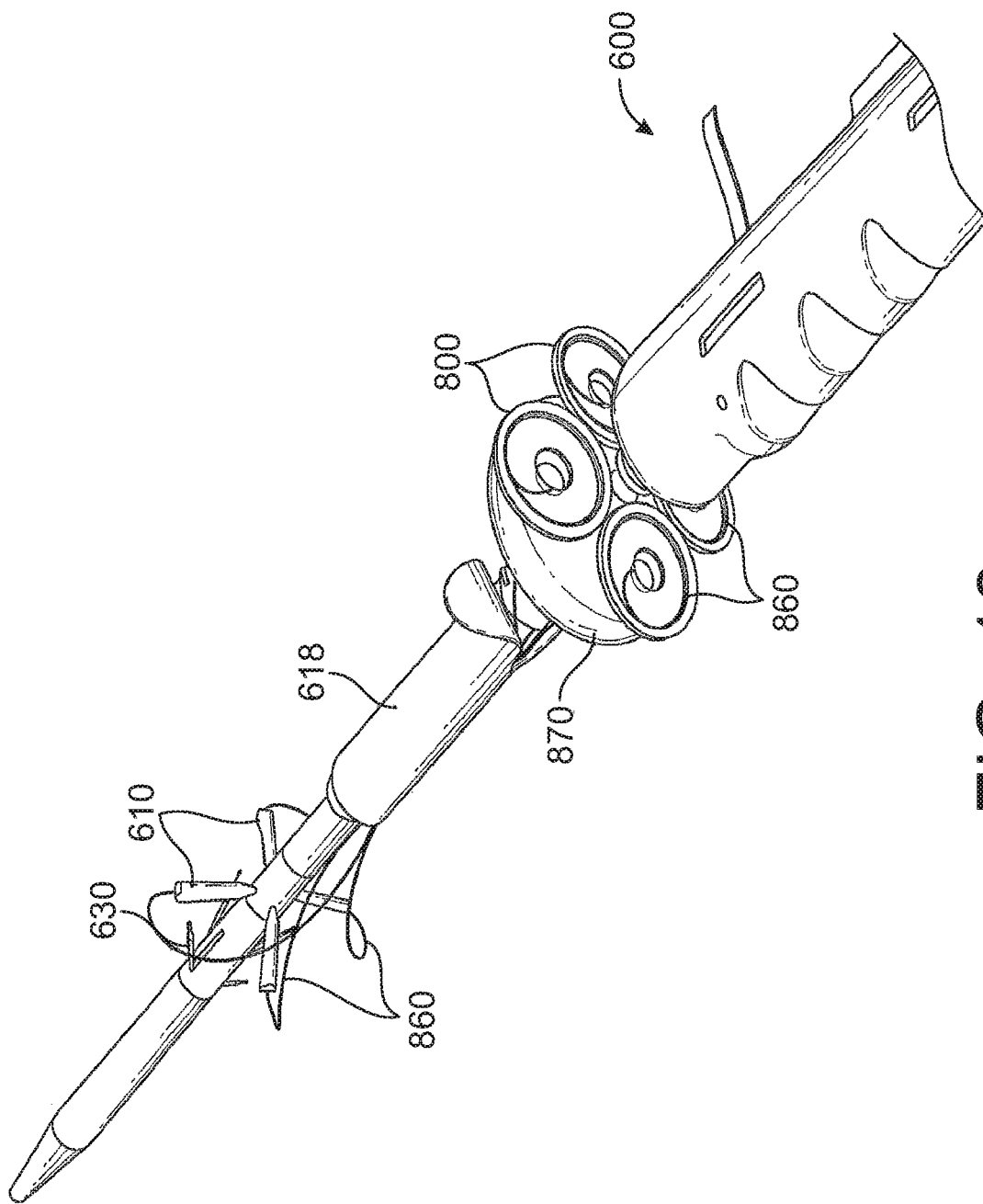
FIG. 18 shows an embodiment of the multi-armed suturing device of FIG. 15 with the arms deployed.

As the sutures 860 extend distally from the suture spools 800 and the guide piece 870, they can pass through the lumen of the second sheath 618, as discussed in detail above. The second sheath 618 can generally guide the sutures 860 along the elongate body 606 from the suture spools towards the distal end of the elongate body 608. The sutures 860 can then extend from the distal end of the second sheath 618 and be attached to respective suture clasp arms 610, thereby allowing the device 600 to operate in a manner as discussed in detail above. Specifically, the suture 860 will be retained on the suture clasp arm 610 until the needle 630 pulls the suture 860 distally into the elongate body 606, starting the unwinding of the suture 860. The suture 860 will be continued to be unwound out of the suture spool 800 when the suturing device 600 is pulled out of patient, such as discussed above with respect to FIGS. 10A-J. Accordingly, the needle 630 (containing a first portion of the suture 860) will remain within the elongate body 605 as the device 600 is being removed, thus pulling the suture 860 out of the suture spool 800. FIG. 18 shows the device 600 with the suture clasp arms 610 in the deployed position with the needles 630 configured to move proximally towards the suture clasp arms 610.

Summary of Some Embodiments

A number of different suturing devices and methods are disclosed herein.

Embodiment 1

A device for suturing biological tissue, the device comprising an elongate body having a proximal end and a distal end, at least one arm extendible from the elongate body, the at least one arm configured to move between a retracted position wherein the at least one arm is within the elongate body and a deployed position wherein the at least one arm extends away from the elongate body, the at least one arm configured to hold a first portion of a suture, at least one needle moveable relative to the elongate body between a retracted position and a deployed position, wherein the at least one needle when moving from its retracted position to its deployed position is configured to pass through tissue and capture the suture first portion held by the at least one arm, and is further configured to move from the deployed position to the retracted position to bring the suture first portion through the tissue, a handle located at the proximal end of the elongate body, the handle having one or more actuators configured to cause movement of the at least one arm and the at least one needle, and at least one suture spool mountable in fixed relationship to and located external to the elongate body and the handle, the at least one suture spool configured to retain a second portion of the suture, wherein, when the suture first portion is captured by the at least one needle and the at least one needle brings the suture first portion through the tissue, the at least one suture spool is configured such that the at least one suture unwinds from the at least one suture spool.

Embodiment 2

The device of Embodiment 1, wherein at least one suture spool can comprise an aperture, wherein the suture unwinds through the aperture.

Embodiment 3

The device of Embodiment 1 or 2, wherein the at least one suture spool comprises an inner circumference around which the suture winds.

Embodiment 4

The device of any one of Embodiments 1-3, wherein the at least one spool comprising a cylindrical portion having an open proximal end, an aperture located on a distal end, and a conical portion between the cylindrical portion and the aperture.

Embodiment 5

The device of any one of Embodiments 1-4, wherein the at least one suture spool is mountable between the handle and the at least one arm.

Embodiment 6

The device of any one of Embodiments 1-5, wherein the at least one spool is mountable around the elongate body such that the at least one spool is offset to one side of a longitudinal axis of the elongate body.

Embodiment 7

The device of any one of Embodiments 1-6, wherein the at least one spool is attachable to a Y-connector positioned around the elongate body.

Embodiment 8

The device of any one of Embodiments 1-7, comprising at least two spools mounted around the elongate body, the at least two spools corresponding to two arms extendible from the elongate body and two needles configured to capture sutures held by the two arms.

Embodiment 9

The device of any one of Embodiments 1-8, comprising four spools mounted around the elongate body, the four spools corresponding to four arms extendible from the elongate body and four needles configured to capture sutures held by the four arms.

Embodiment 10

The device of any one of Embodiments 1-9, wherein the at least one suture spool is mounted in fixed relationship to and located external to the elongate body and the handle, and the at least one suture spool contains a suture wound thereon that extends to the at least one arm.

Embodiment 11

The device of any one of Embodiments 1-10, wherein the at least one needle moves distally to proximally when moving from the retracted position to the deployed position.

Embodiment 12

The device of any one of Embodiments 1-10, wherein the at least one needle moves proximally to distally when moving from the retracted position to the deployed position.

Embodiment 13

The device of any one of Embodiments 1-12, wherein the at least one arm is located at or near the distal end of the elongate body.

Embodiment 14

The device of any one of Embodiments 1-13, further comprising an outer sheath located over the elongate body, wherein the at least one suture is configured to extend from the at least one suture spool between the outer sheath and the elongate body to the at least one arm.

Embodiment 15

The device of Embodiment 14, wherein the outer sheath comprises a peelable outer sheath.

Embodiment 16

A device for suturing a body opening such as a patent foramen ovale (PFO), the device comprising an elongate body having a proximal end and a distal end, at least one arm extendible from the elongate body, the at least one arm configured to move between a retracted position wherein the at least one arm is within the elongate body and a deployed position wherein the at least one arm extends away from the elongate body, the at least one arm configured to hold a first portion of a suture, at least one needle moveable relative to the elongate body between a retracted position and a deployed position, wherein the at least one needle when moving from its retracted position to its deployed position is configured to pass through tissue and capture the suture first portion held by the at least one arm, and is further configured to move from the deployed position to the retracted position to bring the suture first portion through the tissue, a handle located at the proximal end of the elongate body, the handle having a first actuator configured to cause movement of the at least one arm and a second actuator configured to cause movement of the at least one needle, and at least one suture spool mounted around the elongate body between the handle and the at least one arm, the at least one suture spool configured to retain a second portion of the suture, wherein, when the suture first portion is captured by the at least one needle and the at least one needle brings the suture first portion through the tissue, the at least one suture spool is configured such that the at least one suture unwinds from the at least one suture spool.

Embodiment 17

The device of any one of Embodiment 16, wherein the at least one suture spool is mounted around the elongate body with a Y-connector mounted on the elongate body.

Embodiment 18

The device of any one of Embodiments 16-17, further comprising a suture wound on the at least one suture spool, the suture extending from the suture spool through an interior of the elongate body to the at least one arm.

Embodiment 19

The device of any one of Embodiments 16-18, comprising a single arm and a single needle.

Embodiment 20

The device of Embodiment 19, wherein the arm is proximal to the needle.

Embodiment 21

The device of Embodiment 19, wherein the arm is distal to the needle.

Embodiment 22

A suturing device for suturing a body opening such as a transapical opening in the heart, the device comprising an elongate body having a proximal end and a distal end, four arms extendible from the elongate body, the four arms configured to move between a retracted position wherein each of the four arms is within the elongate body and a deployed position wherein the each of the four arms extends away from the elongate body, each of the four arms configured to hold a first portion of each of four sutures, four needles moveable relative to the elongate body between a retracted position and a deployed position, wherein each of the four needles when moving from its retracted position to its deployed position is configured to pass through tissue and capture the suture first portion held by each of the four arms, and is further configured to move from the deployed position to the retracted position to bring each of the suture first portions through the tissue, a handle located at the proximal end of the elongate body, the handle having at least a first actuator configured to cause movement of each of the four arms and at least a second actuator configured to cause movement of each of the four needles, and four suture spools mounted around the elongate body between the handle and the four arms, each of the four suture spools configured to retain a second portion of each of the four sutures, and a peel-away sheath at least partially surrounding the elongate body, each of the four sutures configured to extend from the four suture spools through the peel-away sheath to the four arms, wherein, when each of the first portions of the four sutures is captured by each of the four needles and each of the four needles brings each of the suture first portions through the tissue, the four suture spools are configured such that each of the four sutures unwinds from each of the four suture spools.

Embodiment 23

The device of Embodiment 22, further comprising a guide piece located distal to the four suture spools and proximal to the peel-away sheath, the guide piece having four apertures, wherein each of the four sutures extends through one of the four apertures.

Embodiment 24

A method of suturing biological tissue, comprising using the suturing device of any one of Embodiments 1-23 to close a body opening.

Embodiment 25 the method of Embodiment 24, wherein the suturing device is used to close a patent foramen ovale.

Embodiment 26

The method of Embodiment 25, comprising using two separate suturing devices close the patent foramen ovale.

Embodiment 27

The method of Embodiment 24, wherein the suturing device is used to close an opening in the heart.

From the foregoing description, it will be appreciated that an inventive suturing devices and methods of use are disclosed. While several components, techniques and aspects have been described with a certain degree of particularity, it is manifest that many changes can be made in the specific designs, constructions and methodology herein above described without departing from the spirit and scope of this disclosure.

Certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as any subcombination or variation of any subcombination.

Moreover, while methods may be depicted in the drawings or described in the specification in a particular order, such methods need not be performed in the particular order shown or in sequential order, and that all methods need not be performed, to achieve desirable results. Other methods that are not depicted or described can be incorporated in the example methods and processes. For example, one or more additional methods can be performed before, after, simultaneously, or between any of the described methods. Further, the methods may be rearranged or reordered in other implementations. Also, the separation of various system components in the implementations described above should not be understood as requiring such separation in all implementations, and it should be understood that the described components and systems can generally be integrated together in a single product or packaged into multiple products. Additionally, other implementations are within the scope of this disclosure.

Conditional language, such as "can," "could," "might," or "may," unless specifically stated otherwise, or otherwise understood within the context as used, is generally intended to convey that certain embodiments include or do not include, certain features, elements, and/or steps. Thus, such conditional language is not generally intended to imply that features, elements, and/or steps are in any way required for one or more embodiments.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than or equal to 10% of, within less than or equal to 5% of, within less than or equal to 1% of, within less than or equal to 0.1% of, and within less than or equal to 0.01% of the stated amount. If the stated amount is 0 (e.g., none, having no), the above recited ranges can be specific ranges, and not within a particular % of the value. For example, within less than or equal to 10 wt./vol. % of, within less than or equal to 5 wt./vol. % of, within less than or equal to 1 wt./vol. % of, within less than or equal to 0.1 wt./vol. % of, and within less than or equal to 0.01 wt./vol. % of the stated amount.

Some embodiments have been described in connection with the accompanying drawings. The figures are drawn to scale, but such scale should not be limiting, since dimensions and proportions other than what are shown are contemplated and are within the scope of the disclosed inventions. Distances, angles, etc. are merely illustrative and do not necessarily bear an exact relationship to actual dimensions and layout of the devices illustrated. Components can be added, removed, and/or rearranged. Further, the disclosure herein of any particular feature, aspect, method, property, characteristic, quality, attribute, element, or the like in connection with various embodiments can be used in all other embodiments set forth herein. Additionally, it will be recognized that any methods described herein may be practiced using any device suitable for performing the recited steps.

While a number of embodiments and variations thereof have been described in detail, other modifications and methods of using the same will be apparent to those of skill in the art. Accordingly, it should be understood that various applications, modifications, materials, and substitutions can be made of equivalents without departing from the unique and inventive disclosure herein or the scope of the claims.

What is claimed is:

1. A device for suturing biological tissue, the device comprising:
  an elongate body having a proximal end and a distal end;
  at least one arm extendible from the elongate body, the at least one arm configured to move between a retracted position wherein the at least one arm is within the elongate body and a deployed position wherein the at least one arm extends away from the elongate body, the at least one arm configured to hold a first portion of a suture;
  at least one needle moveable relative to the elongate body between a retracted position and a deployed position, wherein the at least one needle when moving from its retracted position to its deployed position is configured to pass through tissue and capture the suture first portion held by the at least one arm, and is further configured to move from the deployed position to the retracted position to bring the suture first portion through the tissue;

a handle located at the proximal end of the elongate body, the handle having one or more actuators configured to cause movement of the at least one arm and the at least one needle; and at least one suture spool mountable in fixed relationship to and located external to the elongate body and the handle, the at least one suture spool configured to retain a second portion of the suture, wherein the at least one suture spool comprises a cylindrical portion having an open proximal end, an aperture located on a distal end, and a conical portion between the cylindrical portion and the aperture, wherein, when the suture first portion is captured by the at least one needle and the at least one needle brings the suture first portion through the tissue, the at least one suture spool is configured such that the at least one suture unwinds from the at least one suture spool.

2. The device of claim 1, wherein the suture unwinds through the aperture of the at least one suture spool.

3. The device of claim 1, wherein the at least one suture spool comprises an inner circumference around which the suture winds.

4. The device of claim 1, wherein the at least one suture spool is mountable between the handle and the at least one arm.

5. The device of claim 1, wherein the at least one spool is mountable around the elongate body such that the at least one spool is offset to one side of a longitudinal axis of the elongate body.

6. The device of claim 1, wherein the at least one spool is attachable to a Y-connector positioned around the elongate body.

7. The device of claim 1, comprising at least two spools mounted around the elongate body, the at least two spools corresponding to two arms extendible from the elongate body and two needles configured to capture sutures held by the two arms.

8. The device of claim 1, comprising four spools mounted around the elongate body, the four spools corresponding to four arms extendible from the elongate body and four needles configured to capture sutures held by the four arms.

9. The device of claim 1, wherein the at least one suture spool is mounted in fixed relationship to and located external to the elongate body and the handle, and the at least one suture spool contains a suture wound thereon that extends to the at least one arm.

10. The device of claim 1, wherein the at least one needle moves distally to proximally when moving from the retracted position to the deployed position.

11. The device of claim 1, wherein the at least one needle moves proximally to distally when moving from the retracted position to the deployed position.

12. The device of claim 1, wherein the at least one arm is located at or near the distal end of the elongate body.

13. The device of claim 1, further comprising a peelable outer sheath located over the elongate body, wherein the at least one suture is configured to extend from the at least one suture spool between the outer sheath and the elongate body to the at least one arm.

14. The device of claim 13, wherein the outer sheath comprises a peelable outer sheath.

15. A device for suturing a body opening, the device comprising:

an elongate body having a proximal end and a distal end;

at least one arm extendible from the elongate body, the at least one arm configured to move between a retracted position wherein the at least one arm is within the elongate body and a deployed position wherein the at least one arm extends away from the elongate body, the at least one arm configured to hold a first portion of a suture;

at least one needle moveable relative to the elongate body between a retracted position and a deployed position, wherein the at least one needle when moving from its retracted position to its deployed position is configured to pass through tissue and capture the suture first portion held by the at least one arm, and is further configured to move from the deployed position to the retracted position to bring the suture first portion through the tissue;

a handle located at the proximal end of the elongate body, the handle having a first actuator configured to cause movement of the at least one arm and a second actuator configured to cause movement of the at least one needle; and at least one suture spool mounted around the elongate body between the handle and the at least one arm, the at least one suture spool configured to retain a second portion of the suture, wherein the at least one suture spool is mounted around the elongate body with a Y-connector mounted on the elongate body, wherein, when the suture first portion is captured by the at least one needle and the at least one needle brings the suture first portion through the tissue, the at least one suture spool is configured such that the at least one suture unwinds from the at least one suture spool.

16. The device of claim 15, further comprising a suture wound on the at least one suture spool, the suture extending from the suture spool through an interior of the elongate body to the at least one arm.

17. The device of claim 15, comprising a single arm and a single needle.

18. The device of claim 17, wherein the arm is proximal to the needle.

19. The device of claim 17, wherein the arm is distal to the needle.

20. A suturing device for suturing a body opening, the device comprising:

an elongate body having a proximal end and a distal end;

four arms extendible from the elongate body, the four arms configured to move between a retracted position wherein each of the four arms is within the elongate body and a deployed position wherein the each of the four arms extends away from the elongate body, each of the four arms configured to hold a first portion of each of four sutures;

four needles moveable relative to the elongate body between a retracted position and a deployed position, wherein each of the four needles when moving from its retracted position to its deployed position is configured to pass through tissue and capture the suture first portion held by each of the four arms, and is further configured to move from the deployed position to the retracted position to bring each of the suture first portions through the tissue;

a handle located at the proximal end of the elongate body, the handle having at least a first actuator configured to cause movement of each of the four arms and at least a second actuator configured to cause movement of each of the four needles; and four suture spools mounted around the elongate body between the handle and the four arms, each of the four suture spools configured to retain a second portion of each of the four sutures, wherein at least one of the four suture spool comprises a cylindrical portion having an open proximal end, an aperture located on a distal end, and a conical portion between the cylindrical portion and the aperture, wherein, when each of the first portions of the four sutures is captured by each of the four needles and each of the four needles brings each of the suture first portions through the tissue, the four suture spools are configured such that each of the four sutures unwinds from each of the four suture spools.

21. The suturing device of claim 20, further comprising a peel-away sheath at least partially surrounding the elongate body, each of the four sutures configured to extend from the four suture spools through the peel-away sheath to the four arms.

22. The suturing device of claim 21, further comprising a guide piece located distal to the four suture spools and proximal to the peel-away sheath, the guide piece having four apertures, wherein each of the four sutures extends through one of the four apertures.

\* \* \* \* \*